(12) United States Patent
Cohen et al.

(10) Patent No.: US 10,881,698 B2
(45) Date of Patent: Jan. 5, 2021

(54) DIAGNOSIS AND TREATMENT FOR RESPIRATORY TRACT DISEASES

(71) Applicants: THE TRUSTEES OF THE UNIVERSITY OF PENNSYLVANIA, Philadelphia, PA (US); MONELL CHEMICAL SENSES CENTER, Philadelphia, PA (US)

(72) Inventors: Noam A. Cohen, Bala Cynwyd, PA (US); Robert J. Lee, Pittsburgh, PA (US); Danielle R. Reed, Glenside, PA (US)

(73) Assignees: THE TRUSTEES OF THE UNIVERSITY OF PENNSYLVANIA, Philadelphia, PA (US); MONELL CHEMICAL SENSES CENTER, Philadelphia, PA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 743 days.

(21) Appl. No.: 14/374,763

(22) PCT Filed: Jan. 25, 2013

(86) PCT No.: PCT/US2013/023185
§ 371 (c)(1),
(2) Date: Jul. 25, 2014

(87) PCT Pub. No.: WO2013/112865
PCT Pub. Date: Aug. 1, 2013

(65) Prior Publication Data
US 2015/0017099 A1 Jan. 15, 2015

Related U.S. Application Data

(60) Provisional application No. 61/591,425, filed on Jan. 27, 2012, provisional application No. 61/697,652, filed on Sep. 6, 2012.

(51) Int. Cl.
| | | |
|---|---|---|
| A61K 49/00 | (2006.01) |
| A61K 36/185 | (2006.01) |
| G01N 33/68 | (2006.01) |
| G01N 33/566 | (2006.01) |
| A61K 31/167 | (2006.01) |
| A61K 31/365 | (2006.01) |
| A61K 31/4709 | (2006.01) |
| A61K 31/513 | (2006.01) |
| A61K 45/06 | (2006.01) |
| C12Q 1/6883 | (2018.01) |
| G01N 33/50 | (2006.01) |
| A61K 31/49 | (2006.01) |

(52) U.S. Cl.
CPC .......... *A61K 36/185* (2013.01); *A61K 31/167* (2013.01); *A61K 31/365* (2013.01); *A61K 31/4709* (2013.01); *A61K 31/513* (2013.01); *A61K 45/06* (2013.01); *C12Q 1/6883* (2013.01); *G01N 33/502* (2013.01); *G01N 33/566* (2013.01); *G01N 33/6893* (2013.01); *A61K 31/49* (2013.01); *C12Q 2600/156* (2013.01); *G01N 2333/705* (2013.01); *G01N 2500/04* (2013.01); *G01N 2800/14* (2013.01)

(58) Field of Classification Search
None
See application file for complete search history.

(56) References Cited

U.S. PATENT DOCUMENTS

| | | | | |
|---|---|---|---|---|
| 1,741,761 | A * | 12/1929 | Engels | ................. C07D 453/04 |
| | | | | 546/134 |
| 7,883,856 | B2 * | 2/2011 | Li | ....................... G01N 33/5008 |
| | | | | 435/7.1 |
| 2002/0187136 | A1 | 12/2002 | Loomis et al. | |
| 2004/0209852 | A1 | 10/2004 | Chaudry et al. | |
| 2006/0276483 | A1 * | 12/2006 | Surber | ................. A61K 9/0075 |
| | | | | 514/253.08 |

(Continued)

OTHER PUBLICATIONS

Chang et al. (Arch. Oral Biol. 2006, 51, 427-432).*
Gray et al., (Chronic Rhinosinusitis in Adults. Evidence-Based Otolaryngology. Springer New York, 2008, 489-516).*
Grassin-Delyle et al. (Respiratory Res. 2013, 14, pp. 1-14).*
Meyerhof et al. (Chem. Senses 2010, 35, 157-170).*
Hayes et al. (Chem. Senses 2008, 33, 255-265).*
Dotson et al. (PLos One 2008, 3, e3974, p. 1-10).*

(Continued)

*Primary Examiner* — Michael G. Hartley
*Assistant Examiner* — Melissa J Perreira
(74) *Attorney, Agent, or Firm* — Mark S. Cohen; Pearl Cohen Zedek Latzer Baratz LLP

(57) ABSTRACT

The invention provides methods and compositions for the diagnosis, prognosis and treatment of respiratory tract diseases. Specifically, the invention provides diagnosis, prognosis and treatment of respiratory infections using bitter and sweet taste signal transduction pathways. In one aspect, the invention relates to a method for treating a respiratory infection by administering a composition to the respiratory tract of a subject in an amount capable of activating bitter taste signaling and/or inhibiting sweet taste signaling. The composition comprises at least a bitter receptor agonist and, optionally, a pharmaceutically acceptable carrier for delivering the composition to the respiratory tract. In another aspect, the invention relates to a composition for treatment of a respiratory infection. Such composition comprises at least a bitter receptor agonist and, optionally, a pharmaceutically acceptable carrier for delivering the composition to the respiratory tract.

14 Claims, 25 Drawing Sheets

Specification includes a Sequence Listing.

(56) References Cited

U.S. PATENT DOCUMENTS

2008/0066739 A1* 3/2008 LeMahieu ............ A61M 11/041
  128/200.14
2008/0241281 A1 10/2008 Vediyappan et al.
2009/0196930 A1 8/2009 Surber et al.
2013/0131108 A1* 5/2013 Liggett ................ A61K 31/165
  514/313

OTHER PUBLICATIONS

Wong et al. (Art. Cells, Blood Subs and Immob. Biotech. 2000, 28, 415-428).*
Meyerhof, et al. "The molecular receptive ranges of human TAS2R bitter taste receptors", Chem. Senses. 2010; 35(2):157-70.
Tizzano et al., "Nasal chemosensory cells use bitter taste signaling to detect irritants and bacterial signals", Proceedings of the National Academy of Sciences, Feb. 2010, vol. 107, No. 7, pp. 3210-3215.
Shah et al., "Motile Cilia of Human Airway Epithelia are Chemosensory", Science, Aug. 2009, vol. 325, pp. 1131-1134.
Kaliner et al., "Sinusitis: Bench to bedside current findings, future directions", The Journal of Allergy and Clinical Immunology, Jun. 1997, vol. 99, iss. 6, pp. S829-S847.
Reed et al., "Diverse Tastes: Genetics of sweet and bitter perception", Physiology and Behaviour, Jun. 2006, vol. 88, No. 3, pp. 215-226.
Henkin et al., "Divergent taste responsiveness to fruit of the tree Antidesma bunius", Nature, Feb. 1977, vol. 265, pp. 536-537.
Lee et al., "T2R38 taste receptor polymorphisms underlie susceptibility to upper repiratory infection", The Journal of Clinical Investigation, Nov. 2012, vol. 122, No. 11, pp. 4145-4159.
Adappa et al., "Genetics of taste receptor T2R38 correlates which chronic rhinosinusitis necessitating surgical intervention", International Forum of Allergy and Rhinology, Mar. 2013, vol. 3, No. 3, pp. 184-187.

* cited by examiner

DIAGNOSIS AND TREATMENT FOR RESPIRATORY TRACT DISEASES

CROSS-REFERENCE TO RELATED APPLICATIONS

This application is a National Phase Application of PCT International Application No. PCT/US13/23185, International Filing Date Jan. 25, 2013, claiming priority to U.S. Provisional Patent Application 61/591,425, filed Jan. 27, 2012, and U.S. Provisional Patent Application 61/697,652, filed Sep. 6, 2012, all of which are incorporated by reference herein in their entirety.

STATEMENT OF GOVERNMENT INTEREST

The work described herein was, in part, supported by United States Public Health Service grants P30DC011735, R01DC004698, P50DC000214, and R01DC010842. The United States government may have certain rights in this application.

FIELD OF THE INVENTION

The invention relates generally to methods and compositions for diagnosis, prognosis and treatment of respiratory tract diseases. Specifically, the invention relates to methods and compositions for diagnosis, prognosis and treatment of respiratory infections using bitter and sweet taste signal transduction pathways.

BACKGROUND OF THE INVENTION

Respiratory infections such as infections of the upper respiratory tract, especially chronic rhinosinusitis (CRS), are relatively common illnesses and represent serious health challenges. For instance, CRS affects about 16% of Americans and has symptoms that severely impact the quality of the patient's life, including nasal congestion and discharge, headache and/or facial pressure, anosmia, and fatigue Rhinosinusitis annually results in 13 million physician visits, 73 million restricted activity days, and an aggregated cost of about 6 billion dollars.

The colonization of microbes in the sinonasal cavity contributes to the pathophysiology of CRS. Development of effective therapeutics for controlling the microbes in the upper respiratory tract is needed to improve the quality of life for millions of people suffering from CRS.

Antibiotics are one treatment for upper respiratory infections, but antibiotics become ineffective in many patients, due to the development of resistance. Several new therapeutic options for treatment of CRS have recently been proposed. One option involves a lytic enzyme produced by a bacteria infected with a bacteriophage specific for that bacteria (US 2002/0187136). The lytic enzyme may be any of the shuffled lytic enzymes, chimeric lytic enzymes, holin enzymes, or combinations thereof. A carrier may be used for delivering the lytic enzyme to the infection site. The lytic enzymes can be used for the treatment of upper respiratory infections, as well as other types of infections. However, this treatment is very time consuming, as the bacteria need to be isolated from the infection site, cultivated, infected with bacterial phages, and then the lytic enzymes must subsequently be purified from the cultures.

Another therapeutic option employs a steroidal anti-inflammatory agent. See US 2004/0209852. The steroidal agent may be used alone or in combination with an antifungal agent or an antibiotic. The therapeutic composition requires a specific particle size distribution profile and are said to be able to reduce the level of fungal organisms in a patient's mucus such that one or more of the symptoms of rhinosinusitis are prevented from developing, or are lessened, or are prevented from worsening. One disadvantage of this approach is that steroids have well known side-effects, which limits their use.

The respiratory tract employs several endogenous mechanisms to protect against microbial infections, one of which is mucociliary clearance, which removes inhaled particulate matter and microbes from the nasal cavity. Airway mucus is a complex mixture of fluid, mucin glycoproteins, and several other types of potent antimicrobial proteins and peptides, including lysozyme, lactoferrin, defensins, and others with activity against many common types of inhaled pathogens. Thus, stimulating or enhancing the secretion of the body's antimicrobial defense may be a therapeutic strategy for upper respiratory infections.

One mechanism that the human body may employ to detect the presence of bacteria and bacterial products uses bitter taste receptors of the T2R family. Bitter taste function is believed to have evolved to detect potentially harmful food components, such as poisonous plant products and bacterial fermentation products produced during spoilage of food. Bitter taste receptors were first discovered in taste cells, where they signal the presence of bitter chemicals in the oral cavity to the brain, which, in turn, directs decisions about whether to accept or reject them. It has been found that some oral taste receptors are also expressed in other organs (gut, lung, etc.) with functions less well characterized, but these may also serve to detect harmful bacterial products.

The ability to perceive certain taste compounds varies within the population. One important factor contributing to this variation is the genetics of the taste receptors, as some alleles of the taste receptors make the taste receptors less sensitive to particular taste compounds. It has been found that the inability to perceive certain taste compounds can correlate with susceptibility to respiratory infection in that subject.

Accordingly, there exists a need for improved diagnosis, prognosis and treatment of respiratory tract diseases.

SUMMARY OF THE INVENTION

In one aspect, the invention relates to a method for treating a respiratory infection by administering a composition to the respiratory tract of a subject in an amount capable of activating bitter taste signaling and/or inhibiting sweet taste signaling. The composition comprises at least a bitter receptor agonist and, optionally, a pharmaceutically acceptable carrier for delivering the composition to the respiratory tract.

In another aspect, the invention relates to a composition for treatment of a respiratory infection. Such composition comprises at least a bitter receptor agonist and, optionally, a pharmaceutically acceptable carrier for delivering the composition to the respiratory tract.

In another aspect, the invention relates to a method for determining the susceptibility of a subject to a respiratory infection by presenting a plurality of test compounds to the subject, and having the subject rate the intensity of the subject's taste response to the test compounds. The test compounds comprise at least one bitter receptor agonist and at least one non-bitter receptor agonist. The rated intensities of the taste response are then compared with pre-calibrated intensities to determine the susceptibility to a respiratory infection.

In another aspect, the invention relates to a method for determining a type of pathogen that is colonized or may be colonized in the respiratory tract of a subject. This method is carried out by presenting a plurality of test compounds to the subject, and having the subject rate the intensity of the subject's taste response to the test compounds. The test compounds comprise at least one bitter receptor agonist and at least one non-bitter receptor agonist. The rated intensities of the taste response are then compared with pre-calibrated intensities to determine a type of pathogen that is colonized or may be colonized in the respiratory tract of the subject.

In another aspect, the invention relates to a method for determining a risk of a respiratory infection associated disease or disorder in a subject, the method comprising: obtaining a biological sample from said subject; detecting the presence or absence of a polymorphism in amino acid residue positions 49, 262, and 296 of taste receptor, type 2, member 38 (T2R38), and wherein the presence or absence of said polymorphism indicates whether said subject is at the risk of said respiratory infection associated disease or disorder. The polymorphism exists between a functional allele, Proline, Alanine, and Valine (PAV) and a non-functional allele, Alanine, Valine and Isoleucine (AVI) at positions 49, 262, and 296 of said T2R38. According to the invention, the presence of homozygous PAV/PAV alleles indicates that said subject is at lower risk of said disease or disorder, relative to a subject having homozygous AVI/AVI alleles or heterozygous PAV/AVI alleles.

In another aspect, the invention relates to a method for determining a need for a surgical intervention to treat a respiratory infection associated disease or disorder in a subject, the method comprising: obtaining a biological sample from said subject; detecting the presence or absence of a polymorphism in amino acid residue positions 49, 262, and 296 of T2R38, and wherein the presence or absence of said polymorphism indicates whether said subject needs said surgical intervention to treat said respiratory infection associated disease or disorder. According to the invention, the presence of homozygous PAV/PAV alleles indicates that said subject does not need said surgical intervention to treat said respiratory infection associated disease or disorder.

In another aspect, the invention relates to a method for determining a need for a surgical intervention to treat a respiratory infection associated disease or disorder in a subject, the method comprising: conducting a bitter taste test to determine whether said subject is a taster or a non-taster; and based on the determination of said subject being a taster or a non-taster, determining whether said subject is in need of said surgical intervention to treat said respiratory infection associated disease or disorder.

In another aspect, the invention relates to a method for treating a respiratory infection associated disease or disorder in a subject, the method comprising: administering to said subject a therapeutically effective amount of a T2R38 agonist, thereby treating said respiratory infection associated disease or disorder in said subject.

In another aspect, the invention relates to a method for stimulating an innate antimicrobial response in the respiratory tract of a subject, the method comprising: administering to said subject a therapeutically effective amount of a T2R38 agonist, thereby stimulating said innate antimicrobial response in the respiratory tract of said subject.

In another aspect, the invention relates to a method for identifying a therapeutic molecule, the method comprising: screening a plurality of T2R38 agonists, and identifying a T2R38 agonist that effectively treats a respiratory infection associated disease or disorder in a subject or effectively stimulates an innate antimicrobial response in the respiratory tract of said subject.

In another aspect, the invention relates to a method for treating a respiratory infection associated disease or disorder in a subject having homozygous AVI/AVI allele or heterozygous PAV/AVI allele, the method comprising: administering to said subject a therapeutically effective amount of a taste receptor, type 2 (T2R) agonist, for example, quinine, wherein administering said T2R agonist stimulates nitric oxide (NO) production in sinonasal epithelial cells of said subject, thereby treating said respiratory infection associated disease or disorder in said subject.

In another aspect, the invention relates to a method for stimulating an innate antimicrobial response in the respiratory tract of a subject having homozygous AVI/AVI allele or heterozygous PAV/AVI allele, the method comprising: administering to said subject a therapeutically effective amount of a T2R agonist, for example, a quinine, wherein administering said T2R agonist stimulates nitric oxide (NO) production in sinonasal epithelial cells of said subject, thereby stimulating said innate antimicrobial response in the respiratory tract of said subject.

In another aspect, the invention relates to a method for treating a respiratory infection associated disease or disorder in a subject having homozygous AVI/AVI allele or heterozygous PAV/AVI allele, the method comprising: administering to said subject a therapeutically effective amount of a composition comprising *Antidesma* sp. (e.g., *Antidesma bunius*) or its extract, wherein administering said composition stimulates nitric oxide (NO) production in sinonasal epithelial cells of said subject, thereby treating said respiratory infection associated disease or disorder in said subject.

In another aspect, the invention relates to a method for stimulating an innate antimicrobial response in the respiratory tract of a subject having homozygous AVI/AVI allele or heterozygous PAV/AVI allele, the method comprising: administering to said subject a therapeutically effective amount of a composition comprising *Antidesma* sp. (e.g., *Antidesma bunius*) or its extract, wherein administering said quinine stimulates nitric oxide (NO) production in sinonasal epithelial cells of said subject, thereby stimulating said innate antimicrobial response in the respiratory tract of said subject.

In another aspect, the invention relates to a method for identifying a therapeutic molecule, the method comprising: screening a plurality of compounds in *Antidesma* sp. (e.g., *Antidesma bunius*) or its extract, and identifying a compound that effectively treats a respiratory infection associated disease or disorder in a subject or effectively stimulates an innate antimicrobial response in the respiratory tract of said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIGS. 2A and 2B show staining of β tubulin, a protein expressed in cilia on the apical membrane of the epithelial cells.

FIG. 6C also shows that this inhibition is substantially eliminated by the presence of lactisole sweet receptor antagonist.

Figure 21:
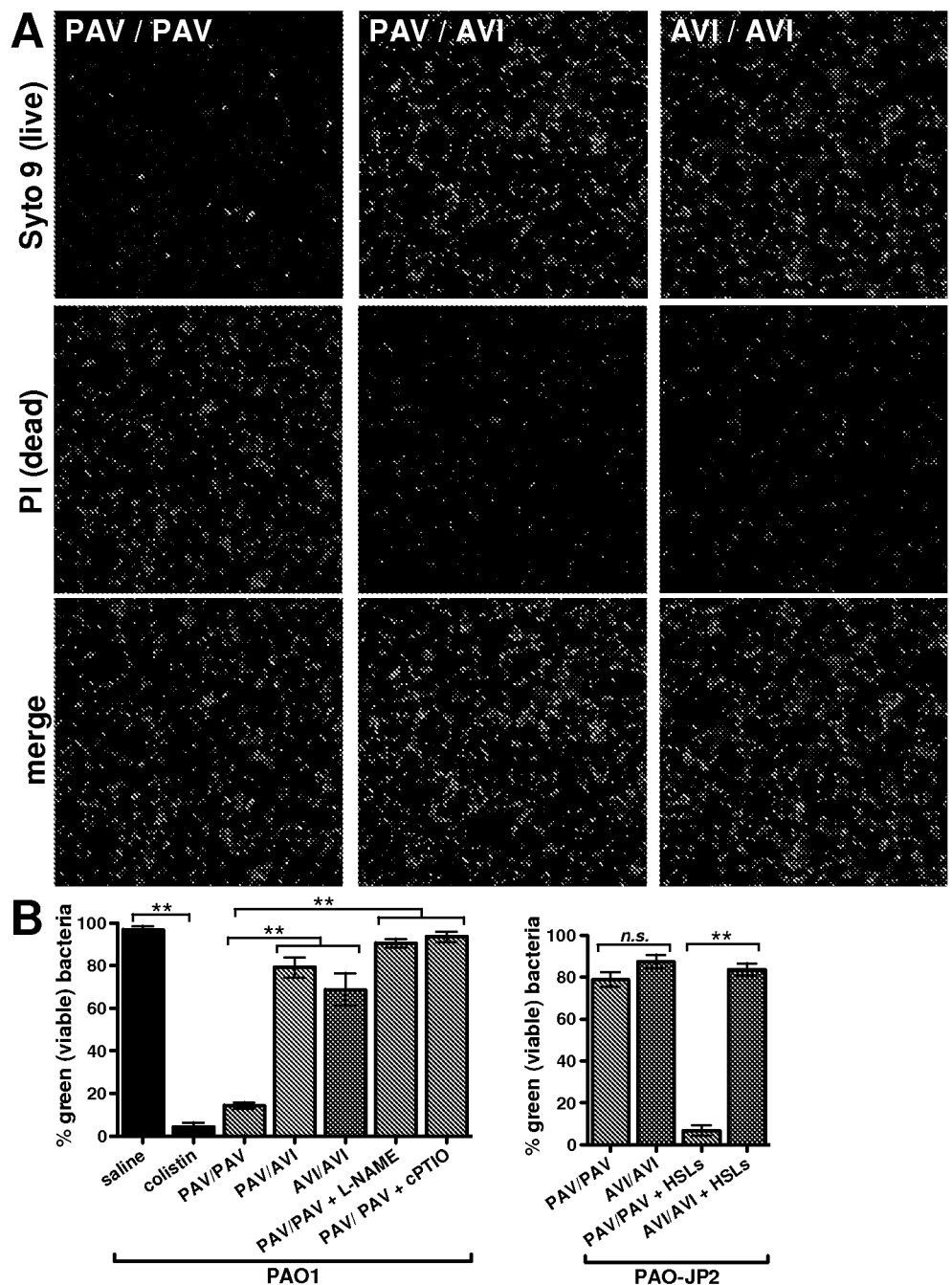

FIG. 21 shows that T2R38 is required for maximal epithelial killing of Pseudomonas aeruginosa. (A) Panels showing PAO1 removed from cultures after 2 hours exposure showing increased propidium iodide fluorescence (indicating bacterial cell permeability) and decreased Syto 9 fluorescence in bacteria exposed to PAV/PAV cultures vs PAV/AVI and AVI/AVI cultures. (B) Left bar graph shows % green (viable) PAO1 after exposure to saline (no epithelial cells; negative control; 97±2%), colistin (no epithelial cells; positive control; 4±2%), PAV/PAV cultures (14±1%), PAV/AVI cultures (80±5%), AVI/AVI cultures (70±5%), PAV/PAV cultures+L-NAME (90±2%) or cPTIO (93±2%), and washed PAV/PAV cultures (45±3%). Right bar graph shows % viable PAO-JP2 from separate experiments after exposure to PAV/PAV and AVI/AVI cultures (79±3% and 87±3%, respectively) as well as PAV/PAV and AVI/AVI cultures plus 10 μM each C4HSL and C12HSL (7±2% and 84±3%, respectively). *P<0.05, **P<0.01 (ANOVA; Bonferroni post-test).

Figure 22:
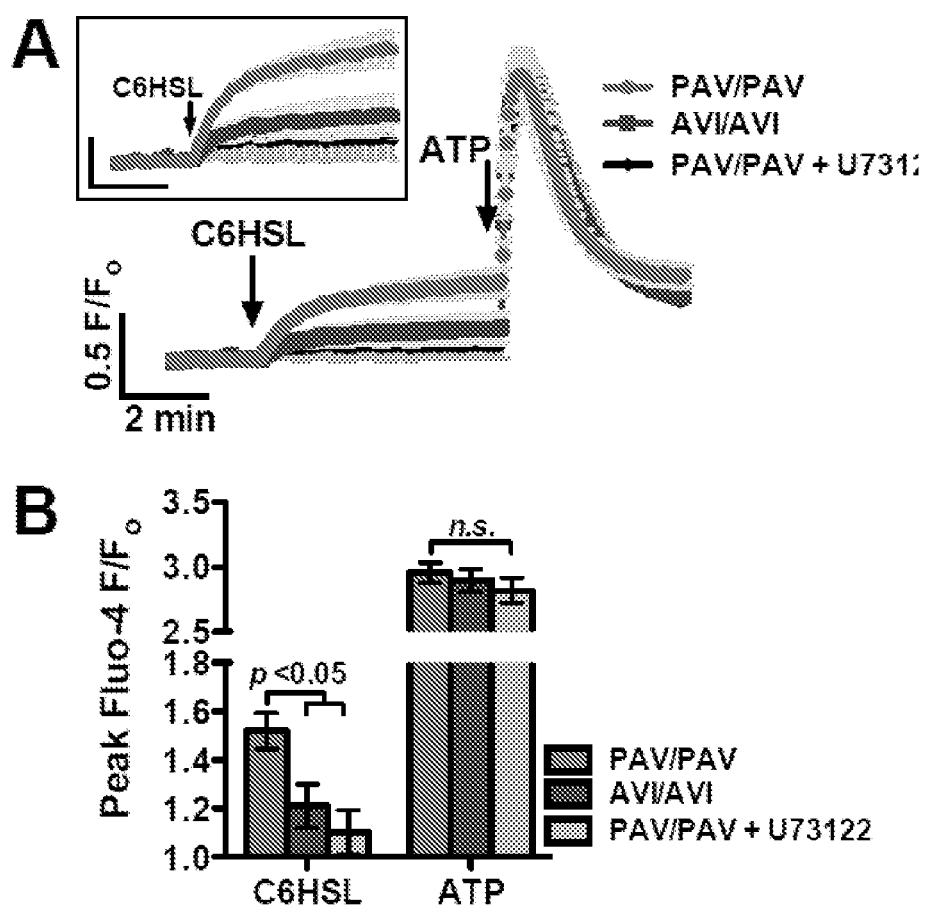

FIG. 22 shows that C6HSL (200 μM) induces T2R38- and PLCβ2-dependent Ca2+ signals. (A) Average traces from 6 PAV/PAV cultures (2 each from 3 patients), 6 AVI/AVI cultures (2 each from 3 patients), and 4 PAV/PAV cultures (1 each from 4 patients) treated with U73122. (B) Bar graph showing results from A. Average peak Fluo-4 F/Fo after 5 min stimulation with C6HSL was 1.52±0.074 (PAV/PAV), 1.10±0.09 (PAV/PAV+U73122; P<0.05 vs PAV/PAV), and 1.21±0.09 (AVI/AVI; P<0.05 vs PAV/PAV). Peak Fluo-4 F/Fo during 10 μM ATP stimulation was 2.96±0.08 (PAV/PAV), 2.82±0.1 (PAV/PAV+U73122; n.s. vs PAV/PAV), and 2.90±0.09 (AVI/AVI; n.s. vs PAV/PAV). Significance derived from 1-way ANOVA with Tukey-Kramer post-test.

Figure 23:
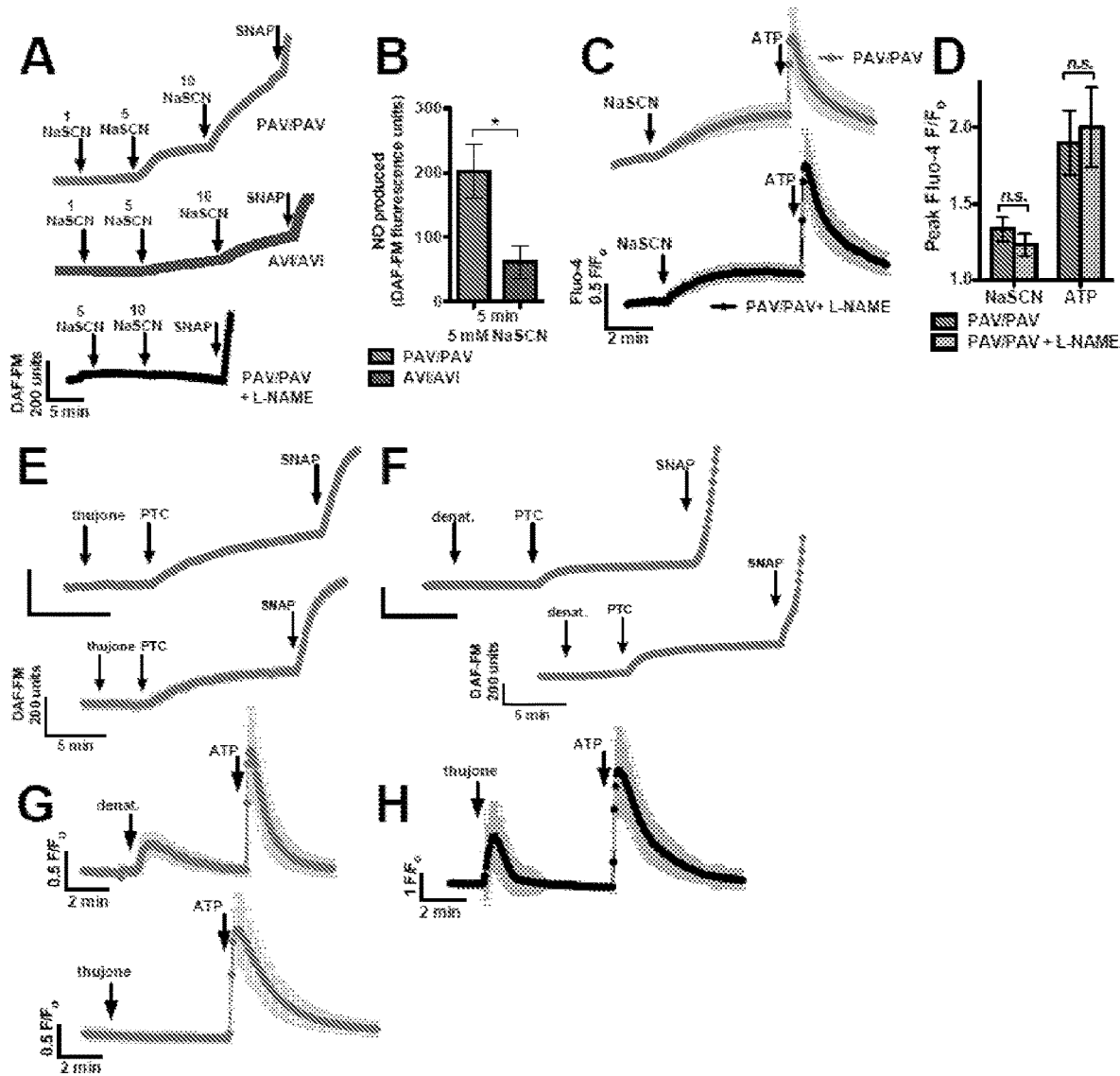

FIG. 23 shows that the T2R38 agonist sodium thiocyanate (NaSCN) activates NO generation in sinonasal ALIs, whereas 2 non-T2R38-activating bitter agonists have no effect. (A) Representative traces (each from ~100 cells from a single ALI; SEM smaller than symbol size; representative of 6 experiments each) of DAF-FM response to NaSCN. (B) Bar graph showing NO production in tasters and non-tasters (n=3 pts [2 cultures each] for each genotype). When averaged by patient, DAF-FM fluorescence increase after 5 min NaSCN was 202±38 units (PAV/PAV) vs 61±23 units (AVI/AVI; P=0.016 by Student's t-test; *P <0.05) (C) Representative traces showing Ca2+ responses to NaSCN and ATP in the presence (black) or absence (blue; control) of L-NAME (50 μM). (D) After stimulation with 5 mM NaSCN, F/Fo was increased to 1.33±0.08 (control) and 1.24±0.07 (+L-NAME; n.s. by Student's t-test). Peak F/Fo during stimulation with 1 μM ATP was 1.9±0.21 (control) and 2.0±0.26 (L-NAME; n.s. by Student's t-test). L-NAME had no significant effect on Ca2+ signaling at the concentration used, thus L-NAME block of DAF-FM fluorescence increase likely reflects inhibition of NOS. (E-F) Neither the T2R10 and T2R14 specific agonist thujone (5 mM) nor the T2R4, T2R8, T2R10, T2R13, T2R39, T2R43, T2R46, and T2R47-specific agonist denatonium benzoate (10 mM) had any effect on NO production. Shown are 2 representative traces for each agonist from 2 cultures from different PAV/PAV patients (4 patients tested). (G) Ca2+ responses to denatonium but not thujone were observed in sinonasal ALI cultures. (H) As a control for thujone activity, Ca2+ responses to thujone were observed in human bronchial epithelial (HBE) cells.

Figure 24:
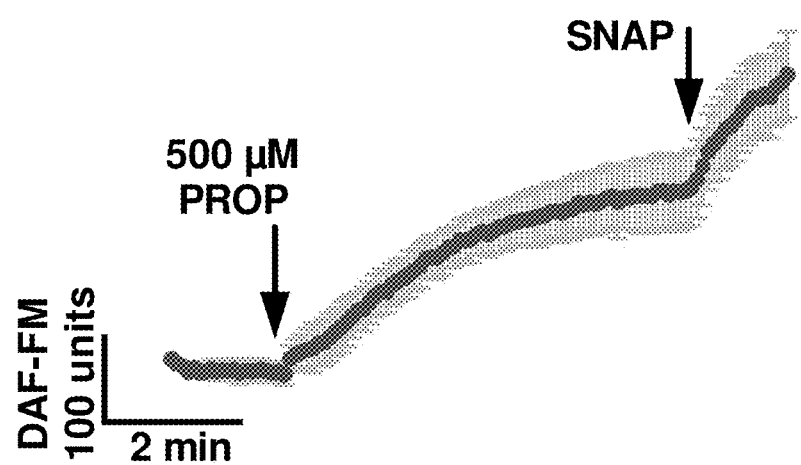

FIG. 24. The T2R38 agonist PROP activates nitric oxide (NO) production in PAV/PAV (taster) sinonasal epithelial cells. As with other T2R38 agonists, apical application of the T2R38-specific bitter compound 6-n-propylthio uracil (PTU or PROP) stimulated an increase in intracellular DAF-FM fluorescence (signaling increased nitric oxide and reactive nitrogen species production) in sinonasal epithelial cells as observed with PTC and NaSCN. Given the clinical experience with PROP (when given systemically), it may be a preferred therapeutic T2R38 stimulating compound for use in a topical therapeutic sinus lavage and/or spray. NO production during stimulation with the non-specific NO donor S-nitroso-N-acetylpenicillamine (SNAP) is shown as a control.

Figure 25:
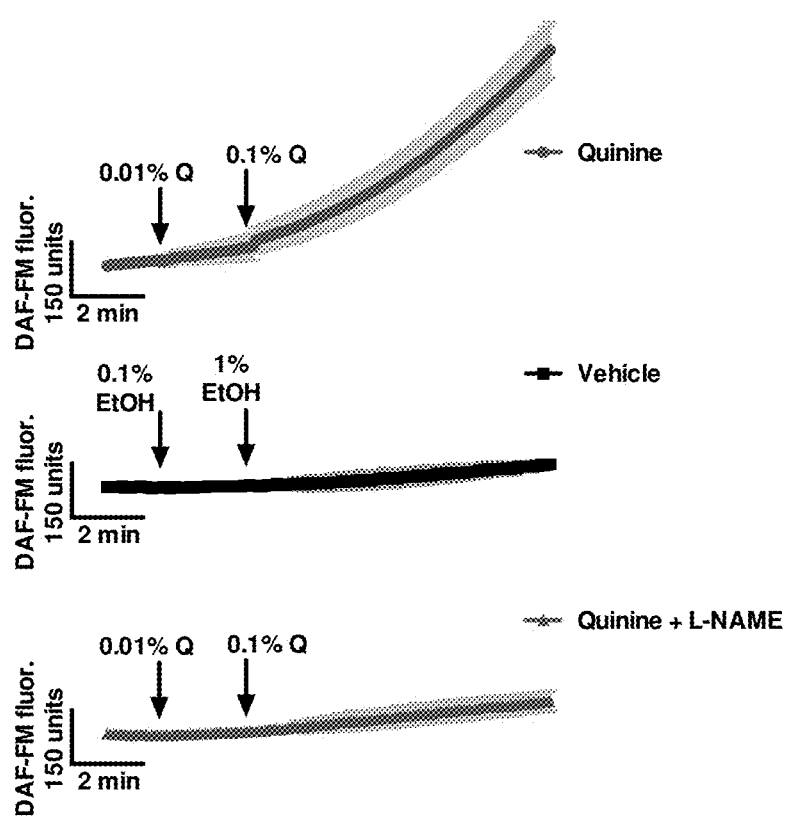

FIG. 25. The bitter agonist quinine stimulates nitric oxide (NO) production in PAV/AVI heterozygote sinonasal epithelial cells. Apical application of quinine (but not vehicle alone) stimulated a robust NO production (evidenced by increase in DAF-FM fluorescence) that was inhibited by the nitric oxide synthase (NOS) inhibitor L-NAME (20 μM). Because quinine is not a T2R38 activator, quinine can be a useful therapeutic because it can stimulate NO production in T2R38 non-tasters and heterozygotes (AVI/AVI and PAV/AVI) by activating other bitter receptors and bypassing the requirement for T2R38.

DETAILED DESCRIPTION OF THE INVENTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", and "having" can also be used interchangeably.

In a first aspect, the present invention is directed to methods of treating infections of the respiratory tract, especially the upper respiratory tract, using a composition including at least one bitter taste receptor agonist, or sweet receptor antagonist, or combination of both.

Figure 1:
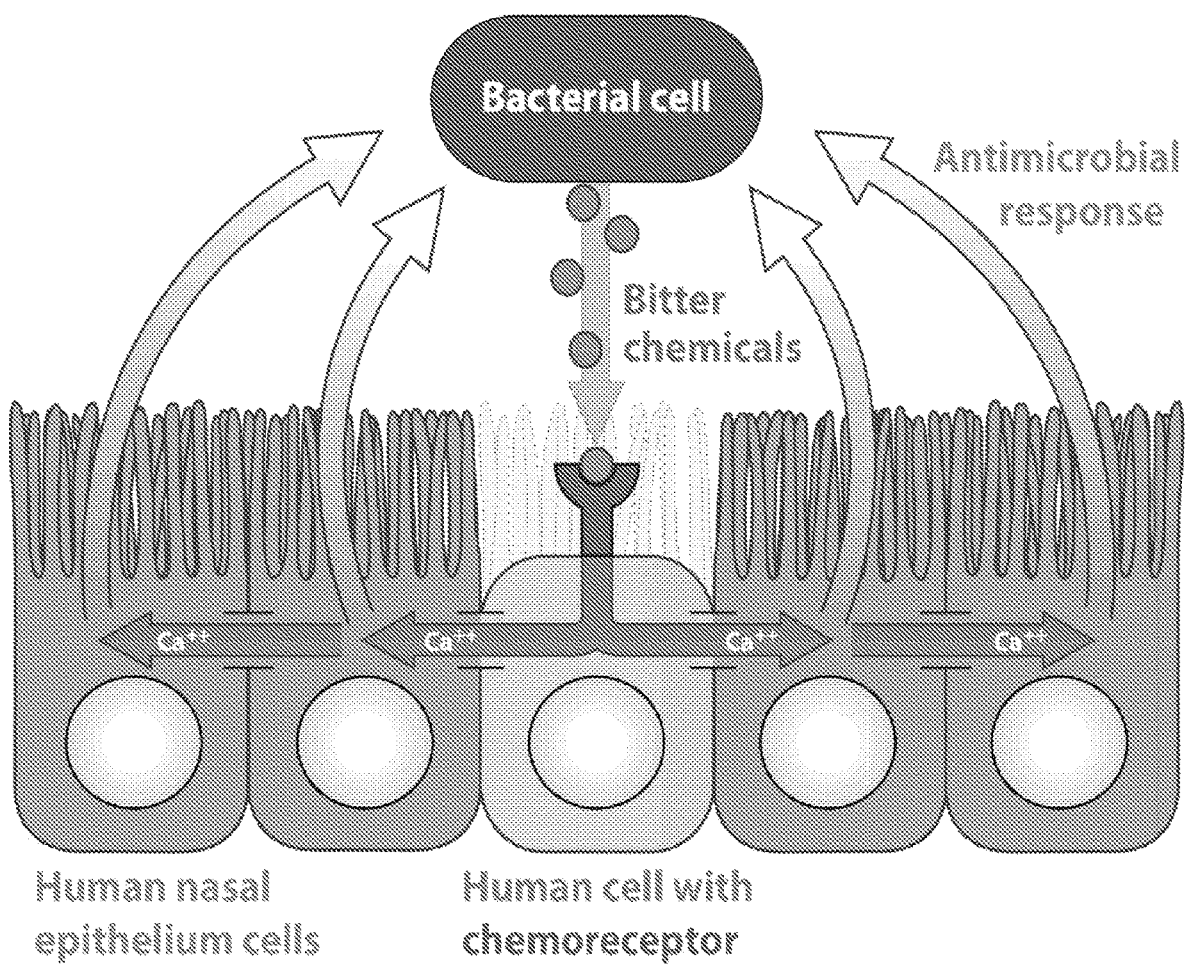
FIG. 1 schematically depicts a mechanism for an innate response to the presence of bacteria in the nasal passages.

As shown in FIG. 1, bacteria secrete bitter compounds, which may stimulate bitter taste receptors in nasal epithelial cells which, in turn, propagate a signaling cascade to the body causing the nasal epithelial cells to launch an antimicrobial attack. The present invention employs at least one bitter taste receptor agonist to stimulate bitter taste receptors in nasal epithelial cells thereby causing propagation of a signaling cascade to the body. This will cause the nasal epithelial cells to release one or more antimicrobials thereby enhancing the resistance to microbes in the respiratory tract.

Figure 2:
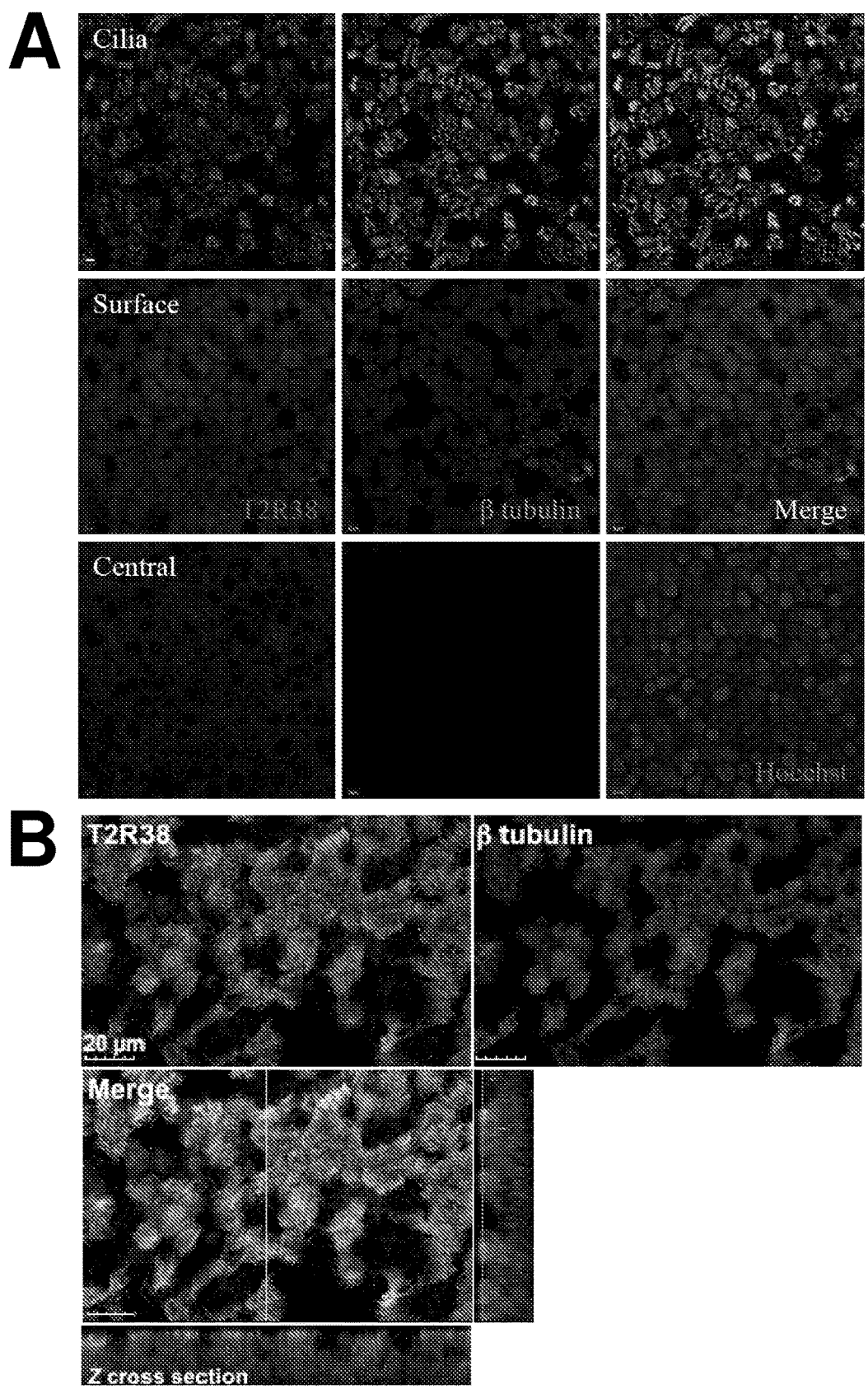
FIG. 2A shows the T2R38 expression by immunofluorescence microscopy at different locations in a single human sinonasal epithelial cell culture.
FIG. 2B shows T2R38 immunofluorescence in a human sinus tissue explant. Both

The bitter taste receptor T2R38 is expressed in sinonasal epithelial cultures (FIG. 2A; representative of 6 subjects examined). High expression is observed in the apical membrane, with beta-tubulin (a marker for cilia) as shown in green in FIG. 2A. Expression is also found at the surface of nonciliated cells of the sinonasal cavity, while at the central region, the T2R38 has only minimal level of expression. The T2R38 expression in sinonasal epithelial cell cultures mimics the T2R38 expression observed in explanted tissue from human sinus, as shown in FIG. 2B (beta-tubulin shown in red, T2R38 shown in green).

Figures 3A, 3B:
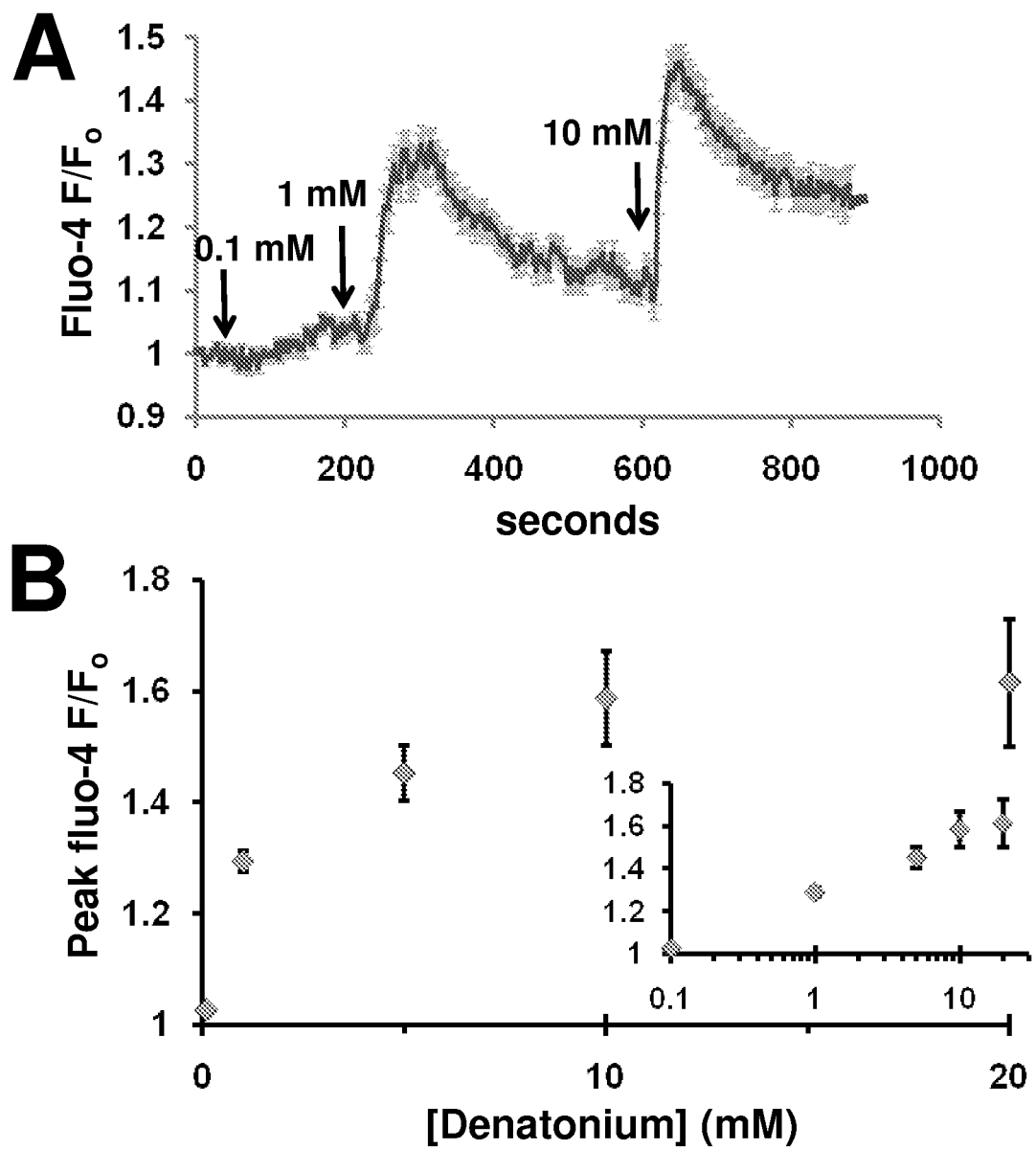
FIG. 3A shows elevation of fluo-4 fluorescence signals immediately following stimulation of nasal epithelial cells with denatonium at different concentrations. The fluorescence signal correlates to the calcium concentration measured in the treated nasal epithelial cell air-liquid interface (ALI) cultures.
FIG. 3B is a dose-response plot of peak fluorescence elevation in response to stimulation of nasal epithelial cells with concentrations of 0.1 mM, 1 mM, 5 mM, 10 mM, and 20 mM of denatonium.

Bitter taste signaling serves the function of indicating the presence of bacteria in the upper respiratory tract and activating a response during times of bacterial infection, in addition to the function of detecting the taste of material entered the mouth or nose. The first response to a bitter taste is a signal causing elevation of $[Ca^{2+}]$ in the epithelial cells of the upper respiratory tract. When a bitter taste receptor is activated with a bitter receptor agonist, such as denatonium benzoate or PTC, the intracellular calcium concentration $[Ca^{2+}]$ is elevated as shown in FIG. 3A, which may also lead to an increased ciliary beat frequency (CBF). For example, the bitter agonist absinthin may activate CBF.

Figures 6A, 6B, 6C:
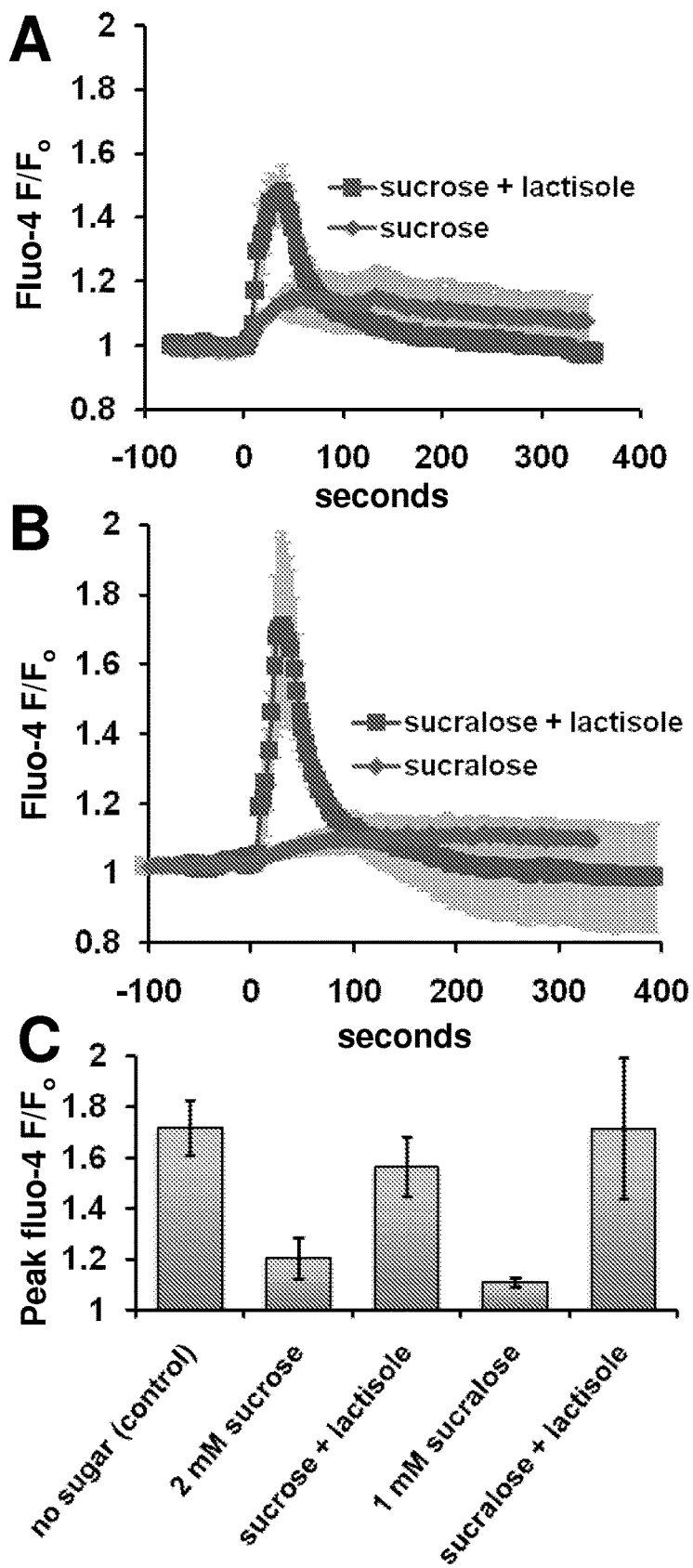
FIG. 6A shows that sucrose inhibits denatonium induced calcium signaling in nasal epithelial cell cultures, and that the additional presence of lactisole sweet receptor antagonist substantially eliminates the inhibition of the calcium signaling caused by the sucrose. Denatonium was added at time zero.
FIG. 6B shows that sucralose inhibits denatonium induced calcium signaling in nasal epithelial cell cultures, and that the additional presence of lactisole sweet receptor antagonist substantially eliminates the inhibition of the calcium signaling caused by the sucralose. Denatonium was added at time zero.
FIG. 6C shows the maximal inhibition of denatonium induced calcium signaling in nasal epithelial cell culture caused by 2 mM sucrose or 1 mM sucralose.

The denatonium benzoate induced elevation of $[Ca^{2+}]$ in epithelial cells has been found to be significantly repressed by the presence of sweet receptor antagonists, such as glucose, sucrose or sucralose, on the apical surface. For example, when a sweet receptor is activated with, for example, sucrose or sucralose, addition of denatonium to the nasal epithelial cell culture caused little increase in calcium signaling (see e.g. FIGS. 6A-6B). This problem can be solved by the further inclusion of a sweet taste receptor antagonist, such as lactisole, to reduce, prevent or reverse the inhibition caused by sweet receptor antagonists as shown in FIGS. 6A-6B. This demonstrates that the inhibition of the reduced effect of denatonium treatment on calcium signaling in the presence of sucrose or sucralose is caused by activation of the sweet receptor (see, e.g., FIG. 6C).

Because sweet compounds such as glucose may be present at a higher concentration in the nasal secretions of subjects with respiratory infections (FIG. 4C), a sweet taste receptor antagonist could reduce inhibition of the effect of the bitter receptor agonist by the sweet taste receptor antagonist. As describe below, lactisole can also reverse the glucose repression on the bacterial kill effect, as shown in FIG. 4B.

The second response caused by bitter taste signaling activation in epithelial cells, in addition to $[Ca^{2+}]$ elevation, is secretion of antimicrobial products, which is part of an innate immune reaction. The antimicrobial products include many peptides, including lysozyme, lactoferrin and defensins, that exhibit activity in suppression or killing of microbes, for example, *Hemophilus influenza, Pseudomonas aerginosa, Staphylococcus aureus, Streptococcus pneumoniae, Streptococcus fasciae, Listeria, Salmonella, E. coli, Campylobacter, Helicobacter pylori, Streptococcus mutans,* and *Mycobacterium tuberculosis.*

Bitter taste receptor agonists denatonium and absinthin can stimulate antimicrobial activity in sinonasal cell cultures to kill both *Pseudomonas aeruginosa* and MRSA (FIG. 4A-B and FIG. 5) as well as *Kleibsiella pneumoniae.* Airway surface liquid (ASL) from nasal cultures treated with 10 mM denatonium or 300 µM absinthin show significant bactericidal effects against both *Pseudomonas aeruginosa*, MRSA, as well as *Kleibsiella pneumoniae.*

Figure 7:
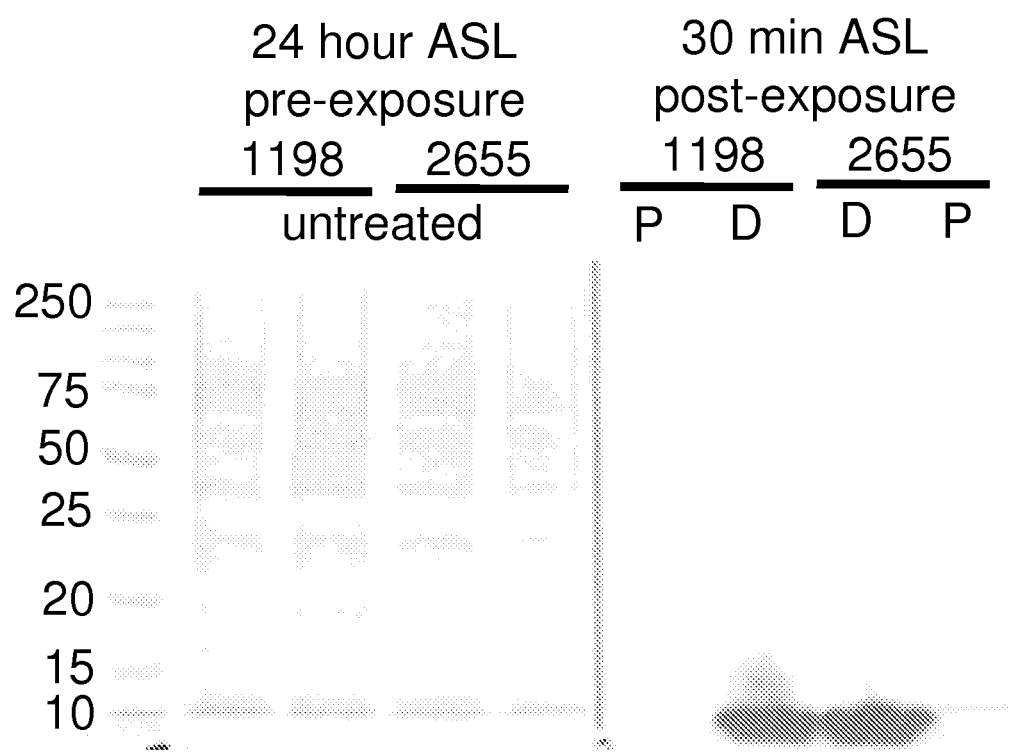
FIG. 7 shows that denatonium stimulated nasal epithelial cell cultures secrete low molecular weight proteins into the ASL. The ASL in the left panel was obtained from four cultures derived from 2 patients (1198 and 2655) and was collected before any treatment. The ASL in the right panel was obtained from the same four cultures after 30 minutes of treatment with denatonium benzoate (10 mM) in PBS (D) or PBS alone (P).

The antimicrobial product stimulated by denatonium is proteinaceous. When the nasal epithelial cell cultures are stimulated with denatonium, within 30 minutes, low molecular weight proteins are secreted into the surface liquid as shown in FIG. 7. In comparison, these proteins are missing or present only at very low levels before the denatonium treatment, or if the nasal epithelial cell cultures are only treated with the control PBS buffer as also shown in FIG. 7.

Figure 8:
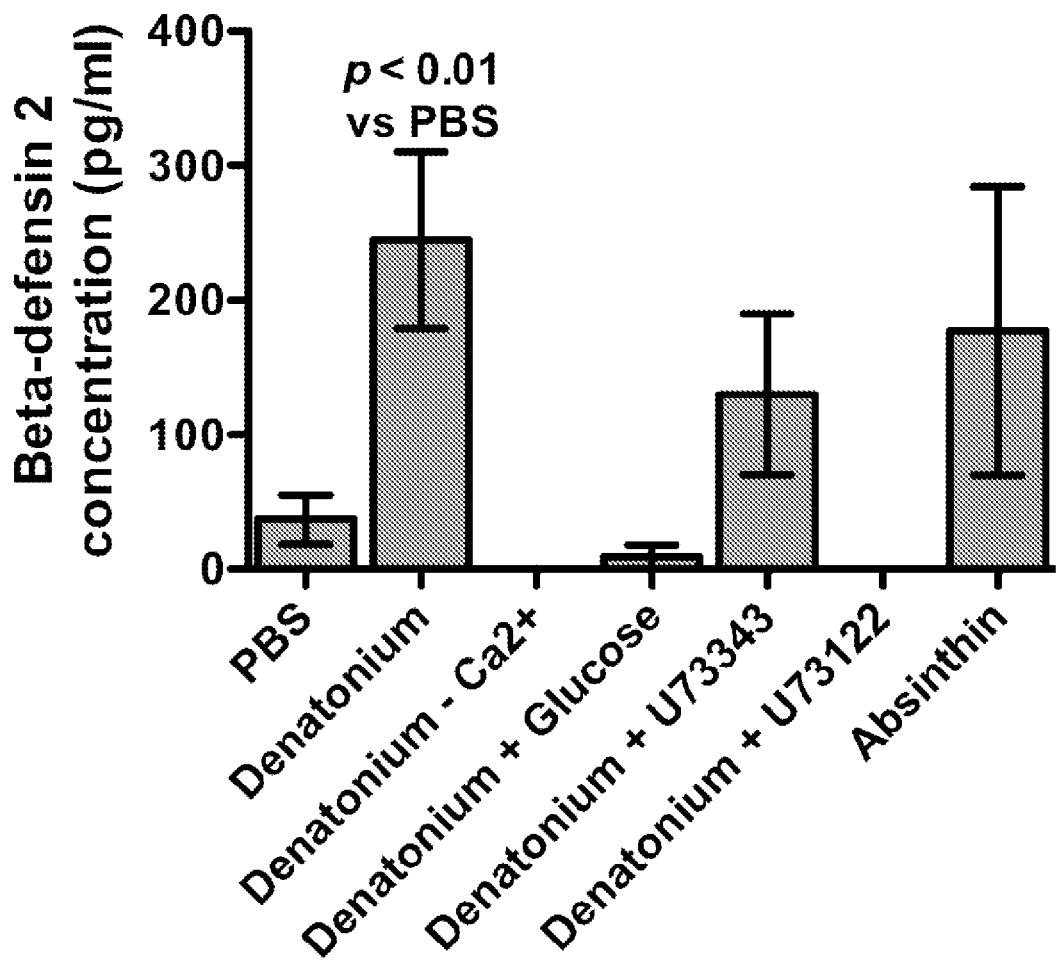
FIG. 8 shows that bitter taste agonists denatonium and absinthin stimulate beta-defensin 2 secretion under various conditions.
Figures 9A, 9B, 9C, 9D:
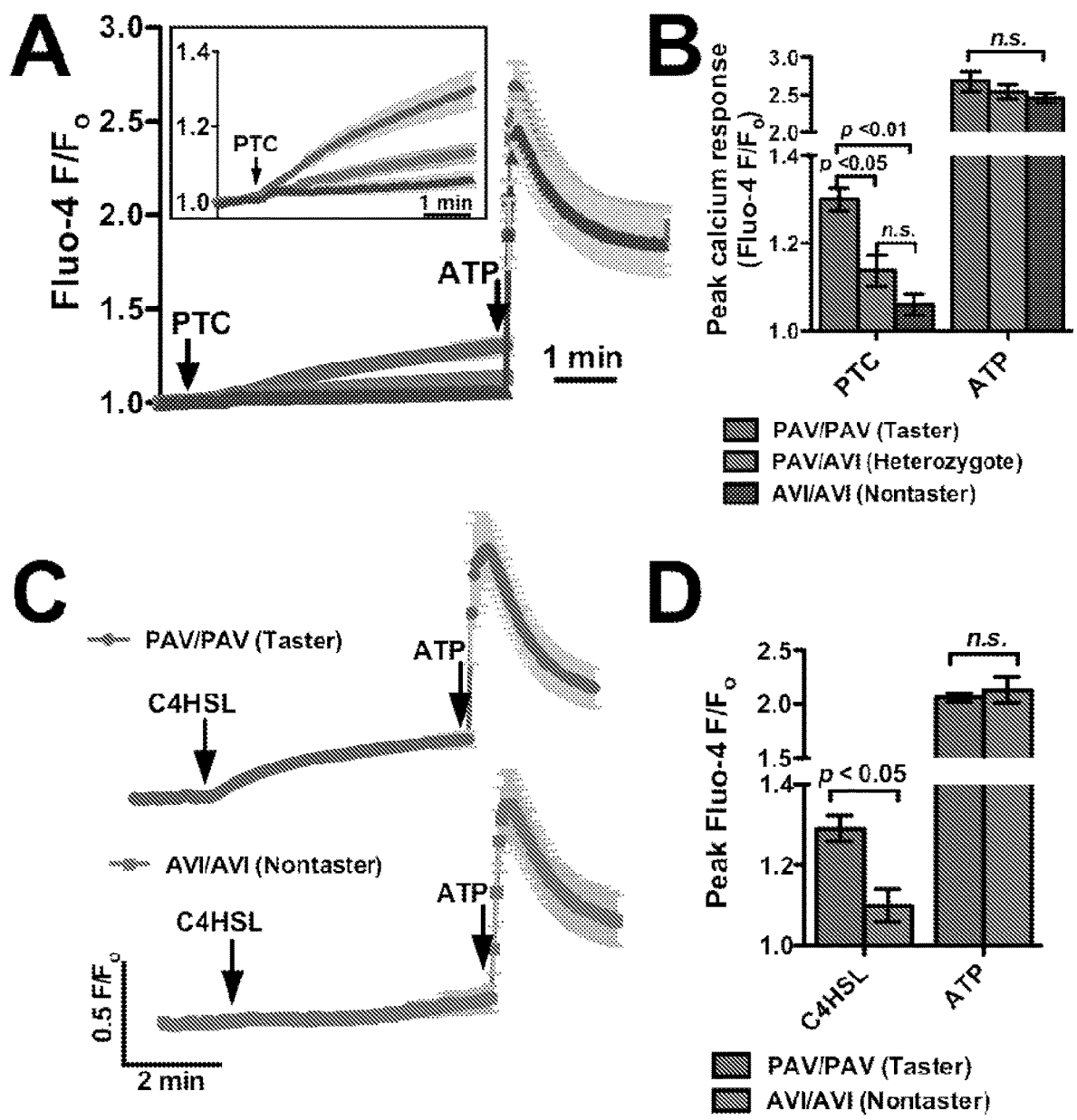
FIG. 9A shows bitter taste receptor T2R38 agonist phenylthiocarbamide (PTC) stimulated fluo-4 fluorescence and ATP-evoked fluo-4 fluorescence in sinonasal cultures from patients with different T2R38 genotypes.
FIG. 9B shows PTC-induced fluo-4 fluorescence increase after 5 minutes of stimulation as well as peak ATP-induced fluorescence increase in sinonasal cultures from patients with different T2R38 genotypes.
FIG. 9C shows butyryl-homoserine lactone (C4HSL; a secreted bacterial product)-stimulated fluo-4 fluorescence increases and ATP-evoked fluo-4 fluorescence increases in sinonasal cultures from patients with different T2R38 genotypes.
FIG. 9D shows C4HSL-induced fluo-4 fluorescence increase after 5 minutes of stimulation as well as peak ATP-induced fluorescence increase in sinonasal cultures from patients with different T2R38 genotypes.

One of these low molecular weight proteins is the well-characterized antimicrobial peptide beta-defensin 2, which is induced with denatonium or absinthin (FIG. 8). Beta-defensin secretion may be blocked in cultures with the absence of calcium or in the presence of glucose or the presence of the PLCbeta2 inhibitor U73122. The inactive analogue of U73122, U73343) had no effect.

Figure 10A:
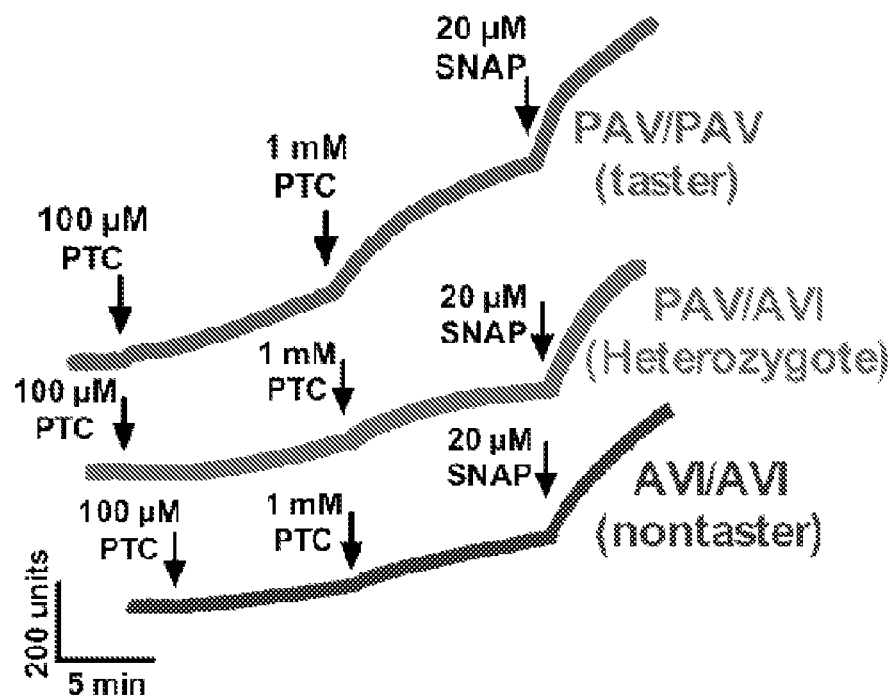
FIG. 10A shows representative traces of DAF-FM fluorescence increases (reflecting NO production) in patients with different T2R38 genotypes
Figure 10B:
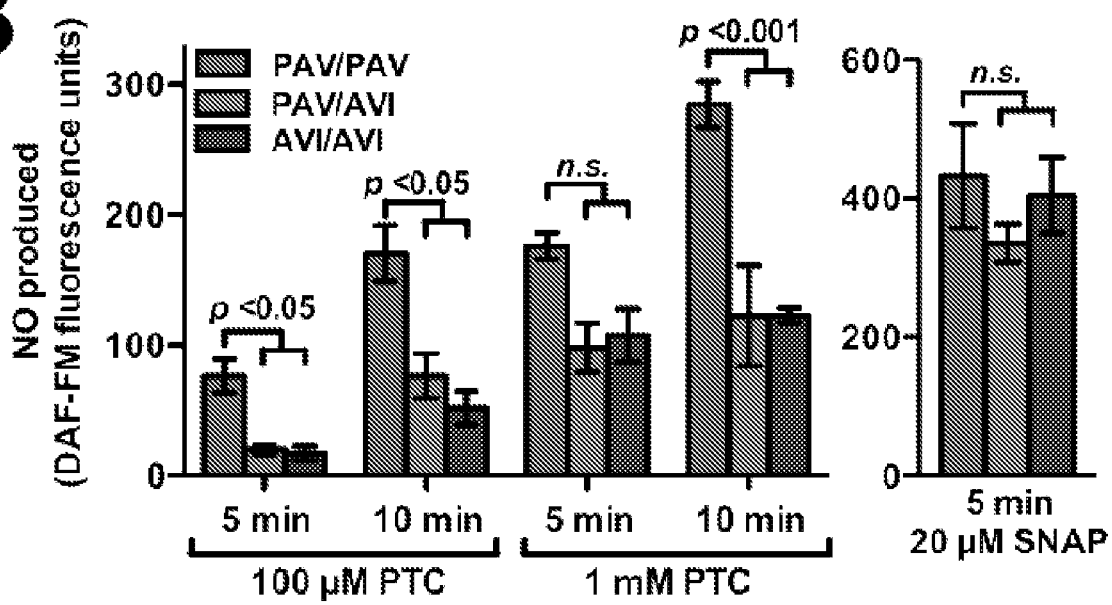
FIG. 10B shows PTC-induced nitric oxide (NO) production in sinonasal cultures from patients with different T2R38 genotypes.

Yet another effect of bitter taste signaling activation is nitric oxide (NO) production, as shown in FIG. 10. NO production was measured by recording fluorescence of nasal cultures loaded with the NO-sensitive dye 4-amino-5-methylamino-2',7'-difluorescein (DAF-FM). DAF-FM fluorescence increase (reflecting NO production) in response to PTC stimulation correlated with T2R38 genotype. T2R38 has 2 common polymorphisms based at 3 locations in the protein, A49P, V262A, and I296V (rs713598, rs1726866 and rs10246939). PAV alleles are functional, while AVI alleles are nonfunctional. As a control, fluorescence increases in response to the non-specific NO donor S-Nitroso-N-Acetyl-D,L-Penicillamine (SNAP) were not significantly different.

Therefore, interference with certain components of the taste signaling pathways, i.e. activating bitter taste signaling and/or inhibiting sweet taste signaling, can be used to activate an immediate and vigorous innate antimicrobial response in the upper respiratory tract. Any components that activate bitter taste signaling or inhibit sweet taste signaling and thereby enhancing the innate antimicrobial response may be employed in the present invention. In preferred embodiments, the activation of bitter taste signaling is through the use of bitter taste receptor agonists, and the inhibition of sweet taste signaling is through the use of sweet taste receptor antagonists.

Using compounds targeted to downstream products of these two signaling cascades may also achieve similar effects. Downstream products of interest may include the TrpM5 ion channel, phospholipase C isoform β2, and the Gα protein α-gustducin, which are expressed in epithelial cells in the upper respiratory tract, especially the nasal cavity. The taste signaling cascades are discussed in detail in Kinnamon, S. C., Taste receptor signaling from tongues to lungs, *Acta Physiology* (Oxf), 2011, which is incorporated into this application by reference in its entirety.

Activation of bitter taste signaling is preferably accomplished by activating a plurality of bitter taste receptors. There are twenty-five known bitter taste receptors that belong to the T2R family. Different bitter taste receptors may have different affinities for the same agonist. Therefore, the use of bitter taste receptor agonists to activate bitter taste signaling will have varying degrees of activity depending upon which bitter taste receptors the agonist may bind to.

In an exemplary embodiment, the bitter taste receptor agonist denatonium, which activates eight of the twenty-five bitter taste receptors, is effective in inducing the antimicrobial activity from the epithelial cells in the upper respiratory tract. The bitter taste receptors important for antimicrobial peptide secretion are, for example, T2R10, T2R46, and/or T2R47 (recently renamed to T2R30). They are the receptors for both denatonium and absinthin. Amarogentin activates T2R46 and 47, and thujone activates T2R10. In one embodiment, multiple bitter taste receptors are activated to induce bacterial killing. Additional compounds that target bitter taste receptors may be found in Meyerhof, et al. (Chem. Senses. 2010; 35(2):157-70, "The molecular receptive ranges of human TAS2R bitter taste receptors"), which is incorporated by reference in its entirety. In one embodiment, the bitter taste receptors T2R10, T2R46, and T2R47 are activated by agonists to treat respiratory infections.

In another aspect, bitter taste receptor agonists may need to pass a minimum threshold of bitterness to sufficiently activate bitter taste signaling to achieve the desired level of anti-microbial response. Bitter taste receptor agonists such as denatonium and absinthin that are extremely bitter, are effective in inducing the antimicrobial activity.

In one exemplary embodiment, a homoserine lactone may be used to activate the bitter taste signaling pathway to induce antibacterial activity in the respiratory tract. Examples of a homoserine include, but are not limited to, butyryl-homoserine lactone (C4HSL), n-hexanoyl-l-homoserine lactone (C6HSL), and n-dodecanoyl-l-homoserine lactone (C12HSL).

Any suitable bitter taste receptor agonist or a molecule that activates the bitter taste signaling pathway, known to one of skilled in the art, can be used. Examples of such agonist or molecule include, but are not limited to, denatonium, absinthin, phenylthiocarbamide (PTC), a homoserine lactone, sodium thiocyanate (NaSCN), and 6-n-propylthio uracil (PROP or PTU). In some embodiments, a quinine that stimulates nitric oxide (NO) production in sinonasal epithelial cells can be used an agent to activate the signal pathway. In other embodiments, an extract or a compound from *Antidesma* sp. (e.g., *Antidesma bunius*) fruits or other parts can be used an agent to activate the signal pathway. The extract or compound from *Antidesma* sp. may stimulate NO production in sinonasal epithelial cells.

Inhibition of sweet taste signaling is preferably accomplished by administration of a sweet taste receptor antagonist. The sweet taste receptor is, for example, a heterodimer comprising 2 subunits of the T1R family (T1R2 and T1R3). Sweet taste signaling is consistently activated by the glucose present in the airway surface liquid and mucus of subjects with upper respiratory infections, which may suppress the innate antimicrobial immunity of the upper respiratory tract. The use of sweet receptor antagonists to block the effect of glucose or other sweet materials (e.g., bacterial glycoproteins) that may be present in the respiratory tract is another aspect of present invention. The inhibition of sweet taste signaling removes the suppression of the innate antimicrobial immune response and thereby enhances the antimicrobial response that triggered by activation of a bitter taste receptor. Sweet taste receptor antagonists suitable for use in the present invention include natural plant products such as lactisole, gymnemic acids, hodulcine, and ziziphin.

In exemplary embodiments, the sweet taste receptor antagonist may be the only active ingredient in a therapy for respiratory infections. Such a therapy can reduce the blocking effect of glucose that may be present in the respiratory tract and thereby enhance the innate antimicrobial response caused by bitter test receptor agonists secreted by bacteria. This may prove to be advantageous in certain circumstances where subjects are more agreeable to using a sweet taste receptor antagonist because it would not taste bitter if inadvertently gotten into the mouth.

The compositions of the invention are preferably formulated with a pharmaceutically acceptable carrier. Preferred compositions are topical compositions and thus preferred carriers are pharmaceutically acceptable topical carriers.

The compositions may be applied to the respiratory tract, preferably to the upper respiratory tract through any direct or indirect means. Direct means include nasal sprays, nasal drops, nasal ointments, nasal washes, nasal lavage, nasal packing, bronchial sprays and inhalers, or any combination of these and similar methods of application. Indirect means include use of throat lozenges, mouthwashes or gargles, or use of ointments applied to the nasal nares, the bridge of the nose, or any combination of these and similar methods of application.

Depending on the desired method of application, the composition may have different viscosity requirements. In one embodiment, the composition has a viscosity sufficiently high to ensure that the composition may adhere to the respiratory tract for a sufficient time to induce the antimicrobial activity. In other words, once the composition is applied to the respiratory tract, the composition does not easily flow in the tract because due to the relatively high viscosity.

In other embodiments, it may be desirable for the composition to have a relatively low viscosity. For example, when the desired method of application is nasal lavage, the composition is typically applied to the nasal cavity in relatively large quantity. The lavage has two functions: one is washing out the mucus and glucose from the upper respiratory tract, and another is providing an active ingredient to induce the antimicrobial activity. Thus, to accomplish both functions of a nasal lavage, it may be desirable to have a relatively low viscosity formulation. One preferred embodiment uses a bitter agonist (denatonium or absinthin)-eluting sinus stent as a semi-rigid formulation.

In an exemplary embodiment, the composition is suitable for use as an endoscopically guided instillation by a treating physician into at least one sinus, for the purpose of treating infections, especially those located deep in the sinus. This may be extended to the lower airways with delivery by a treating physician to a lobe or segment of a lung via a bronchoscope. In other embodiments, the composition may be atomized and sprayed into the respiratory tract, and preferably, the upper respiratory tract. Atomization allows the fine liquid droplets to reach deep into the sinus and other parts of the respiratory tract.

The antimicrobial activity induced by the compositions of the invention is believed to be provided by peptides, secretion of which may leave the epithelial cells temporarily vulnerable, as the reservoir of the antimicrobial peptides will need to be replenished by the cells over time. Sufficient time may be needed between two consecutive doses to ensure that the second dose to be effective, i.e. that the cells have sufficiently replenished the antimicrobial peptides to release additional peptides responsive to the second dose. In one preferred embodiment, the composition is used no more frequently than once every three days. More preferably, the composition is used as a weekly treatment.

Figure 4A:
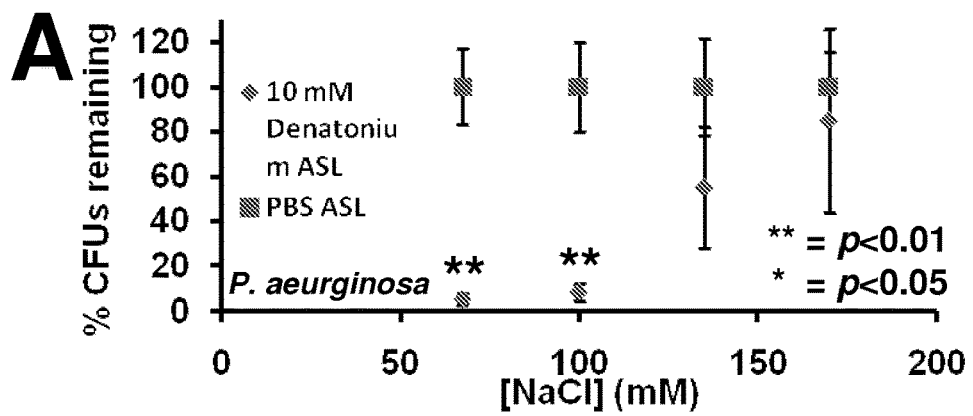
FIG. 4A shows the salt-dependent results of treatment of *P. aeurginosa* with apical surface liquid (ASL) samples from denatonium-treated ALI cultures.
Figure 4B:
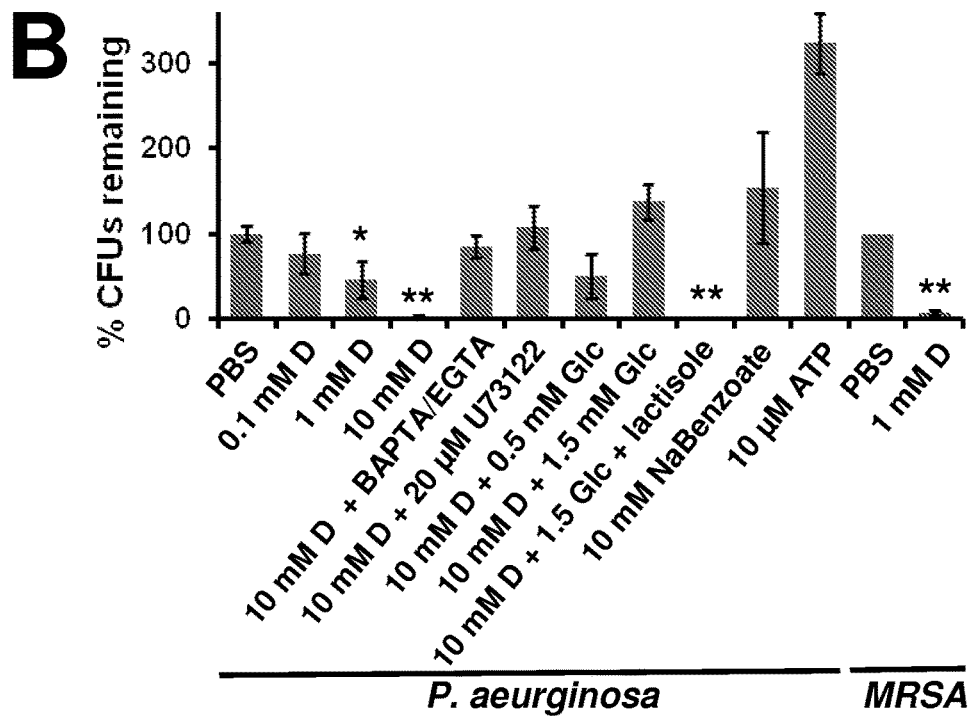
FIG. 4B shows the results of treatment of *Pseudomonas* and Methicillin-resistant *Staphylococcus aureus* (MRSA) with a variety of different samples from treated ALI cultures.

The innate antimicrobial activity is sensitive to salt as shown in FIG. 4A, presumably because the anti-microbial peptides such as lysozyme, lactoferrin, cathelicidin, and beta-defensins are tonically secreted into the respiratory tract. As a result, the antimicrobial activity of these peptides may be sensitive to ionic strength (which accounts for charge). The composition of present invention is preferably formulated with low strength of ions. The ionic strength may be up to about ~306 mEq/L, the same ionic strength as found in interstitial fluid. The preferred ionic strength is around 50% of PBS (about 150 mEq/L of ions). The preferred range of ionic strength is about 150-200 mEq/L.

The ionic strength in the formulation may vary with the delivery system. A higher volume delivery system (Netti Pot) would allow for a solution closer to the optimal ionic strength range (150-200 mEq/L) because the effects of mixing with mucus would be minimal. A lower volume delivery system may require an even lower ionic strength in the therapeutic solution. In one embodiment, the composition is formulated so that the final ionic strength after the application to the upper respiratory tract is preferably within the range of 150-200 mEq/L.

In general, the composition of the present invention can be in the form of a solid, liquid, and/or aerosol including, without limitation, powders, crystalline substances, gels, pastes, ointments, salves, creams, solutions, suspensions, partial liquids, liquid suspensions, sprays, nebulae, mists, atomized vapors and tinctures.

Any device can be used to administer the composition of present invention including, but not limited to, bulbs, inhalers, canisters, sprayers, nebulizers, and masks. In one embodiment, the composition is packaged in conventional spray administration containers, provided that the container material is compatible with the formulation. In a preferred embodiment, the composition of the present invention is packaged in a container suitable for dispersing the composition as a mist directly into each nostril. For example, the container may be made of flexible plastic such that squeezing the container impels a mist out through a nozzle into the nasal cavity. Alternatively, a small pump may pump air into the container and cause the liquid spray to be emitted.

In an alternative embodiment, the composition of the present invention is packaged in a container pressurized with a gas which is inert to the user and to the ingredients of the composition. The gas may be dissolved under pressure in the container or may be generated by dissolution or reaction of a solid material which forms the gas as a product of dissolution or as a reaction product. Suitable inert gases which can be used include nitrogen, argon, and carbon dioxide.

Also, in other embodiments, the composition may be packaged in a pressurized container with a liquid propellant such as dichlorodifluoromethane, chlorotrifluoro ethylene, or some other conventional propellant.

Preferably, the composition of present invention is packaged in a metered dose spray pump, or metering atomizing pump, such that each actuation of the pump delivers a fixed volume of the formulation (i.e. per spray-unit).

For administration in a dropwise manner, the composition of present invention may suitably be packaged in a container provided with a conventional dropper/closure device, comprising a pipette or the like, preferably also delivering a substantially fixed volume of the formulation.

The compositions of the present invention may comprise one or more additional conventional components selected from thickeners, preservatives, emulsifiers, coloring agents, plasticizers and solvents.

Thickeners that may be used to adjust the viscosity of the composition, include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B. F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). Other preferred gelling polymers include hydroxyethylcellulose, cellulose gum, MVE/MA decadiene crosspolymer, PVM/MA copolymer, or a combination thereof.

Preservatives may also be used in the compositions of the present invention and preferably comprise about 0.05% to 0.5% by weight of the composition. The use of preservatives assures that if the product is microbially contaminated, the formulation will prevent or diminish microorganism growth.

Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Suitable solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in drugs.

One or more emulsifying agents, wetting agents or suspending agents may be employed in the compositions. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract.

In an alternative embodiment, the composition of the present invention further comprises at least one antibiotic. The choice of antibiotic may depend on the type of infection, any incidence of drug-resistant bacteria in the community, subject allergies, and/or the subject's overall health status. Antibiotics that are suitable for inclusion in the compositions of the present invention may include Amikacin, Azithromycin, Aztreonan, Cefazolin, Cefepine, Cefonicid, Cefaperazone, Cefotaxime, Cefotetan, Cefoxitin, Ceftazidime, Ceftizoxime, Ceftriaxone, Cefuroxime, Cephapirin, Ciprofloxacin, Clindamycin, Doxycycline, Erythromycin Lactobionate, Gentamicin, Kanamycin, Linezolid, Mezlocillin, Mupirocin, Nafcillin, Netilmicin, Neomycin, Oxacillin, Paromomycin, Piperacillin, Streptomycin, Ticarcillin, Tobramycin, and Vancomycin.

Another aspect of the present invention is directed to methods for screening subjects who are susceptible to respiratory infections, or to determine which types of pathogens are colonized in an infected subject. In these methods, the subject orally tastes a plurality of test compounds and rates the intensity of the taste of each of the test compounds. The test compounds include at least one bitter taste agonist and at least one test compound unrelated to bitter taste receptors.

Subjects have very diverse susceptibility to respiratory infections. Although most people are exposed to some form of aerosolized bacteria in their lifetimes, only a subset (16% of the population) will develop ongoing and persistent infections. One important factor in defining this susceptibility is the bitter taste receptor signaling, which plays an important role in inducing innate antimicrobial immunity against inhaled bacteria. Poor bitter taste sensing in the respiratory tract results in a higher susceptibility to respiratory infections.

The taste test relies on the bitter taste sensitivity of tongues, which is genetically determined, to indicate the bitter taste function in the upper respiratory tract. More specifically, if the taste receptor cells on the tongue are less sensitive to bitter taste compounds because they have bitter taste receptors that function poorly, these same bitter taste receptors in the upper respiratory tract will provide a poor defense against microbes. It is known that some people cannot taste particular bitter compounds or they can taste them but only at concentrations that are much higher than are typically needed by others. Bitter taste receptors function differently from person-to-person. As a result, without wishing to be bound by theory, individuals will differ in how well or how broadly their innate antimicrobial defense mechanism functions, as a result of the level of function of their bitter taste receptors. Therefore, it has been found that subjects whose tongues are relatively less sensitive to bitter compounds are more likely to be infected with respiratory pathogens.

The bitter taste sensitivity may be due to the genetic variations of bitter taste receptors within a population, or expression of a different subset of bitter taste receptors in different persons, or perhaps due to lifestyle choices (smoking), or the presence or absence of microbes in the upper respiratory tract. The genetic variations in some of these bitter taste receptors are known to be strongly associated with reduced ability to taste particular bitter compounds. For example, one bitter receptor on chromosome 7 (T2R38) is associated with taste sensitivity of phenylthiocarbamide (PTC). People with a low function allele of this bitter taste receptor report the PTC solution is weak or tastes like water whereas the people with the high functioning alleles report the solution is extremely bitter. It has been observed that people with nasal infections are also more likely to have the insensitive form of the PTC receptor.

One example of bitter taste receptor is T2R38, whose different genotypes lead to subjects' different abilities to perceive bitter tasting compounds. Subjects with a PAV/PAV genotype are termed "tasters" because they have a high sensitivity to the bitter compound PTC, while genotype AVI/AVI is termed a "non-taster" because of the poor sensitivity of persons with this genotype to PTC. The heterozygote PAV/AVI genotype gives a person medium sensitivity to PTC. The term "PAV," as used herein, refers to a functional allele with Proline, Alanine, and Valine (PAV) at positions 49, 262, and 296 of T2R38 and the term "AVI," as used herein, refers to a non-functional allele with Alanine, Valine and Isoleucine (AVI) at positions 49, 262, and 296, respectively, of T2R38.

Figures 11A, 11B:
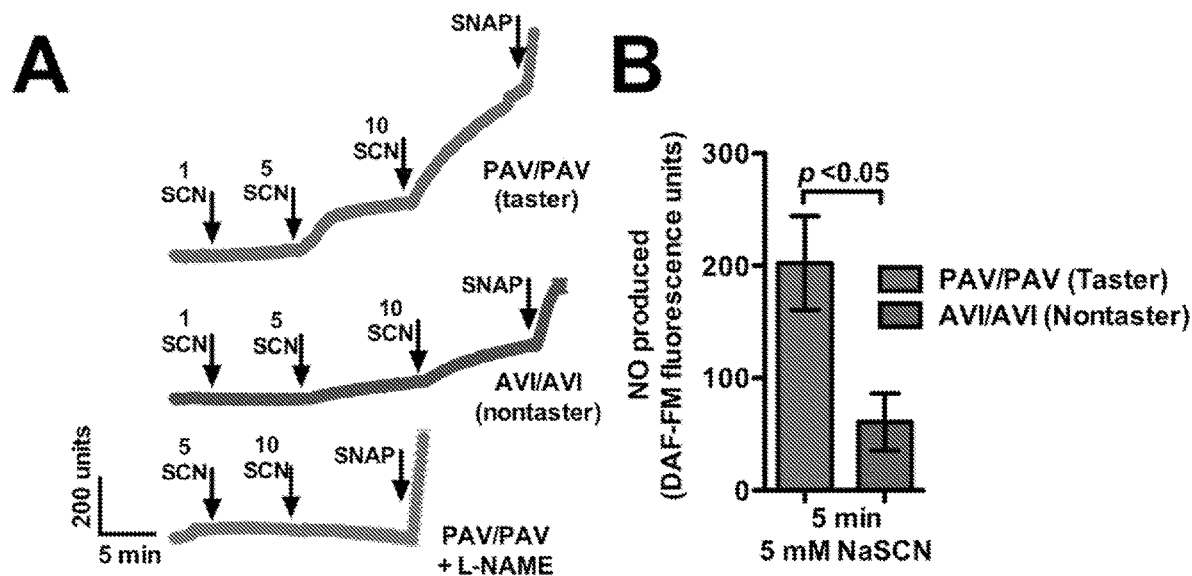
FIG. 11A shows bitter taste receptor T2R38 agonist sodium thiocyanate (NaSCN) stimulates DAF-FM fluorescence traces in sinonasal cultures from patients with different T2R38 genotypes.
FIG. 11B shows NO production in response to 5 mM NaSCN stimulation in sinonasal cultures from patients with different T2R38 genotypes.

The sensitivity to the taste of bitter compounds may translate into different biological responses to activation of a bitter taste signaling pathway (FIGS. 9A, 9B, 9C, 9D 10A, 10B, 11A, and 11B). The cultures from subjects with the PAV/PAV genotype show elevated calcium signaling and NO production in response to PTC. The cultures from subjects with the AVI/AVI genotype show minimal calcium signaling and NO production in response to PTC, and cultures with the heterozygote PAV/AVI exhibit an intermediate level of calcium signaling and NO production comparable to AVI/AVI cultures. On the other hand, calcium production stimulated by the non-bitter agonist ATP as well as NO production stimulated with the non-specific NO donor S-nitroso-N-acetyl-D,L-penicillamine (SNAP) both show no significant difference among the different T2R38 genotypes (FIG. 10). The T2R38 agonist sodium thiocyanate (NaSCN) also induces a higher level of NO production in cultures from subjects with the PAV/PAV genotype (FIGS. 11A and 11B).

The bacterial quorum-sensing molecule butyryl-homoserine lactone (C4HSL; secreted by Gram-negative bacteria such as *Pseudomonas*) also induces different calcium and NO production levels in sinonasal cultures of different T2R38 genotypes. The homozygous taster (PAV/PAV) exhibits the highest calcium and NO production (FIGS. 9C-9D and 12A-12B). The presence of L-NAME, a nitric oxide synthase inhibitor, represses the NO production in taster sinonasal cultures. The C4HSL-induced NO production is also blocked by inhibition of PLCbeta2, an important downstream component of bitter taste signaling, with U73122, but not its inactive analogue U73343.

Figures 12A, 12B, 12C:
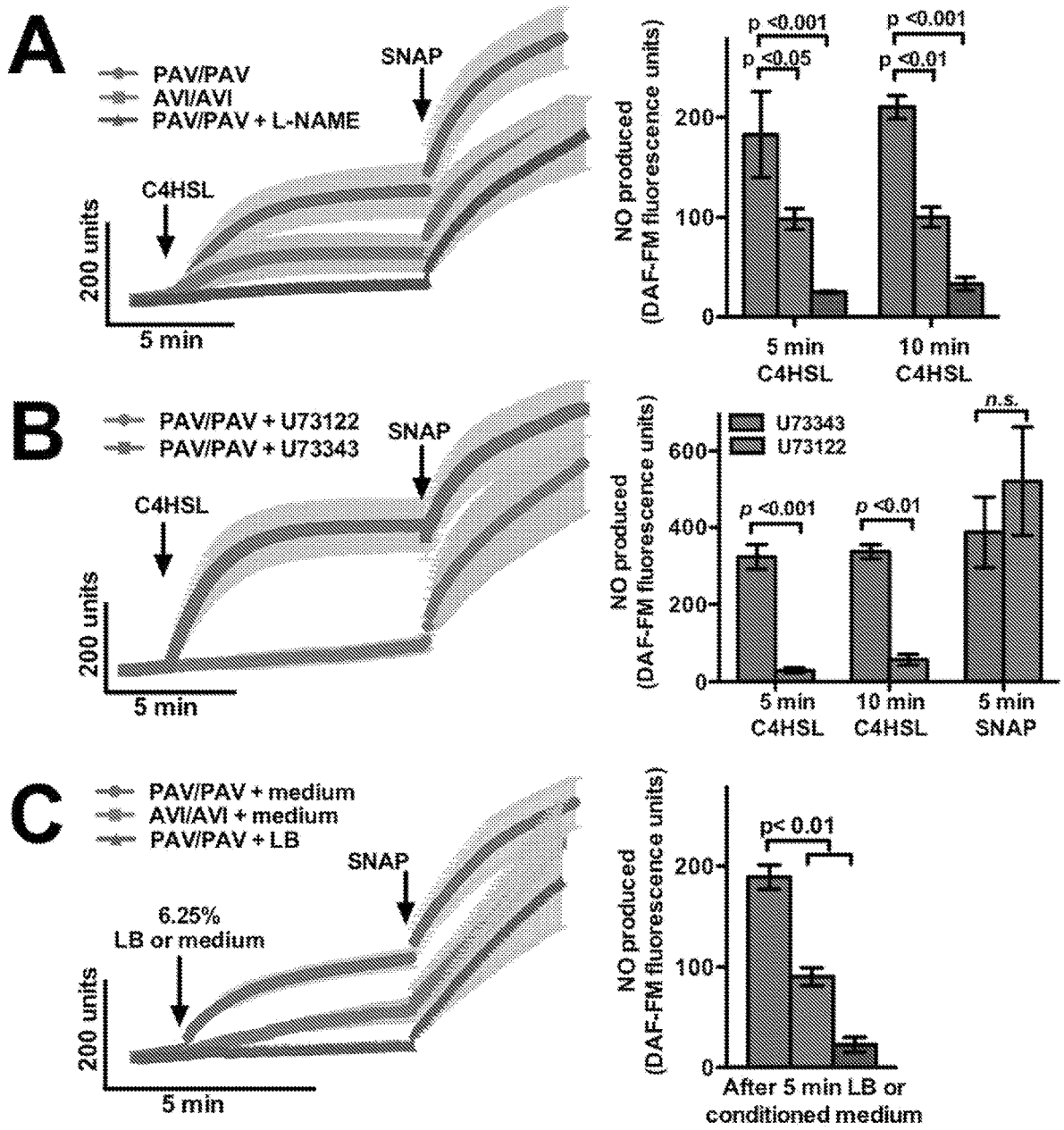
FIG. 12A shows DAF-FM traces and NO production in response to the *Pseudomonas* quorum-sensing molecule butyryl-homoserine lactone (C4HSL; 200 µM) in sinonasal cultures from patients with different T2R38 genotypes.
FIG. 12B shows C4HSL-induced DAF-FM traces and NO production in sinonasal cultures from patients with different T2R38 genotypes, which may be blocked by inhibition of PLCbeta2.
FIG. 12C shows DAF-FM traces in response to stimulation with *Pseudomonas* conditioned medium (from a culture grown in LB medium for 3-days) or LB alone in sinonasal cultures from patients with different T2R38 genotypes.

*Pseudomonas* conditioned medium also induces NO production (FIG. 12C). Sinonasal cultures of different T2R38 genotypes are stimulated with a low concentration (6.25%) of *Pseudomonas* conditioned medium (from a culture grown in LB medium grown for 3-days and then centrifuged and filter sterilized) or LB alone. NO production varies by T2R38 genotype, with the homozygous taster (PAV/PAV) cultures exhibiting the higher NO production than non-taster (AVI/AVI) cultures.

Figures 13A, 13B, 13C, 13D:
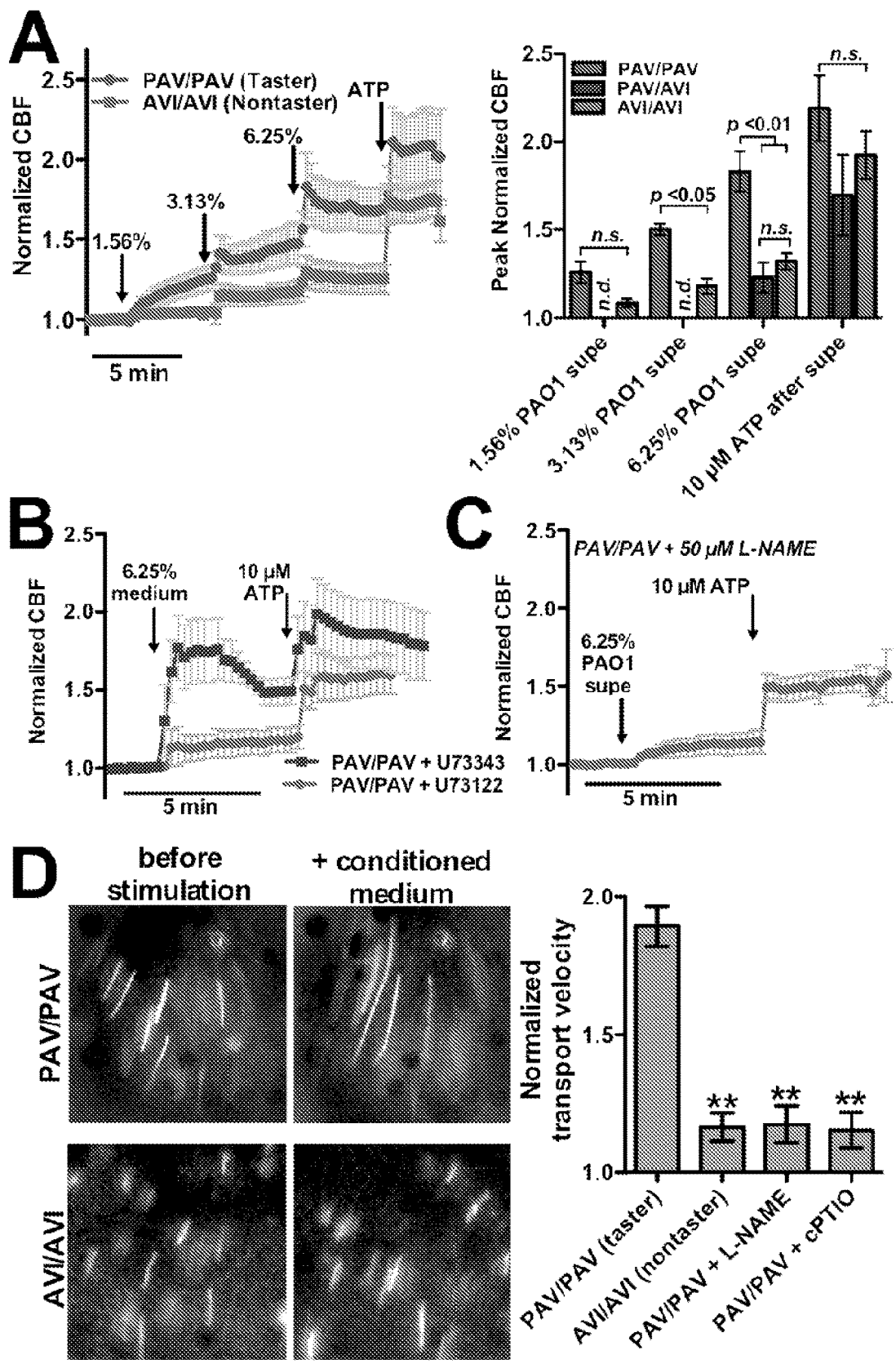
FIG. 13A shows ciliary beat frequency (CBF) in response to *Pseudomonas* (strain PAO1) supernatant (supe) in sinonasal cultures from patients with different T2R38 genotypes.
FIG. 13B shows PAO1 supernatant induced CBF increase may be inhibited by U73122 but not by U73343.
FIG. 13C shows PAO1 supernatant induced CBF increase may be inhibited by the nitric oxide synthase inhibitor $N^G$-nitro-L-arginine methyl ester (L-NAME).
FIG. 13D shows PAO1 supernatant increases the epithelial transport velocity of fluorescent microspheres in T2R38 tasters (PAV/PAV) but not non-tasters (AVI/AVI)
Figure 14:
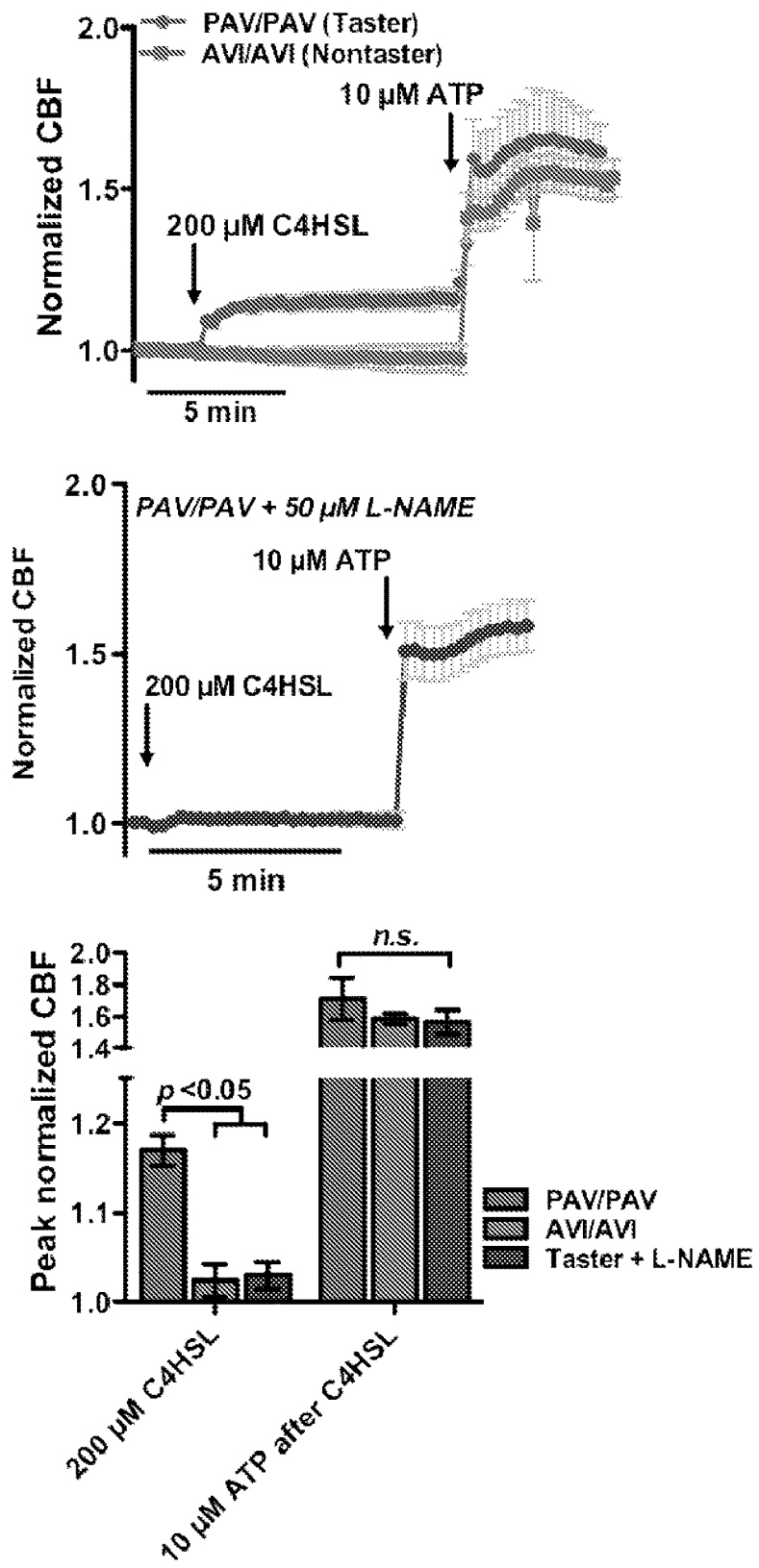
FIG. 14 shows C4HSL activates CBF in sinonasal cultures from patients with different T2R38 genotypes.

Ciliary beat frequency (CBF) may also be induced by *Pseudomonas* conditioned medium (FIGS. 13A-13C). The *Pseudomonas* (strain PAO1) supernatant increases CBF more in homozygous tasters (PAV/PAV) than in non-tasters (AVI/AVI). The CBF increase in response to 6.25% PAO1 supernatant may be inhibited by U73122 (PLCbeta2 inhibitor) but not by U73343 (inactive analogue), suggesting that CBF increase depends on components of taste signaling. The CBF increase is also significantly inhibited by L-NAME, showing it is dependent on NO synthesis by NOS. Butyryl-homoserine lactone (C4HSL) also activates a nitric oxide (NO)-dependent increase in CBF in T2R38 taster (PAV/PAV) cultures but not in T2R38 nontaster (AVI/AVI) cultures (FIG. 14).

Increased CBF by *Pseudomonas* conditioned-medium (supernatant) directly translated into an increase in epithelial transport velocity, as measured by imaging the path lengths (during a 2 second exposure) of fluorescent microspheres propelled by cilia across the epithelium (FIG. 13D). *Pseudomonas* supernatant increased transport velocity in PAV/PAV (taster) cultures but not in AVI/AVI (non taster cultures). The increase in velocity observed in PAV/PAV cultures was blocked by 2 inhibitors of NO signaling, the NOS inhibitor L-NAME and the NO scavenger carboxy-PTIO (cPTIO). This suggests that activating bitter taste signaling would directly result in enhanced bacterial clearance from the nose.

The differences in response to bacterial products such as *Pseudomonas* conditioned medium in subjects of different T2R38 genotypes indicates that these subjects may have different degrees of susceptibility to bacterial infections in the respiratory tract. The present invention thus provides a taste test to screen for subjects who are more susceptible to upper respiratory tract infections, and which may also be used to identify the type of pathogens that are likely to be colonized in the respiratory tract of an infected subject. The taste test uses a plurality of test compounds, some related to bitter taste, some unrelated. The bitter test compounds used in the taste test may include phenylthiocarbamide, quinine and denatonium benzoate. There are many other bitter test compounds which may also be used in the taste test. The test compounds unrelated to bitter taste, such as sugar or salt, are for the purpose of determining whether the overall taste sense of the subject is normal and thus function primarily as control substances.

In one exemplary embodiment, PTC taste testing is used to identify subjects with higher susceptibility to *Pseudomonas* infections (FIGS. 9A, 9B and 10) or infections with other Gram-negative bacteria that secrete C4HSL and/or other homoserine lactones. The subjects with poor taste perception for PTC are indicated as having a higher susceptibility to *Pseudomonas* infections. Supporting this idea, we found an important correlation with T2R38 genotype and bacterial infection. Cultures from 39 Caucasian subjects were assessed for several types of respiratory bacteria through the clinical microbiology labs at the Hospital of the University of Pennsylvania and genotyped for 39 sites of genetic variation in our laboratory at Monell. (It is a coincidence that we studied 39 subjects and the same number of genetic variant sites.) These sites of genetic variation were in bitter and sweet receptor genes, other chemical receptors, and downstream signaling proteins important in taste. The pathogenic bacteria cultured were *Staphylococcus aureus* and *Pseudomonas*; subjects with *Staphylococcus aureus* alone and subjects with both *S. aureus* and coagulase-negative *Staphylococcus* species were put into two separate categories. We found that people with nasal bacterial infection were less likely to have functional alleles of the bitter receptor TAS2R38: subjects with no sinonasal bacterial growth had a distribution of TAS2R38 haplotypes as expected, allowing for the vicissitudes of small sample size, but subjects with nasal bacteria included fewer than expected who were homozygous for the functional form of the TAS2R38 receptor (PAV/PAV) (Yate's $X^2_{(2)}$=8.40, p=0.015). This effect was marked—about 18% of people of European descent have the PAV/PAV diplotype (combination of two haplotypes), but among subjects with a positive culture of sinonasal bacteria, none of the subjects had this diplotype (Table 1).

TABLE 1

Bitter receptor genetic variation among patients with and without cultured sinonasal bacteria

| Patient group | TAS2R38 genotype | | |
| --- | --- | --- | --- |
| | AVI/AVI | AVI/PAV | PAV/PAV |
| No bacterial growth | 4 | 3 | 4 |
| *Pseudomonas* | 4 | 7 | 0 |
| *Staph. aureus* | 6 | 11 | 0 |
| Total infected | 10 | 18 | 0 |

| | TAS2R19 (rs10772420) genotype | | |
| --- | --- | --- | --- |
| | A/A | A/G | G/G |
| No bacterial growth | 2 | 6 | 3 |
| *Pseudomonas* | 3 | 6 | 2 |
| *Staph. aureus* | 3 | 9 | 5 |
| Total infected | 6 | 15 | 7 |

Patients were genotyped for three variants of TAS2R38 (A49P, V262A, and I296V; rs713598,rs1726866, and rs10246939). TAS2R19 was typed for rs10772420.

We found no such pattern among subjects with and without sinonasal bacteria for the functional and nonfunctional genetic variants in the TAS2R19 (quinine) receptor (Yate's $X^2_{(2)}$=0.13, p=0.94), and no other genetic variants tested were related to this phenotype (p<0.05). Together, these data indicate that subjects who cannot taste bitter agonists that signal through T2R38 may be more susceptible to *Pseudomonas* or *Staphylococcus aureus* infection.

In another exemplary embodiment, the taste test is conducted as follows. Subjects are asked to rate the taste of water, sucrose (0.35M), sodium chloride (0.25M), PTC (180 µM), quinine HCl (56 µM) and denatonium benzoate (1.8 µM). Here, water, sucrose, sodium chloride and quinine serve as controls to ensure the subject's taste sense functions normally. Denatonium is used to assess the sensitivity of bitter taste perception, which is correlated with susceptibility to respiratory tract infections, especially upper respiratory tract infections.

During a taste test, each of these test compounds may be presented in a series of concentrations to the subject. The solutions of these compounds may be provided to the subject in tightly-capped, single-use vials. The subject is also provided with a large cup to collect the expectorated solutions and a bottle of water to rinse the mouth before each solution is tasted.

After tasting each taste compound, the subject is asked to rate the intensity of the taste on a validated scale. Examples of such scales are described in detail by Green at al., "Evaluating the 'Labeled Magnitude Scale' for measuring sensations of taste and smell," *Chem Senses* 21, 323-34 (1996) and Bartoshuk et al. "Valid across-group comparisons with labeled scales: the gLMS versus magnitude matching" *Physiology & Behavior* 82 109-114 (2004), each of which is incorporated herein into this application in its entirety. Briefly after eating or tasting a compound, the subject is asked: "How sweet does it taste?" "How bitter does it taste?" and/or "How intense is the taste?" using a scale such as, for example, the following scale:

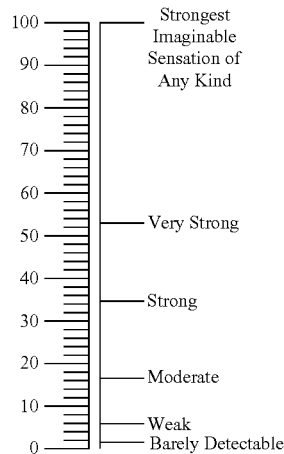

The ratings are then analyzed in the context of the subject characteristics, including sex and age, to determine the subject's susceptibility to respiratory infections. Poor bitter taste sensitivity as indicated by, for example, the requirement for a larger amount of bitter substance to reach the minimum threshold for the subject's bitter taste perception, indicates a poor innate antimicrobial defense mechanism in the upper respiratory tract. Subjects with lower sensitivity to bitter compounds would be more likely to have respiratory infections.

In another aspect, the invention provides a method for determining a risk of a respiratory infection associated disease or disorder in a subject, the method comprising: obtaining a biological sample from said subject; detecting the presence or absence of a polymorphism in amino acid residue positions 49, 262, and 296 of taste receptor, type 2, member 38 (T2R38), and wherein the presence or absence of said polymorphism indicates whether said subject is at the risk of said respiratory infection associated disease or disorder.

The polymorphism may exist between a functional allele, Proline, Alanine, and Valine (PAV) and a non-functional allele, Alanine, Valine and Isoleucine (AVI) at positions 49, 262, and 296, respectively, of said T2R38.

In one embodiment, the presence of homozygous PAV/PAV alleles indicates that the subject is at lower risk of a respiratory disease or disorder, relative to a subject having homozygous AVI/AVI alleles or heterozygous PAV/AVI alleles. In another embodiment, the presence of homozygous AVI/AVI alleles indicates that the subject is at higher risk of a respiratory disease or disorder, relative to a subject having homozygous PAV/PAV alleles or heterozygous PAV/AVI alleles. In another embodiment, the presence of heterozygous PAV/AVI alleles indicates that the subject is at higher risk of a respiratory disease or disorder, relative to a subject having homozygous PAV/PAV alleles, but at lower risk of a respiratory disease or disorder, relative to a subject having homozygous AVI/AVI alleles.

T2R38 as used herein refers to a taste receptor, type 2, member 38. The amino acid sequence of T2R38 is known in the art, for example the human amino acid sequence of T2R38 can be found in GenBank (Genbank ID No.: NP_789787.4). The amino acid sequence of human T2R38 is also set forth in SEQ ID NO.: 1. T2R38 is encompasses a homologue or a variant of SEQ ID NO.: 1, as well as fragment thereof.

The nucleic acid sequence of T2R38 is also known in the art, for example the human nucleic acid sequence of T2R38 can be found in GenBank (Genbank ID No.: NM_176817.4). The nucleic acid sequence of T2R38 is also set forth in SEQ ID NO.: 2. Also encompassed are T2R38 amino acid sequences that encoded by a nucleotide sequence that is a homologue or variant of SEQ ID NO.: 2, as well as fragments thereof.

A genetic polymorphism can be detected by any method known to one of skilled in the art. In one embodiment, the polymorphism can be detected by detecting amino acids. In another embodiment, the polymorphism can be detected by detecting nucleic acids. These methods are well known in the art. Examples of detection methods include, for example, but are not limited to polymerase chain reaction (PCR) based methods, southern blotting, northern blotting, immuno blotting, in-situ hybridization, and microarray methods.

A respiratory infection associated disease or disorder of the invention can be any sinusitis or rhinosinusitis, known to one of skilled in the art. Examples of sinusitis or rhinosinusitis, include, but are not limited to, a chronic rhinosinusitis, an acute rhinosinusitis, a sub-acute rhinosinusitis, a recurrent acute rhinosinusitis, and an acute exacerbation of chronic rhinosinusitis. In a preferred embodiment, a respiratory infection associated disease or disorder of the invention is a chronic rhinosinusitis.

The causes of sinusitis or rhinosinusitis are known in the art. In one example, sinusitis or rhinosinusitis of the invention can be caused by colonization and/or infection of viral, bacterial, and/or fungal organisms. Chemical irritation can also trigger sinusitis or rhinosinusitis. Examples of such chemical irritation include, but are not limited to, cigarette smoke and chlorine fumes.

The invention further provides methods for determining a need for a surgical intervention to treat a respiratory infection associated disease or disorder in a subject, the methods comprising: obtaining a biological sample from said subject; detecting the presence or absence of a polymorphism in amino acid residue positions 49, 262, and 296 of T2R38, and wherein the presence or absence of said polymorphism indicates whether said subject needs said surgical intervention to treat said respiratory infection associated disease or disorder.

In one embodiment, the presence of homozygous PAV/PAV alleles indicates that the subject does not need a surgical intervention. In another embodiment, the presence of homozygous AVI/AVI alleles indicates that the subject needs a surgical intervention. In yet another embodiment, the presence of heterozygous PAV/AVI alleles indicates that the subject has a lower likelihood to need a surgical intervention, relative to a subject having homozygous AVI/AVI alleles.

In some embodiments, a need for a surgical intervention to treat a respiratory infection associated disease or disorder can be determined by a phenotype test. Any known phenotype associated with the polymorphism can be used. For example, a bitter taste test can be conducted to determine whether a subject is a taster or a non-taster. Based on the determination of subject being a taster or a non-taster, a need for surgical intervention can be determined. In an exemplary embodiment, the bitter taste test can be conducted by having a subject taste one or more control compounds and then taste one or more bitter tasting compounds, optionally at different concentration levels. The intensity of a taste of the control and bitter tasting compounds can be rated and the rated intensities can be correlated to determine whether the subject belongs to a taster or a non-taster category. In one embodiment, the subject being a taster may indicate that the subject does not need a surgical intervention. In another embodiment, the subject being a non-taster may indicate that the subject needs a surgical intervention.

In one embodiment, the invention provides a method for treating a respiratory infection associated disease or disorder, the method comprising: determining whether a subject is a non-taster having homozygous AVI/AVI allele or an individual having a heterozygous PAV/AVI allele. Based on the determination, if a subject is a non-taster having homozygous AVI/AVI allele or an individual having a heterozygous PAV/AVI allele, then such subject can be administered a therapeutically effective amount of quinine. Quinine can stimulate nitric oxide (NO) production in sinonasal epithelial cells and thereby treat a respiratory infection associated disease or disorder in such subject.

In some embodiments, if a subject is a non-taster having homozygous AVI/AVI allele or an individual having a heterozygous PAV/AVI allele, then such subject can be administered a therapeutically effective amount of a composition having *Antidesma* sp. (e.g., *Antidesma bunius*) or its extract or a compound isolated from the extract. The *Antidesma* sp. composition may play role in stimulating nitric oxide (NO) production in sinonasal epithelial cells and thereby treat a respiratory infection associated disease or disorder in such subject.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

"Administration" to a subject is not limited to any particular delivery system and may include, without limitation, topical, parenteral (including subcutaneous, intravenous, intramedullary, intraarticular, intramuscular, or intraperitoneal injection) rectal, transdermal or oral (for example, in capsules, suspensions or tablets). Administration to a host may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.). Administration of a composition of the invention can be combined with other treatment modalities, for example, surgery and others, known to one of skilled in the art.

The "subjects" of the methods of described herein can be used on any suitable mammal. In one embodiment, the mammal is a human, for example, a human patient.

All sequence citations, accession numbers, references, patents, patent applications, scientific publications or other documents cited are hereby incorporated by reference.

The following examples are presented in order to more fully illustrate the preferred embodiments of the invention. They should in no way be construed, however, as limiting the broad scope of the invention.

EXAMPLES

Example 1

This example shows $[Ca^{2+}]$ concentration elevation after stimulation with bitter receptor agonists. Nasal epithelial cells (Sinonasal ALI cultures) were loaded (apical side only) with the fluorescent calcium indicator fluo-4 by incubation in 5 µM fluo-4 AM in PBS containing 0.04% pluronic and 2 mM probenecid. Cells were imaged on an Olympus IX-31 Fluoview confocal microscope. Stimulation of the cells with denatonium increases fluo-4 fluorescence (indicating higher calcium concentration). FIG. 3A shows the average response of 24 cells in one representative cell culture; Fluo-4 fluorescence signal was normalized to the average baseline fluorescence of the first 10 frames ($F_0$). The concentration of denatonium is indicated in FIG. 3A, which caused immediate peaks of Fluo-4 fluorescence. FIG. 3B shows the dose-dependency of $[Ca^{2+}]$ elevation, represented by peak fluorescence, in response to 0.1, 1, 5, 10, and 20 mM denatonium. The signals were calculated based on 10 cell cultures for 10 mM denatonium stimulation; and 4 cell cultures for each of other denatonium concentrations.

Example 2

This example shows bitter taste receptor stimulation evoking antimicrobial secretions by nasal epithelial cells (sinonasal ALI cultures). The apical surface of nasal ALI cultures was washed with PBS (3×200 µL volume), followed by aspiration and addition of 30 µL of 50% PBS or 50% PBS containing denatonium. After incubation at 37° C. for 30 minutes, the apical surface liquid (ASL, containing any secreted antimicrobials) was removed and mixed with an *Pseudomonas aeurginosa* (strain PAO1) or methicillin-resistant *Staphylococcus aureus* (MRSA) that was freshly-diluted (in 25% media) and grown to log-phase. Low-salt conditions (50% PBS; 25% bacterial media) were used because the antimicrobial activity of airway antimicrobials has been shown to have a strong salt-dependence. After incubation for 2 hours at 37° C., bacterial ASL mixtures were plated with serial dilutions and incubated overnight.

The ASL removed from cultures stimulated with denatonium exhibited potent antimicrobial activity relative to the ASL removed from cultures incubated with PBS alone, as evidenced by a significantly reduced number of *Pseudomonas* colony forming units (CFUs; FIG. 4A). Higher NaCl concentrations inhibited the ability of the denatonium-treated ASL to kill *Pseudomonas*. The denatonium-stimulated antimicrobial response was dose-dependent (FIG. 4B) and was inhibited by abolition of $[Ca^{2+}]$ signaling in cells loaded with the calcium chelator BAPTA (incubation in 10 µM BAPTA-AM for 15 minutes) and stimulated with denatonium in the absence of extracellular calcium (PBS containing 2 mM EGTA, but no $Ca^{2+}$). The denatonium-induced antimicrobial response was also inhibited by the PLCβ2 inhibitor U73122 (20 µM; FIG. 4B), which suggests that taste signal transduction pathways underlie this antimicrobial response.

Figure 4C:
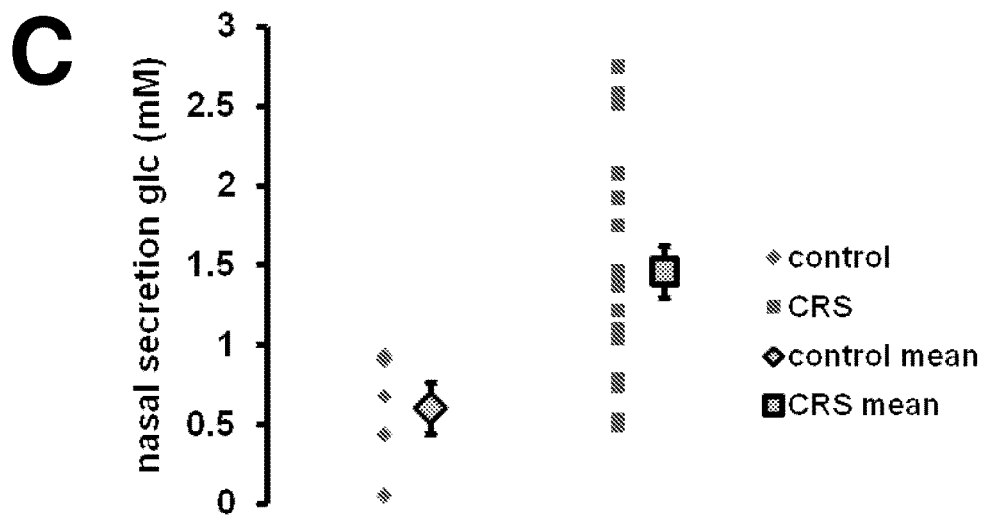
FIG. 4C shows glucose concentrations in nasal secretion samples from control and individuals with CRS obtained using a colorimetric assay.

When nasal epithelial cells were stimulated with denatonium in the presence of glucose, a dose-dependent inhibition of bactericidal activity was observed at 0.5 mM but not at 1.5 mM glucose (FIG. 4B). These concentrations were chosen because they are representative of glucose concentrations that are observed in nasal secretions from control individuals and those with CRS (FIG. 4C). Glucose concentrations were measured in nasal secretion samples from control and CRS individuals using a colorometric assay (Cayman Chemical). Mean nasal glucose was 0.6±0.16 mM in control patients (5 patient) vs. 1.5+0.02 mM in CRS patients (18 patients; p=0.015). Supporting the data shown above, it was found that the sweet receptor antagonist lactisole (5 mM) reduced or reversed the glucose-mediated inhibition of bacterial kill (FIG. 4B). Additionally, no bactericidal response was observed when cells were stimulated with the purinergic agonist ATP (FIG. 4B), a potent calcium agonist in these cells. The denatonium stimulated ALS was also potently bactericidal when tested against MRSA (FIG. 4B).

Example 3

Figure 5:
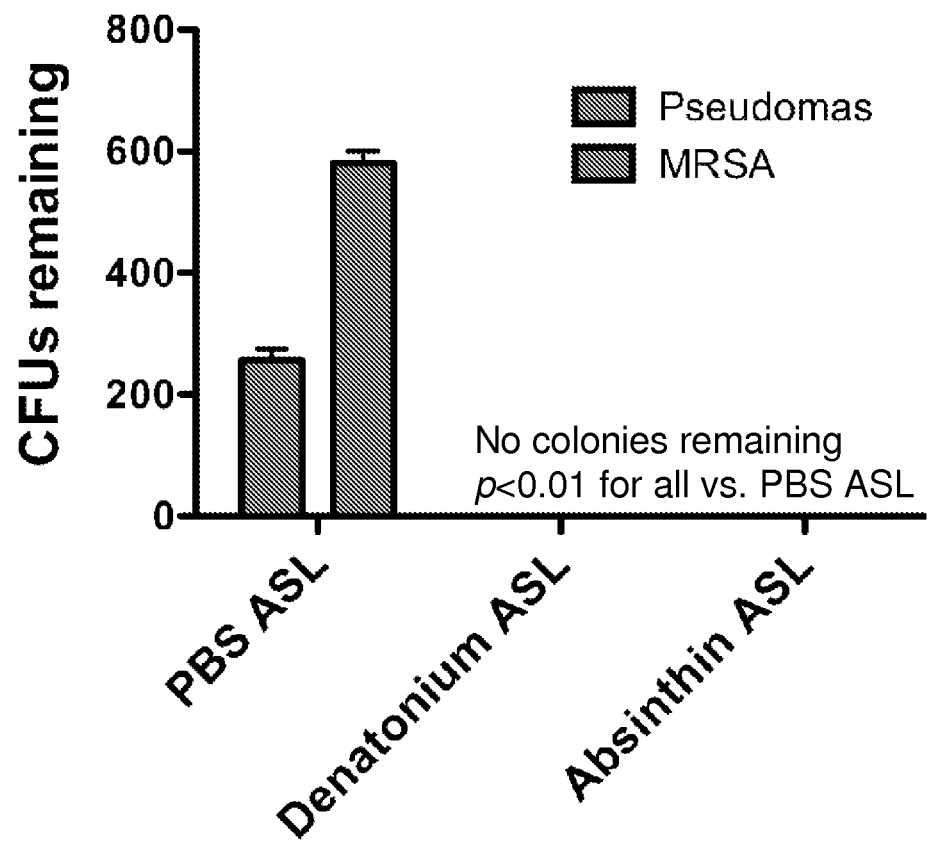
FIG. 5 shows that the bitter taste receptor agonists denatonium and absinthin stimulate antimicrobial activity in sinonasal cell cultures to kill both *Pseudomonas aeruginosa* and Methicillin-resistant *Staphylococcus aureus* (MRSA). This effect is also evident against *Kleibsiella pneumoniae*.

Bitter taste receptor agonists denatonium and absinthin were used to stimulate antimicrobial activity in sinonasal cell cultures to kill both Pseudomonas aeruginosa and MRSA (FIG. 5). The kill assay applies ASL from cultures treated with 50% PBS alone (unstimulated), 10 mM denatonium, and 300 µM absinthin. Airway surface liquid was tested against both Pseudomonas aeruginosa and MRSA. PBS, denatonium, and absinthin solutions alone had no effect on Pseudomonas or MRSA growth (not shown). No growth (0 CFUs) was observed when bacteria were mixed with airway surface liquid from cultures stimulated with denatonium or absinthin.

Example 4

NO production in sinonasal cultures of different T2R38 genotypes in response to Pseudomonas aeruginosa products were assayed for NO production (FIGS. 12A-12C). DAF-FM traces showing NO production in response to the Pseudomonas quorum-sensing molecule butyryl-homoserine lactone (C4HSL; 200 µM) in homozygous taster (PAV/PAV) and non-taster (AVI/AVI) sinonasal cultures, as well as taster cultures in the presence of L-NAME. C4HSL-induced NO production in taster cultures was blocked by inhibition of PLCbeta2, an important downstream component of bitter taste signaling, with U73122 (5 µM; 20 min pre-incubation). The inactive analogue of U73122, U73343, had no effect on NO production. NO production was also measured in homozygous taster and non-taster patients in response to stimulation with a low concentration (6.25%) of Pseudomonas conditioned medium (from a culture grown in LB medium for 3-days and then centrifuged and filter sterilized) or LB alone. NO production varied by T2R38 genotype, with higher production observed in the homozygous taster.

Example 5

T2R38 Taste Receptor Polymorphisms Underlie Susceptibility to Upper Respiratory Infection Innate and adaptive defense mechanisms protect the respiratory system from attack by microbes. Here, evidence is presented that the bitter taste receptor T2R38 regulates the mucosal innate defense of the human upper airway. Utilizing immunofluorescent, and live cell imaging techniques in polarized primary human sinonasal cells, we demonstrate that T2R38 is expressed in human upper respiratory epithelium and is activated in response to homoserine lactone quorum sensing molecules secreted by Pseudomonas aeruginosa and other gram-negative bacteria. Receptor activation regulates calcium-dependent nitric oxide production, resulting in stimulation of mucociliary clearance and direct antibacterial effects. Moreover, common polymorphisms of the TAS2R38 gene were linked to significant differences in the ability of upper respiratory cells to clear and kill bacteria. Lastly, TAS2R38 genotype correlated with human sinonasal gram-negative bacterial infection. These data show that T2R38 is an upper airway sentinel in innate defense and that genetic variation contributes to individual differences in susceptibility to respiratory infection.

Materials and Methods

Reagents.

C4HSL, SNAP, DAF-2, and cPTIO were from Cayman Chemical. Fluo-4, DAF-FM, thapsigargin, ionomycin, Texas Red dextran (10,000 MW), and fluorescent microspheres were from Invitrogen (Grand Island, N.Y.). Unless indicated, other reagents were from Sigma Aldrich (St. Louis, Mo.). Stock solutions of PTC, C4HSL, C12HSL, Fluo-4, DAF-2, DAF-FM, cPTIO, SNAP, thapsigargin, and ionomycin were made at 1000× in DMSO with working solutions made fresh daily. The working SNAP solution (in PBS) was kept on ice in the dark and warmed immediately before use. NaSCN, denatonium, thujone, ATU, and Texas Red dextran stocks were dissolved directly in PBS. Lipopoysaccharides from Pseudomonas aeruginosa serotype 10 were purchased from Sigma and FSL-1 was a gift from Dr. D. LaRosa (University of Pennsylvania). ELISAs for β-defensin and IL-8 were purchased from Adipo Biosciences (Santa Clara, Calif.) and Pierce Biotechnology (Rockford, Ill.), respectively, and performed according to the manufacturer's instructions. Luminex 18-plex kit was used as previously described.

Experimental Solution Compositions.

Physiological experiments were performed with Dulbecco's phosphate buffered saline (DPBS; containing 1.8 min $Ca^{2+}$) on the apical side of the cultures. The basolateral side was bathed in modified HEPES-buffered Hank's Balanced Salt solution (HBSS) containing 1× minimal essential medium (MEM) amino acids (Invitrogen, Grand Island, N.Y.) to provide a source of arginine (~0.6 mM) for NO production. DPBS contained (in mM) 138 NaCl, 2.7 KCl, 1.5 $KH_2PO_4$, 8 $Na_2HPO_4$, 1.8 $CaCl_2$, and 1.5 $MgCl_2$, with pH adjusted to ~7.2 (to prevent any $Ca^{2+}$ precipitation due to the high phosphate concentrations in PBS). HBSS contained (in mM) 137 NaCl, 5 KCl, 0.4 $KH_2PO_4$, 0.3 $Na_2HPO_4$, 5.5 glucose, 1.8 $CaCl_2$, 1.5 $MgCl_2$, 10 HEPES, pH 7.4. Experiments performed in the absence of extracellular $Ca^{2+}$ (0–$Ca^{2+}_o$) utilized the above solutions with no added $Ca^{2+}$ and containing 1 mM EGTA.

Sinonasal ALI Cultures.

Patients were recruited from the Division of Rhinology of the Department of Otorhinolaryngology—Head and Neck Surgery at the University of Pennsylvania and the Philadelphia Veterans Affairs Medical Center with full approval of both Institutional Review Boards. Informed consent was obtained during the pre-operative clinic visit or in the pre-operative waiting room. Selection criteria for recruitment were patients undergoing sinonasal surgery. Exclusion criteria included a history of systemic diseases such as Wegner's, Sarcoid, Cystic fibrosis, immunodeficiencies, and use of antibiotics, oral corticosteroids, or anti-biologics (e.g. Xolair) within one month of surgery. Sinonasal mucosal specimens were acquired from residual clinical material obtained during sinonasal surgery and transported to the laboratory in saline placed on ice. ALI cultures were established from human sinonasal epithelial cells (HSEC) enzymatically dissociated human tissue as previously described and grown to confluence in tissue culture flasks (75 cm$^2$) with proliferation medium consisting of DMEM/Ham's F-12 and bronchial epithelial basal medium (BEBM; Clonetics, Cambrex, East, N.J.) supplemented with 100 U/mL penicillin, 100 µg/mL streptomycin for 7 days. Cells were then trypsinized and seeded on porous polyester membranes (6~7×10$^4$ cells per membrane), in cell culture inserts (Transwell-clear, diameter 12 mm, 0.4 µm pores; Corning, Acton, Mass.) coated with 100 µL of coating solution [BSA (0.1 mg/mL; Sigma-Aldrich), type I bovine collagen (30 µg/mL; BD), fibronectin (10 µg/mL; BD) in LHC basal medium (Invitrogen) and left in a tissue culture laminar flow hood overnight. Five days later the culture medium was removed from the upper compartment and the epithelium was allowed to differentiate by using the differentiation medium consisting of 1:1 DMEM (Invitrogen, Grand Island, N.Y.) and BEBM (Clonetics, Cambrex, East Rutherford, N.J.) with the Clonetics complements for hEGF (0.5 ng/mL), epinephrine (5 g/mL), BPE (0.13 mg/mL), hydrocortisone (0.5 g/mL), insulin (5 g/mL), triiodothyronine (6.5 g/mL), and transferrin (0.5 g/mL), supplemented with 100 UI/mL penicillin, 100 g/mL streptomycin, 0.1 nM retinoic acid (Sigma-Aldrich), and 10% FBS (Sigma-Aldrich) in the basal compartment. Human bronchial epithelial cells (Lonza, Walkersville, Md.) were similarly cultured as previously described. Microbiology swabs were processed by the clinical microbiology lab using both blood agar as well as MacConkey agar for isolation of gram-negative bacteria.

Bacterial Culture.

For biofilm-conditioned medium (CM), *Pseudomonas aeruginosa* (strain PAO1) cultures were grown for 3 days in 24 well plates with the resultant media centrifuged at 2000×g for 15 minutes at room temperature and subsequently filtered through a 0.2 µM filter. The resultant CM was then adjusted to an $OD_{655}(77)=0.35$ when blanked against LB. Planktonic growth cultures of Wt PAO1, PAO-JP2 (ΔlasI, ΔrhlI; Tc$^r$, HgCl$_2^r$) (56), and Sad36 ((flgK::Tn5B30(TC$^r$))(60); were grown for 12 hours at 37° C. with shaking in LB (PAO1) or LB+15 µg/mL tetracycline (PAO-JP2 and Sad36); conditioned medium was prepared as described above. Conditioned PBS (CPBS) was made by taking a 12-hour overnight culture, diluting it to 0.1 OD (log phase) and incubating at 37° C. with shaking for 90 min in LB. Bacteria were then centrifuged, washed 3× with PBS+ 0.5 mM glucose, resuspended at 0.1 OD in the same solution, and incubated at 37° C. with shaking. This glucose concentration was chosen because physiological ASL glucose concentrations have been demonstrated to be ~10% of serum glucose, which is normally ~5-8 min (78-81). Aliquots of this solution were taken at 30 mM, 2 hrs, and 6 hrs and then centrifuged and filter sterilized as described above. Bacteria did not grow robustly under these conditions, as the initial ODs (0.12±0.03, 0.10±0.02, and 0.13±0.03 for PAO1, PAO-JP2, and Sad36; average of 3 independent dilutions and readings) were not significantly different from the final ODs (0.15±0.03, 0.13±0.02, and 0.16±0.01, respectively). Dialysis of CPBS was performed for approximately 16 hrs at 4° C. against a ~1,000 fold excess of the same PBS solution (changed once after the first 6 hrs) using a 3,500 MWCO dialysis membrane (Spectra/Por®; Spectrum Medical Industries, Inc., Laguna Hills, Calif.). As a control, undialyzed CPBS from the same cultures was incubated similarly and tested to ensure that the lack of effect of dialyzed CPBS was not due to degradation of the bacterial products.

Immunofluorescent Staining and Confocal-Microscopy.

Mucosal specimens and ALI cultures appropriate for immunostaining were fixed in 4% paraformaldehyde for 20 min at 4° C. and subsequently washed three times in PBS. Primary human sinonasal epithelial ALI cultures were grown to maturity, washed 3 times with PBS, and fixed in 4% paraformaldehyde for 20 min at room temperature. The transwell permeable support was again washed 3 times with PBS prior to excision of the membrane containing the cells from its plastic supports. The membrane was immersed in Tris-buffered saline (TBS) with 0.3% Triton X-100, 5% normal donkey serum, and 1% bovine serum albumin for 60 min at room temperature to permeabilize the plasma membrane and block non-specific binding sites. Two primary antibodies raised from different hosts were chosen for the double immunofluorescent staining: mouse monoclonal anti-β-Tubulin IV (1:1000; Abcam, Cambridge, Mass.) and rabbit polyclonal anti-T2R38 (1:500; Santa Cruz Biotech, Santa Cruz, Calif.). Visualization was carried out with Alex Fluora®488 (green)-conjugated donkey anti-mouse IgG for tubulin IV and Alex Fluora® 594 (red)-conjugated donkey anti-mouse IgG for T2R38. Both secondary antibodies (Invitrogen, Grand Island, N.Y.) were diluted at 1:500. The incubation time was overnight at 4° C. for primary antibodies and 75 min at room temperature for secondary antibodies, respectively. Counterstaining was done with Hoechst (blue), a nuclear dye. Confocal images were acquired with Olympus Fluoview System at the Z-axis step of 0.5 µm. Sequential scanning module was used to prevent bleed-through of fluorophores into other channels.

Profiles of red and green fluorescence (to determine height of ciliary staining) were performed on z-axis projections exported from Olympus Fluoview software using the RGB Line Profile plug-in of the McMaster Biophotonics (McMaster University, Canada) ImageJ bundle. Correlation coefficients were obtained using the method of Manders and the Manders Coefficients plug-in of the McMaster ImageJ bundle on the raw Fluoview z-stacks. Z-axis step size was 0.5 µm; correction for refractive index change using the paraxial approximation of $n_2/n_1$ method (water [1.33/oil [1.51]) results in an approximate pixel size of ~0.44 µm (10 pixels ~8 µm).

Reverse Transcription-PCR.

ALI cultures were subjected to RNA extraction using an RNeasy Mini Kit (Qiagen, Valencia, Calif.) reverse transcriptase. Contaminate genomic DNA was removed by treating the samples with RNase-free DNase (Qiagen) for 30 minutes at room temperature during the extraction process. cDNA synthesis was performed using 1 µg RNA, Superscript III Reverse Transcriptase (Invitrogen, Grand Island, N.Y.) and random hexamers according to the manufacturers' recommendations. Negative control templates were synthesized by omission of reverse transcriptase. PCR was performed in 50 µl reaction tubes containing 1 unit Taq DNA Polymerase (Invitrogen, Grand Island, N.Y.), 1×PCR buffer, 1 µM dNTP mix, 1.5 mM $MgCl_2$, 1.5% DMSO, 0.5 µM Forward and Reverse primers, and 2 µL cDNA. Thermal cycling conditions consisted of an initial denaturation at 94° C. for 2 min followed by 35 amplification cycles of 94° C. for 20 s, 58° C. for 40 s, and 72° C. for 30 s. A final elongation step was performed at 72° C. for 10 min.

Live-Cell Imaging of Fluo-4 and DAF-FM in Human ALI Cultures.

Fluo-4 and DAF-FM imaging were performed according to standard methods using the 488 nm argon laser line of a Fluoview FV1000 laser scanning confocal system and IX-81 microscope (10×, 0.3 NA UPlanFLN objective; Olympus). Cells were loaded with Fluo-4 by incubation at room temperature in the dark with apical solution containing 10 µM Fluo-4-AM for approximately 90 min. After loading with Fluo-4, cultures were washed 3 times with DPBS followed by incubation for 15-20 min to allow for de-esterification of the loaded dye. Cultures were mounted in a custom made chamber with a #1 coverslip bottom and basolateral solution volume of ~300 µL (changed after each experiment). No evidence of significant photobleaching, toxicity, and/or dye extrusion was noted. Fluo-4 images were captured at ~5 second intervals (scan speed 10 µs/pixel; 512×512 resolution). To maximize light collection and to minimize any effects of focal drift over the time course of experiments, all experiments were performed with a fully open confocal aperture to roughly approximate wide-field conditions. No gain, offset or gamma alterations were used. Normalization of Fluo-4 fluorescence changes was made after subtraction of background fluorescence, approximated for each experiment by measuring unloaded ALIs at identical settings. Baseline Fluo-4 fluorescence ($F_o$) was determined by averaging the first 10 frames of each experiment.

Preliminary experiments revealed that DAF-FM loading itself caused epithelial cells to have an elevated baseline NO production, evidenced by high background DAF-FM fluorescence at the beginning of experiments. Cells were thus loaded with DAF-FM by incubation in DPBS containing 10 µM DAF-FM diacetate in PBS containing 5 µM carboxy PTIO, a cell permeant NO scavenger (on the apical side only). After 30 min, cultures were copiously washed (at least 5 times) with PBS to remove all traces of unloaded DAF-FM and cPTIO. This loading protocol greatly reduced starting DAF-FM fluorescence levels. Cultures were then incubated for ~15 min to allow for dye retention before imaging was performed. DAF-FM fluorescence images were acquired at 5 second intervals using identical setting to those used for Fluo-4. Because the magnitudes of DAF-FM fluorescence changes are used to approximate NO production, care was taken to follow the loading protocol strictly to normalize dye loading and microscope/software settings were identical for each experiment.

Transfection with siRNA.

Human sinonasal epithelial cells were transfected with siRNA at the time of plating on transwell filters. Cells were seeded at a density of $1×10^5$ per transwell in media containing 50% LHC9 in RPMI1640 without antibiotics together with 40 µL of Opti-MEM (Invitrogen) containing preformed siRNA complexes (100 µM) and 0.6 µl of Lipofectamine RNAi MAX. The basolateral side contained 500 µL of LHC9/RPMI1640 without antibiotics. Transfection reagent, siRNA, and control RNAs were all from Invitrogen and siRNA transfection was performed according to the manufacturer's instruction. Invitrogen Stealth RNAi siRNA oligo duplexes directed against human T2R38 were CCAGAUGCUCCUGGGUAUUAUUCUU (SEQ ID NO.: 3) and AAGAAUAAUACCCAGGAGCAUCUGG (SEQ ID NO.: 4) (TAS2R38HSS108754(3_RNAI); siRNA "54"), GGCACAUGAGGACAAUGAAGGUCUA (SEQ ID NO.: 5) and UAGACCUUCAUUGUCCUCAUGUGCC (SEQ ID NO.: 6) (TAS2R38HSS108755 (3_RNAI); siRNA "55"), and CCUACUGAUUCUGUGGCGCGACAAA (SEQ ID NO.: 7) and UUUGUCGCGCCACAGAAUCAGUAGG (SEQ ID NO.: 8) (TAS2R38HSS108756(3_RNAI); siRNA "56"). The non-targeting negative control was Stealth siRNA negative control duplex (Cat. No. 12935-200). After transfection, siRNA complexes were removed after 24 h and cells were fed with differentiation medium as described above. The transfected cells were used after ~10-12 days.

Heterologous Expression.

The human TAS2R38 constructs were generated according to Bufe et al. In brief, the human TAS2R38 was amplified by genomic PCR from two PAV and AVI homozygotes. The sequence encoding the first 45 amino acids of rat SSTR-3 was amplified by PCR from rat genomic DNA. The two fragments were joined by overlapping PCR and inserted into pcDNA3.1 (+) vector. All constructs were verified by sequencing. Gα16-gust44 clone was described previously. HEK293 (peakRapid) cells were obtained from ATCC(CRL-2828) and cultured at 37° C. in opti-MEM (Invitrogen) supplemented with 5% fetal bovine serum (Invitrogen). For transient transfection, cells were seeded onto 96-well plates coated with poly-lysine at 40,000 cells per well. Cells were transfected with either version of hTAS2R38, along with Gα16-gust44. Equal amounts of each cDNA were transfected, totaling 0.2 µg per well. After another 24 h, the cells were washed with Hank's balanced salt solution (HBSS) and loaded with 50 µL of 3 µm Fluo-4 (Invitrogen) in HBSS, and incubated for 1 h. Then the cells were washed three times with HBSS and left in 50 µL HBSS. The dye-loaded transfected cells in plates were placed into a Molecular Devices FlexStation III system to monitor the change in fluorescence (excitation, 488 nm; emission, 525 nm; cutoff, 515 nm) after the addition of 50 µl compound solution at twice the final concentration at 30 s after the start of the scan, scanning continued for an additional 150 s, and data were collected every 2 s. Intracellular calcium mobilization was quantified as the percentage of change (peak fluorescence– baseline fluorescence level, denoted as ΔF) from its own baseline fluorescence level (denoted as F). Peak fluorescence intensity occurred about 20 s after the addition of ligands. As controls, buffer alone evoked no change of fluorescence (ΔF/F≈0, S.E. is about 1%). The data were expressed as the mean±S.E. of the ΔF/F value of three independent samples.

Measurement of Ciliary Beat Frequency and Mucociliary Transport Velocity.

Cultures were imaged using a high-speed camera (Basler 602f; 100 frames/second) attached to an inverted Leica Microscope (20×, 0.8 N.A. objective) lens. Ciliary beat frequency was measured using the Sisson-Ammons Video Analysis (SAVA) system. All experiments were performed at ~28-30° C. Mucociliary transport velocity was measured using 2 µm polystyrene fluorescent microspheres (0.0025% by weight in 30 µl) that were added to the apical surface of the cultures after copious washing with PBS to remove mucus clumps. Beads were imaged using an inverted Nikon TE2000E epifluorescence microscope (20×0.5 NA Plan-Fluor objective) equipped with a 12-bit QImaging camera and computer running ImageJ (W Rasband, NIH) and µManager. A streak had to have a visible beginning and ending, within the field of view, to be included in the statistical analysis of the data. Either an ND4 or ND8 filter was used for bead-tracking experiments, depending on the thickness of the individual epithelial culture and resulting brightness of the beads.

Wide Field Fluorescence Imaging of NO Secretion and Particle Velocity.

For measurement of NO secretion, a protocol was developed in which a solution of Texas Red Dextran (an NO-insensitive cell-impermeant dye) and DAF-2 (an NO-sensitive cell-impermeant dye) were added in a small volume (10 µl) to the apical surface of the cultures. The ratio of DAF-2/Texas Red fluorescence was recorded using widefield epifluorescence microscopy at baseline and after incubation at 37° C. for the indicated times. This experiment was validated by addition of DETA-NONOate, an NO donor that releases 2 moles of NO per mole of parent molecule. DETA-NONOate was added on top of ALI cultures in pH 5 buffer to stimulate rapid decomposition. Imaging was performed using a Nikon 20×0.5 NA PlanFluor objective and 100 W mercury arc lamp with filters from Chroma Technologies (Rockingham, Vt.). Green filter contained a 480/40 nm band-pass [bp] excitation filter (reported as max transmission wavelength/filter width at half maximal transmission), a 505 nm dichroic mirror, and a 535/40 nm by emission filter. Red filter set contained a 560/40 nm by excitation filter, 595 dichroic mirror, and 630/60 nm by emission filter.

Measurement of NO-Metabolites.

ASL from stimulated and unstimulated cultures (20 µL total volume for each) was collected after 20 min at 37° C. and frozen at −20° C. and protected from light until analysis. NO-metabolites were evaluated by reduction of metabolites with acidified-heated vanadium to nitric oxide and detection of nitric oxide by chemiluminescence on the Sievers 280 nitric oxide analyzer. Samples were injected into a custom made purge container containing 0.05 M Vanadium chloride in 1 N HCl heated to 95° C. The reading in millivolts was compared to a standard curve generated by injecting standard solutions of nitrate. This reductive method reports on the total levels of nitrate, nitrite, N-nitroso and iron-nitrosyl adducts as well as low molecular weight and protein S-nitrosothiol adducts.

Genetic Analyses.

Genomic DNA was extracted from cultured cells or sinonasal specimens following the directions of the manufacturer (Qiagen, QIAmp DNA Mini and Blood Mini kit). For correlation with clinical infection, sinonasal specimens of Caucasian patients were used since the TAS2R38 allele frequency is known for northern European descent. Following extraction, samples were quantified using a spectrophotometer (Nanodrop ND-1000), using 1.5 µL of extracted genomic DNA. Samples were diluted to 5 ng/µL and genotyped using the ABI StepOne real time PCR system. Alleles of the gene TAS2R38 were genotyped for a variant site using allele-specific probes and primers (Applied Biosystems).

Pseudomonas Live-Dead Assay.

Pseudomonas from an overnight culture were diluted in LB, grown to log phase (OD=0.1), then resuspended in low-salt (50%) saline+0.5 mM glucose+1 mM HEPES (pH 6.5; gassed with 1% $O_2$ to minimize the immediate reaction of secreted NO with dissolved $O_2$) and incubated with shaking for 60 min. These conditions were chosen to mimic physiological nasal airway surface liquid conditions. Bacteria in 30 µL of this solution were placed on the apical side of the ALI and allowed to settle for approximately 10 mM Afterward, the majority of ASL fluid was aspirated, leaving only a minimal amount remaining. Antibiotic-free F-12 medium+glutamate was used as the basolateral solution.

After a 2 hour incubation at 37° C. at 1% $O_2$, bacteria were removed from the cultures by washing with 30 µL saline, which was then aspirated and placed into a chamber on a glass coverslip for viewing. Due to the thickness and geometry of the ALI filter as well as small amounts of background autofluorescence, direct viewing of bacteria on the ALI at high resolution was not feasible. Bacteria were mixed with 30 µL of a 2× solution of SYTO® 9 and propidium iodide (LIVE/DEAD® BacLight® Bacterial Viability Kit, Invitrogen) and visualized using wide-field epifluorescence filters as described above. Control experiments were performed by similarly incubating bacteria on transwell filters without cells in saline solution alone or in saline solution with 10 µg/mL colistin sulfate, a potent anti-Pseudomonas antibiotic. Staining was quantified by determining the area of positive red and green fluorescence for each image thresholding of each channel in ImageJ; these values were used to calculate total fluorescent area (red+green) and the percentage of green fluorescent area, which, as live and dead cells appeared to be equal size, was assumed to equal the percentage of live (green) cells.

Data Analysis and Statistics.

All statistical analyses were performed in Excel (Student's t test) and/or GraphPad Prism (Student's t test, Chi squared test, ANOVA) as indicated; P<0.05 was considered statistically significant. For multiple comparisons, ANOVA with Bonferroni post-test was used when pre-selected pairwise comparisons were performed, ANOVA with Tukey-Kramer post-test was used when all values in the data set were compared, and ANOVA with Dunnett post-test was used when all values were compared with a control value. For all figures, *=P<0.05, **=P<0.01, and n.s.=no statistical significance.

Results

T2R38 is Expressed and Functional in Human Upper Airway Cells.

Figure 15:
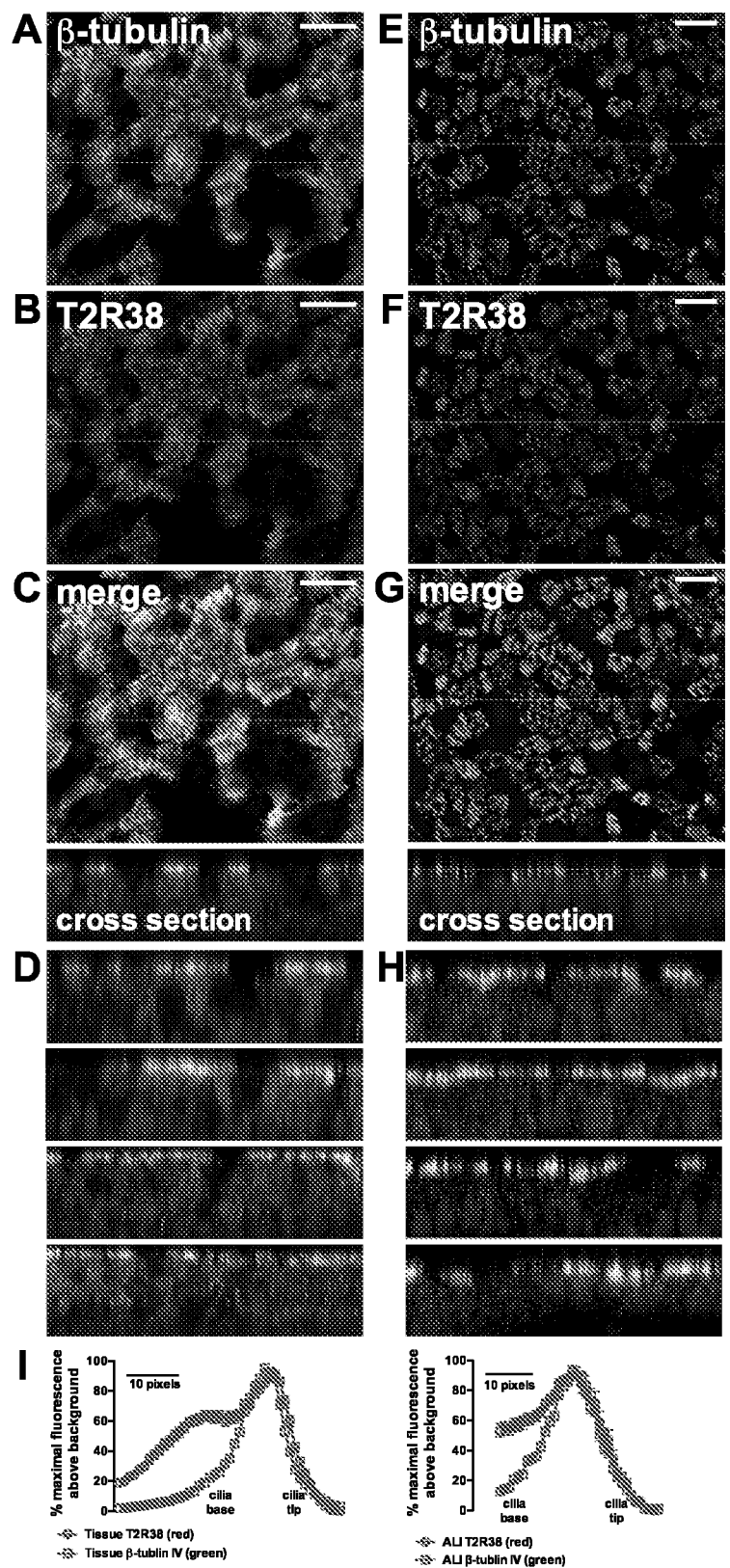
FIG. 15 shows that T2R38 is expressed at the apical membrane and cilia of sinonasal airway epithelial cells in both human tissue explants and primary human sinonasal airway liquid interface (ALI) cultures. (A-H) Representative images of β-tubulin (green; a ciliary marker), T2R38 (red), and Hoechst (blue; a nuclear stain) in primary human sinonasal tissue (A-D) and in a human sinonasal ALI culture (E-H). Scale bar is 20 µm in both. The height of the cross-section at the bottom is stretched to illustrate co-localization pattern. D and H show cross section Z-projections from 4 other tissue samples (D) and cultures (H) illustrating co-localization pattern. (I) 32 regions of ciliated cells were analyzed for red and green fluorescence (left to right represents basolateral to apical) over ~40 pixels.

T2R38 expression was observed in the apical membrane and cilia of sinonasal respiratory epithelial cells from surgical explants as well as primary sinonasal ALI cultures (FIG. 15). The green (β-tubulin IV, a cilia marker) and red (T2R38) fluorescence intensities were analyzed along 32 regions of cilia from Z-axis projections of tissue (FIG. 15D; 4 samples analyzed) and cultures (FIG. 15H; 8 cultures analyzed). In both tissue and cultures, red fluorescence (T2R38 expression) began at the tip of the cilia, and persisted below the base of the cilia, perhaps reflecting T2R38 in the process of trafficking to the plasma membrane. The Manders correlation coefficient for green staining was 0.96±0.02 and 0.99±0.01 in tissue and ALI cultures, respectively, indicating that >96% of green pixels (cilia) were positive for red staining (T2R38). Overall, these data show that T2R38 is expressed along the entire length of the cilia in both tissue and ALI cultures.

T2R5 are metabotropic G-protein-coupled receptors that can signal through intracellular $Ca^{2+}$. T2R stimulation (but not T2R38) has been shown to activate $Ca^{2+}$ signaling in human bronchial epithelial cells as well as rodent nasal solitary chemosensory cells. We thus tested if the T2R38-specific agonist PTC elevated $Ca^{2+}$ in sinonasal epithelial cells, using the fluorescent calcium indicator Fluo-4. Apical (air-side) stimulation with 1 mM PTC, induced low-level, sustained $[Ca^{2+}]_i$ elevations (FIG. 16A) in the majority of cells, demonstrating functionality of T2R38, while basolateral stimulation or vehicle alone had no effect. Notably, the magnitudes of PTC-induced $Ca^{2+}$ changes were a function of TAS2R38 genotype (FIG. 16A-B). Cultures derived from tasters (PAV/PAV) exhibited the greatest response, while cultures from non-tasters (AVI/AVI) and heterozygous individuals (PAV/AVI) had nearly undetectable responses. In contrast, purinergic-receptor-dependent ATP-induced $Ca^{2+}$ responses did not correlate with TAS2R38 genotype (FIG. 16A-B) and RT-PCR for TAS2R38 from genotypically distinct cultures demonstrated comparable levels of expression. Likewise, immunofluorescence demonstrated comparable T2R38 expression between PAV/PAV and AVI/AVI cultures. This indicates that the reduced PTC-induced $Ca^{2+}$ responses in heterozygous (PAV/AVI) and homozygous non-functional (AVI/AVI) derived cultures are due to differential activation of the T2R38 protein and not intrinsic defects in $Ca^{2+}$ signaling or differential expression. T2R38-activated $Ca^{2+}$ signaling was reduced by inhibition of PLCβ2, the inositol-trisphosphate ($IP_3$) receptor, or TRPM5, downstream components of receptor signaling in taste cells. These data indicate that T2R38 is expressed in human upper airway epithelium and that homozygosity for the TAS2R38 functional genotype (PAV) is required for maximal T2R38 signal propagation in sinonasal respiratory epithelial cells.

T2R38 Detects Gram-Negative Quorum Sensing Molecules.

Murine nasal chemosensory cells express bitter taste signaling molecules and detect *Pseudomonal* quorum sensing molecules. Thus we tested whether these bacterial products activate $Ca^{2+}$ signaling in human sinonasal epithelial cells and whether such activation was dependent upon TAS2R38 genotype. Cultures were stimulated with the gram-negative quorum sensing molecule N-butyryl-L-homoserine lactone (C4HSL) at 200 μM, or N-3-oxo-dodecanoyl-L-homoserine lactone (C12HSL) at 100 μM, physiological HSL concentrations observed during late stationary planktonic phase and biofilm growth. Both C12HSL and C4HSL are produced by the important respiratory pathogen *Pseudomonas aeruginosa* as well as other gram-negative bacteria, which may use these molecules for interspecies communication to form mixed biofilms on the airway epithelium. Cultures derived from individuals homozygous for functional T2R38 (PAV/PAV) had a significantly greater $Ca^{2+}$ response to the HSLs compared with those homozygous or heterozygous for the non-functional receptor (AVI/AVI or PAV/AVI, respectively) (FIG. 16C-F). N-Hexanoyl-L-homoserine lactone (C6HSL), produced by some *P. aeruginosa*, *B. cenocepacia*, and *B. multivorans* strains, also produced $Ca^{2+}$ responses that were greater in PAV/PAV cultures than in AVI/AVI culture that were blocked by PLCβ2 inhibition. Application of three concentrations (6.25%, 12.5%, 25%) of conditioned medium from a 3-day biofilm culture of *Pseudomonas aeruginosa* (strain PAO1) to ALI cultures with functional T2R38 receptors also elicited $Ca^{2+}$ responses that were blocked by inhibition of PLCβ1. Sequential addition experiments using high concentrations of PTC (15 mM) and C4HSL (400 μM) supported that these 2 agonists activate $Ca^{2+}$ signaling through a common pathway. Supporting this, siRNA knockdown of TAS2R38 expression significantly reduced the C4HSL and C12HSL-induced $Ca^{2+}$ responses observed in PAV/PAV cultures, indicating this receptor is a critical component of airway signaling in response to HSLs.

The onset of the $Ca^{2+}$ responses to PTC, C4HSL, and C12HSL occurred within one time point (5 sec) after addition of the compounds 90% of the time and within 2 frames (10 sec) 10% of the time. These fast responses indicate that this $Ca^{2+}$ elevation is a result of direct receptor activation rather than a secondary response of another compound secreted or released in response to C4/C12HSL.

To definitively test if T2R38 is directly activated by C4HSL and C12HSL, the PAV and AVI variants of human TAS2R38 (hTAS2R38) were cloned from PAV/PAV and AVI/AVI homozygous individuals and expressed in HEK293 cells co-transfected with a chimeric G protein Gα16gustducin44 to couple receptor activation to calcium mobilization. This expression system has previously been used to study T2R38, and it has shown that both forms of the protein are targeted to the plasma membrane of HEK293 cells. Fluo-4 fluorescence was monitored during stimulation with 1 mM PTC, 200 μM C4HSL, and 100 μM C12HSL. The bitter T2R agonists denatonium (1 mM) and salicin (10 mM) were included as controls as they do not activate T2R38. PTC (1 mM), C4HSL (200 μM), and C12HSL (100 μM) all activated $Ca^{2+}$ signals in PAV-TAS2R38-expressing cells, but no response was observed in AVI-TAS2R38-expressing cells (FIG. 16G), strongly supporting the direct activation of T2R38 signaling by gram-negative bacterial HSLs. No significant $Ca^{2+}$ response was observed with salicin or denatonium, as expected.

Similarly to ALI cultures, $Ca^{2+}$ responses to PTC and C4HSL occurred in acutely dissociated sinonasal ciliated cells, indicating that the responses observed in the ALI cultures recapitulate the in vivo epithelial response. Together, these data show that T2R38 contributes to the detection of quorum sensing molecules from gram-negative bacteria in sinonasal epithelial cells, perhaps leading to downstream defense mechanisms that are reduced in subjects with at least one non-functional TAS2R38 allele (AVI).

T2R38 Activation Triggers Nitric Oxide (NO) Production.

Figure 17:
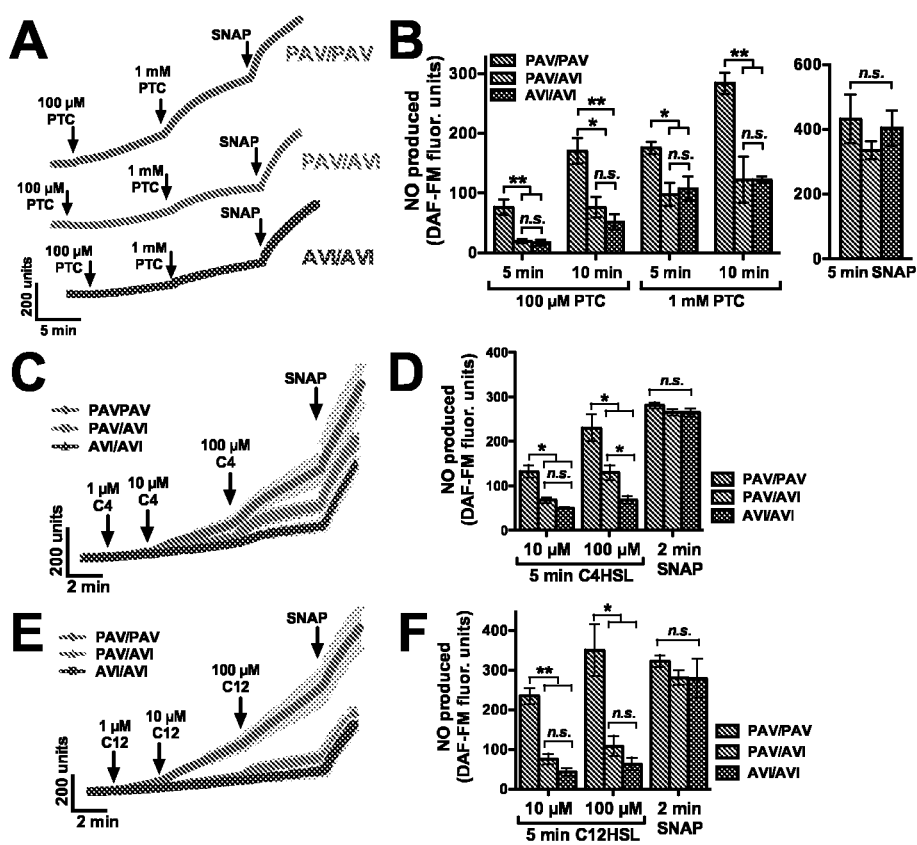
FIG. 17 shows that activation of T2R38 by PTC or *Pseudomonas* HSLs results in NO production. (A) Traces of DAF-FM fluorescence increases with PTC (1 culture each; ~100 cells; SEM smaller than symbols; representative of 9-12 cultures each). (B) DAF-FM fluorescence increases after PTC stimulation were: [100 μM; 5 min] 76±13 (PAV/PAV), 20±3 (PAV/AVI), and 17±5 (AVI/AVI), [100 μM; 10 min] 170±21 (PAV/PAV), 76±17 (PAV/AVI), and 52±13 (AVI/AVI), [1 mM; 5 min] 176±10 (PAV/PAV), 98±19 (PAV/AVI), and 107±20 (AVI/AVI), and [1 mM; 10 min] 285±18 (PAV/PAV), 123±38 (PAV/AVI;), and 122±5 (AVI/AVI). Increases after SNAP were not different between cultures of different genotypes. Each patient treated as independent observation; 4 patients each. (C) Average traces of DAF-FM with C4HSL (2 cultures each from 4 patients [8 total] for each genotype). (D) Results from C averaged by patient. Fluorescence increases after 5 min were [10 μM C4HSL] 132±14 (PAV/PAV), 68±6 (PAV/AVI), 50±2 (AVI/AVI) and [100 μM C4HSL] 230±30 (PAV/PAV), 130±17 (PAV/AVI, and 69±8 (AVI/AVI). (E) Average traces of DAF-FM with C12HSL (2 cultures each from 4 PAV/PAV patients [8 total] and 3 PAV/AVI and AVI/AVI patients [6 total for each]). (F) Results from E averaged as in D. Fluorescence increases after 5 min were [10 μM C12HSL] 235±20 (PAV/PAV), 77±13 (PAV/AVI), and 44±9 (AVI/AVI) and [100 μM C12HSL] 351±65 (PAV/PAV), 109±25 (PAV/AVI), and 64±16 (AVI/AVI). Increases after SNAP were not different. For B, D, and F, *P<0.05, **P<0.01 by ANOVA (Tukey-Kramer post-test).

Because the above data indicate that T2R38 plays a role in the detection of gram-negative bacteria by respiratory epithelial cells, we hypothesized that T2R38-induced $Ca^{2+}$ responses likely activate one or more known anti-microbial pathways. We found that T2R38 activation does not result in cytokine secretion (inflammation) or direct antimicrobial peptide secretion over the course of 12-14 hours exposure. Additionally, we found no significant difference in cytokine secretion between PAV/PAV and AVI/AVI cultures stimulated with *Pseudomonas* lippopolysaccharides (LPS; 10 μg/mL; a toll-like receptor [TLR]4 agonist), or the TLR 2/6 agonist FSL-1 (1 μg/mL), strongly supporting that T2R38 signaling is independent of TLR signaling and cytokine secretion. Another antimicrobial pathway is NO, which can be generated by low-level $[Ca^{2+}]_i$ changes that stimulate calmodulin-dependent nitric oxide synthase (NOS) activation. We measured cellular NO production using the fluorescent probe 4-amino-5-methylamino-2',7'-difluorescein (DAF-FM) which reacts with NO-derived reactive nitrogen species (RNS) to form a fluorescent benzotriazole. PTC (100 μM and 1 mM) stimulation resulted in NO-derived reactive species production (DAF-FM fluorescence) over the course of 10 minutes (FIG. 17A-B). Furthermore, DAF-FM fluorescence increase was a function of T2R38 genotype, with PAV/PAV cultures exhibiting greater responses than either PAV/AVI or AVI/AVI cultures. Exposure to the NO donor S-Nitroso-N-Acetyl-D,L-Penicillamine (SNAP; 100 μM; FIG. 17A-B) or ionomycin did not yield differential DAF-FM responses between the genotypes, indicating that differences in PTC-induced DAF-FM fluorescence were not an artifact of differential dye loading or NOS activity. PTC-dependent NO production was inhibited by blocking PLCβ2 or downstream $Ca^{2+}$ signaling. Another T2R38 agonist, sodium thiocyanate (NaSCN) activated similar T2R38-dependent DAF-FM fluorescence that was blocked by the NOS inhibitor L-N$^G$-Nitroarginine methyl ester (L-NAME), despite no effect on T2R38-activated $Ca^{2+}$ signaling. Two other bitter taste ligands, thujone (5 mM) and denatonium (10 mM), which activate multiple T2R5 but not T2R38, did not stimulate NO production indicating that T2R38 functionality is specifically critical for upper respiratory epithelial NO production in response to bitter compounds.

Figure 16:
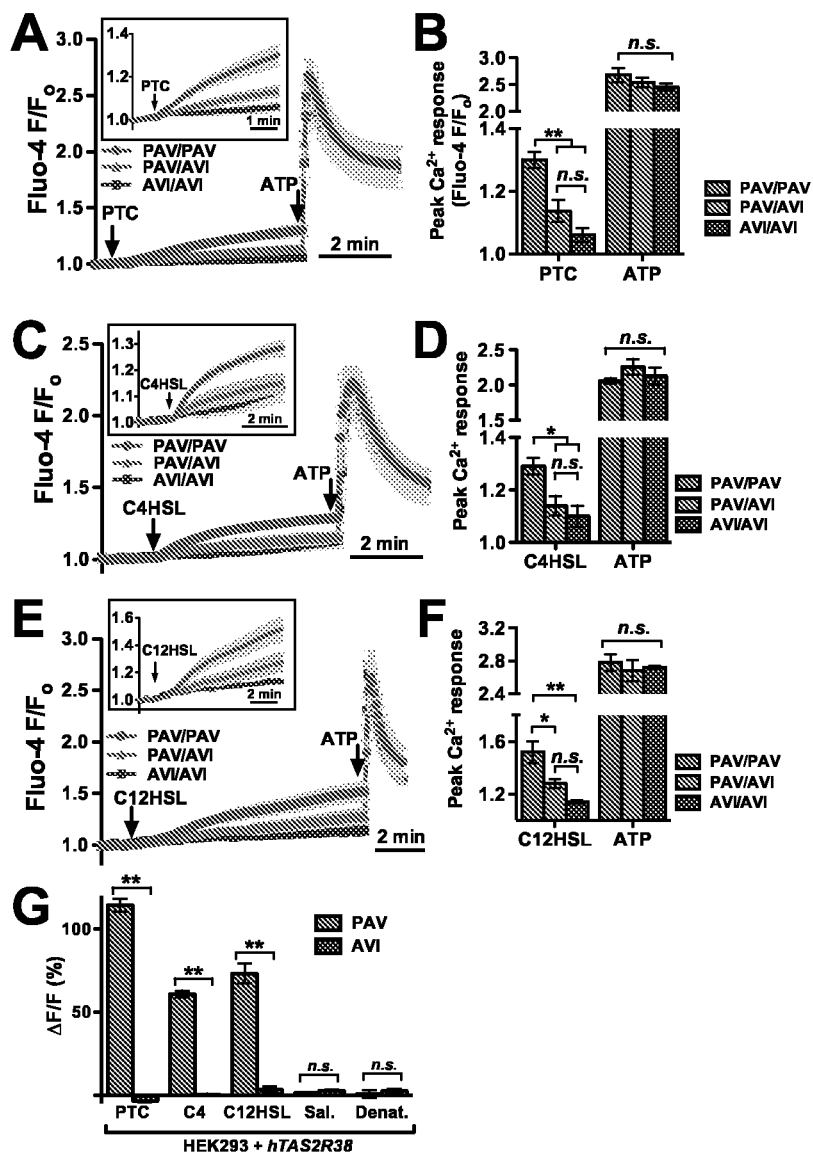
FIG. 16 shows that PTC and *Pseudomonas* homoserine lactones induce T2R38-dependent $Ca^{2+}$ responses in sinonasal ALIs and a heterologous expression system. (A) Fluo-4 traces illustrating $Ca^{2+}$ responses to PTC (1 mM) and ATP (1 µM) stimulation (mean±SEM of 12 PAV/PAV, 16 PAV/AVI, and 8 AVI/AVI cultures; 4 patients each). Inset shows PTC responses on a larger scale. (B) Peak $Ca^{2+}$ responses from A. Results from individual patients were pooled and averaged; bar graph represents each patient as one independent observation. Fluo-4 fluorescence after 5 min PTC was 1.30±0.027 (PAV/PAV), 1.14±0.035 (PAV/AVI), and 1.06±0.02 (AVI/AVI). (C) Fluo-4 traces (each is mean of 10 cultures; 5 patients per genotype; 2 cultures per patient) during stimulation with 200 μM C4HSL and ATP. (D) Peak $Ca^{2+}$ responses from C; averaged as in B. Fluo-4 fluorescence after 5 min C4HSL was 1.29±0.03 (PAV/PAV), 1.14±0.04 (PAV/AVI), and 1.10±0.04 (AVI/AVI). (E-F) Experiments performed as in C-D using 100 μM C12HSL. Three cultures from 3 patients (9 total) per genotype were used. Fluo-4 fluorescence after 10 min C12HSL stimulation was 1.52±0.08 (PAV/PAV), 1.28±0.04 (PAV/AVI), and 1.14±0.01 (AVI/AVI). (G) Bar graph showing peak Fluo-4 fluorescence (ΔF/F) in hTAS2R38- and Gα16gustducin44-expressing HEK293 cells in response to PTC (114±4% PAY; −4±1% AVI), C4HSL (61±2% PAY; 0.3±0.4% AVI), and C12HSL (73±5% PAY; 3±2% AVI), denatonium (1±2% PAY; 3±1% AVI), and salicin (1.4±0.3% PAY; 3±1% AVI). P values derived from ANOVA (Tukey-Kramer post-test); *P<0.05,**P<0.01.

Because sinonasal ALIs stimulated with either *Pseudomonas* conditioned medium or with purified HSLs exhibited T2R38-dependent $Ca^{2+}$ responses, we tested whether homoserine lactones activate T2R38-dependent NO production. C4HSL (10-100 µM) produced an increase in DAF-FM fluorescence that was significantly larger in cultures with functional receptors (PAV/PAV) compared with cultures with non-functional T2R38 (AVI/AVI) (FIG. 17C-D) that was blocked by inhibition of NOS or PLCβ1. Additionally, siRNAs directed against TAS2R38 expression significantly decreased the NO response to C4HSL. Likewise, T2R38 genotype-dependent NO production was elicited with C12HSL (10 µM and 100 µM) (FIG. 17E-F) and was blocked by anti-TAS2R38 siRNAs. Notably, at equal concentrations, C12HSL generated more NO than C4HSL (FIG. 17C-D), agreeing with its slightly greater potency as a T2R38 agonist (FIG. 16G; note that C4HSL concentration used in FIG. 16 is 2-fold greater than C12HSL concentration). Diluted *Pseudomonas* conditioned medium (6.25%) also activated an NO response. NO production was not observed when epithelial cells were stimulated with diluted conditioned-medium from a strain that does not produce C4HSL and C12HSL (PAO-JP2) or with *Pseudomonas* LPS (10 µg/mL) or FSL-1 (1 µg/mL), indicating that this is a specific response to quorum sensing molecules. We observed similar DAF-FM fluorescence increases when acutely dissociated sinonasal ciliated epithelial cells were stimulated with the T2R38 agonists PTC, NaSCN and acetylthiourea (ATU), as well as C4HSL. This strongly indicates that the responses we observe in ALI cultures reflect physiological responses in vivo.

T2R38 Increases Mucociliary Transport Velocity.

Figure 18:
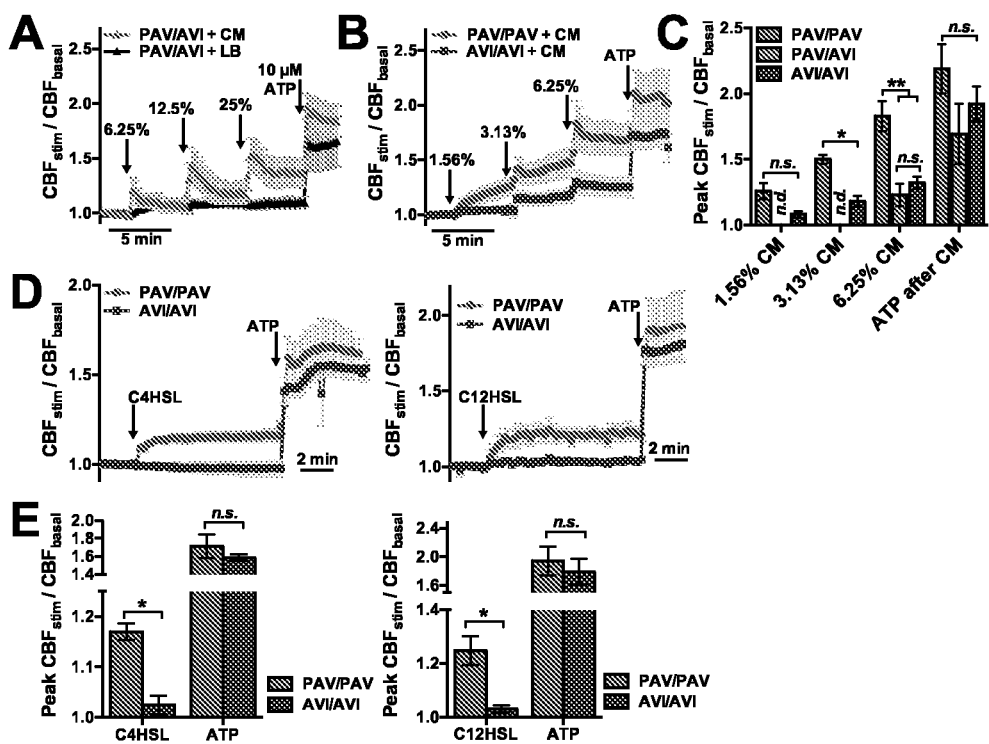
FIG. 18 shows that *Pseudomonas*-conditioned media (CM) and homoserine lactones stimulate an increase in CBF that requires T2R38 function. (A) Average traces showing CBF increase in PAV/AVI cultures stimulated with CM or LB as well as ATP. (B) Average traces showing effects of 3 concentrations of CM on CBF in PAV/PAV taster (n=9 cultures from 3 patients) and AVI/AVI non-taster cultures (n=11 cultures from 3 patients). (C) Summary of A-B treating each patient as an independent observation (n=3 each; n.d.=not determined). CBF increased to 1.26±0.6 (PAV/PAV) and 1.08±0.2 (AVI/AVI; n.s.) with 1.56% CM, 1.50±0.03 (PAV/PAV) and 1.18±0.04 (AVI/AVI; P=0.03) with 3.13% CM, and 1.83±0.11 (PAV/PAV), 1.23±0.09 (PAV/AVI; P<0.01 vs PAV/PAV), and 1.32±0.05 (AVI/AVI; P<0.01 vs PAV/PAV; n.s. vs PAV/AVI) with 6.25% CM. Peak CBF after ATP stimulation was not significantly different between cultures of different genotypes. (D) Average traces showing peak CBF in response to 200 μM C4HSL and 100 μM C12HSL in PAV/PAV and AVI/AVI cultures (n=6 each from 3 patients). (E) Summary of results from D, treating each patient as an independent observation (3-4 each). Peak CBF with C4HSL was 1.17±0.02 (PAV/PAV) and 1.02±0.02 (AVI/AVI) and with C12HSL was 1.25±0.05 (PAV/PAV) and 1.03±0.01 (AVI/AVI). *P<0.05, **P<0.01 (ANOVA with Tukey-Kramer post-test).

Mucociliary clearance (MCC) is the primary physical defense of the respiratory system. Because NO has been previously linked to elevation of CBF, we examined whether *Pseudomonas*-conditioned medium or purified homoserine lactones stimulated CBF in a T2R38-dependent and/or NO-dependent fashion. Following a frequently used convention, changes in CBF are normalized to the basal rate and reported as a ratio of stimulated/basal frequencies. No differences in baseline or ATP-stimulated CBF were observed between cultures with functional or non-functional T2R38 receptors, and none of the inhibitors used in this study had a significant effect on basal CBF. We found that dilute *Pseudomonas* biofilm-conditioned media increased CBF in sinonasal ALI cultures in a dose-dependent fashion (FIG. 18A). This stimulation was significantly greater in cultures with the functional (PAV/PAV) T2R38 receptors compared to cultures with the non-functional receptors (AVI/AVI) or heterozygote cultures (PAV/AVI) (FIG. 18B-C). In PAV/PAV cultures, CBF elevation in response to 6.25% *Pseudomonas* medium was blocked by inhibition of either PLCβ2 or NOS. Conditioned-medium from PAO1 planktonic cultures likewise activated a T2R38-dependent increase in CBF at dilute concentrations, while culture medium from PAO-JP2 (C4HSL- and C12HSL-deficient) had minimal effect on CBF and exhibited no difference between PAV/PAV and AVI/AVI cultures. As a control, culture supernatant from a flagellin mutant (Sad36; flgk) yielded similar results to wild type PAO1 medium. We hypothesized that T2R38 functions to detect HSLs secreted by *Pseudomonas* and other gram-negative bacteria into the airway surface liquid environment. When PAO1 bacteria were resuspended in PBS+0.5 mM glucose (to simulate airway surface liquid), the resulting conditioned PBS stimulated CBF increases after as little as 30 min. PAO1-conditioned PBS that was dialyzed to remove low molecular weight (<3.5 kDa) compounds as well as PAO-JP2-conditioned PBS had no effect on CBF while the Sad36-conditioned PBS retained stimulatory capacity. Not surprisingly, C4HSL and C12HSL similarly induced a T2R38-dependent increase in CBF (FIG. 18D-E). HSL-stimulated CBF increase was blocked by L-NAME but not the inactive D-NAME, as well as various inhibitors of NO signaling, including the soluble guanylyl cyclase inhibitor LY83583 and the protein kinase G (PKG) inhibitors KT5823 and H8. These findings demonstrate an important role for T2R38 in NO-dependent ciliary responses to secreted factors from gram-negative bacteria.

Figure 19:
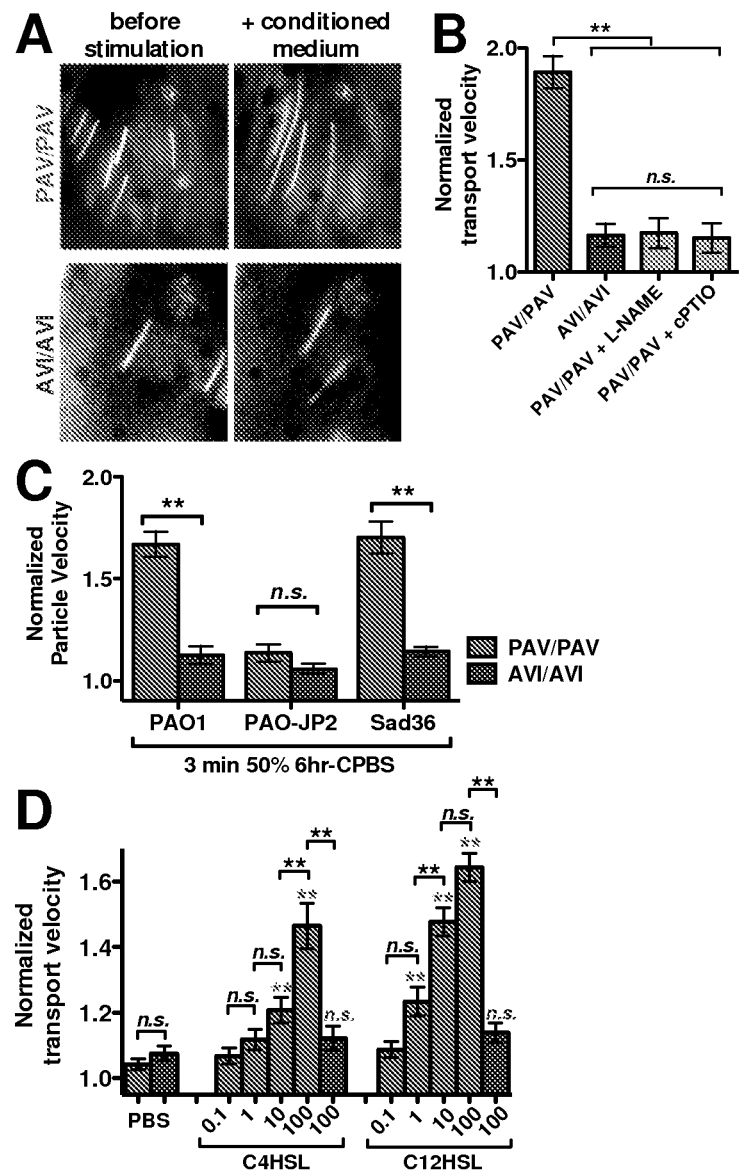
FIG. 19 shows that *Pseudomonas*-conditioned media (CM) and homoserine lactones stimulate an T2R38-dependent NO-dependent increase in mucociliary clearance. (A) Representative images of particle streaks taken immediately before (left) and ~3 min after (right) stimulation with 6.25% biofilm-CM in cultures from PAV/PAV (top) and AVI/AVI (bottom) patients. (B) Mean normalized velocity increase was 1.9±0.07 (PAV/PAV; n=10 cultures from 3 patients), 1.16±0.05 (AVI/AVI; n=9 cultures from 3 patients), 1.17±0.07 (PAV/PAV+L-NAME; n=6 cultures from 3 patients), and 1.15±0.07 (PAV/PAV+cPTIO; n=6 cultures from 3 patients). (C) Results from transport analysis using conditioned PBS (CPBS; 6 hrs) from PAO1, PAO-JP2, and Sad36 strains (4 cultures per genotype per strain). Normalized velocity increases were [PAO-1] 1.67±0.06 (PAV/PAV) vs 1.13±0.04 (AVI/AVI), [PAO-JP2] 1.135±0.04 (PAV/PAV) vs 1.058±0.03 (AVI/AVI), and [Sad36] 1.703±0.08 (PAV/PAV) vs 1.14±0.03 (AVI/AVI). (D) Results from transport analysis using C4HSL and C12HSL. Increases in velocity upon addition of PBS (control) were 1.04±0.02 (PAV/PAV) vs 1.08±0.2 (AVI/AVI). After addition of C4HSL, increases were 1.07±0.02 (0.1 μM; PAV/PAV), 1.12±0.03 (1 μM; PAV/PAV), 1.21±0.04 (10 μM; PAV/PAV), 1.47±0.07 (100 μM; PAV/PAV), and 1.12±0.03 (100 μM; AVI/AVI). After addition of C12HSL, increases were 1.09±0.02 (0.1 μM; PAV/PAV), 1.23±0.04 (1 μM; PAV/PAV), 1.48±0.04 (10 μM; PAV/PAV), 1.64±0.04 (100 μM; PAV/PAV), and 1.14±0.03 (100 μM; AVI/AVI). Blue and red symbols represent significance compared with PBS addition to isogenic cultures; black asterisks represent significance between the bracketed pairs; *P<0.05, **P<0.01 (ANOVA; Tukey-Kramer post-test).

To confirm that an increase in CBF yielded an increase in MCC, we measured the transport velocity of fluorescent microspheres on sinonasal ALI cultures. Cultures were washed with PBS to remove large mucus particles, and 2 µm fluorescent microspheres were overlaid onto the culture. Bead transport was imaged using 2 or 5 sec exposures (depending on the baseline transport rate of each culture). The length of the imaged streak reflected the distance traveled during the exposure period and thus could be used to extrapolate relative velocity changes within each experiment. Ten frames were recorded at baseline, and a subsequent 10 frames were recorded 3 minutes after addition of *Pseudomonas* conditioned media to a final concentration of 6.25% (the field of view was unchanged; the 3 min post-addition was necessary to ensure microspheres had settled after the fluid addition). Frames from experiments using cultures from functional (PAV/PAV) and non-functional (AVI/AVI) T2R38 receptors are shown in FIG. 19A. Cultures homozygous for the functional form of the T2R38 receptor exhibited a ~1.9 fold increase in streak length (reflecting transport velocity) following application of pseudomonas CM while non-functional T2R38 cultures exhibited minimal increases, as did functional cultures treated with L-NAME or the NO scavenger carboxy-PTIO (FIG. 19B). Additionally, conditioned PBS (CPBS) from PAO-1, PAO-JP2, and Sad36 strains were tested in this assay. We found that PAO-1 and Sad36 CPBS activated mucociliary transport in PAV/PAV but not AVI/AVI cultures (FIG. 19C). In contrast, CPBS from the HSL-deficient PAO-JP2 did not significantly increase transport velocity in cultures of either genotype (FIG. 19C). When C4HSL and C12HSL were directly tested in this assay (FIG. 19D), we found that C12 was more potent that C4HSL, as C12HSL significantly increased mucociliary transport at a concentration (1 µM) one order of magnitude below the concentration of C4HSL (10 µM) required to stimulate a significant increase in transport. This result agrees with the general trend observed in intracellular NO production in response to C4HSL and C12HSL (FIGS. 17C and E). These data demonstrate that detection of bacterial quorum sensing molecules by T2R38 results in activation of intracellular $Ca^{2+}$ and NO signaling pathways resulting in enhanced MCC.

T2R38 Activation in Upper Respiratory Epithelial Cells Results in NO Diffusion into the Airway Surface Liquid (ASL).

Figure 20:
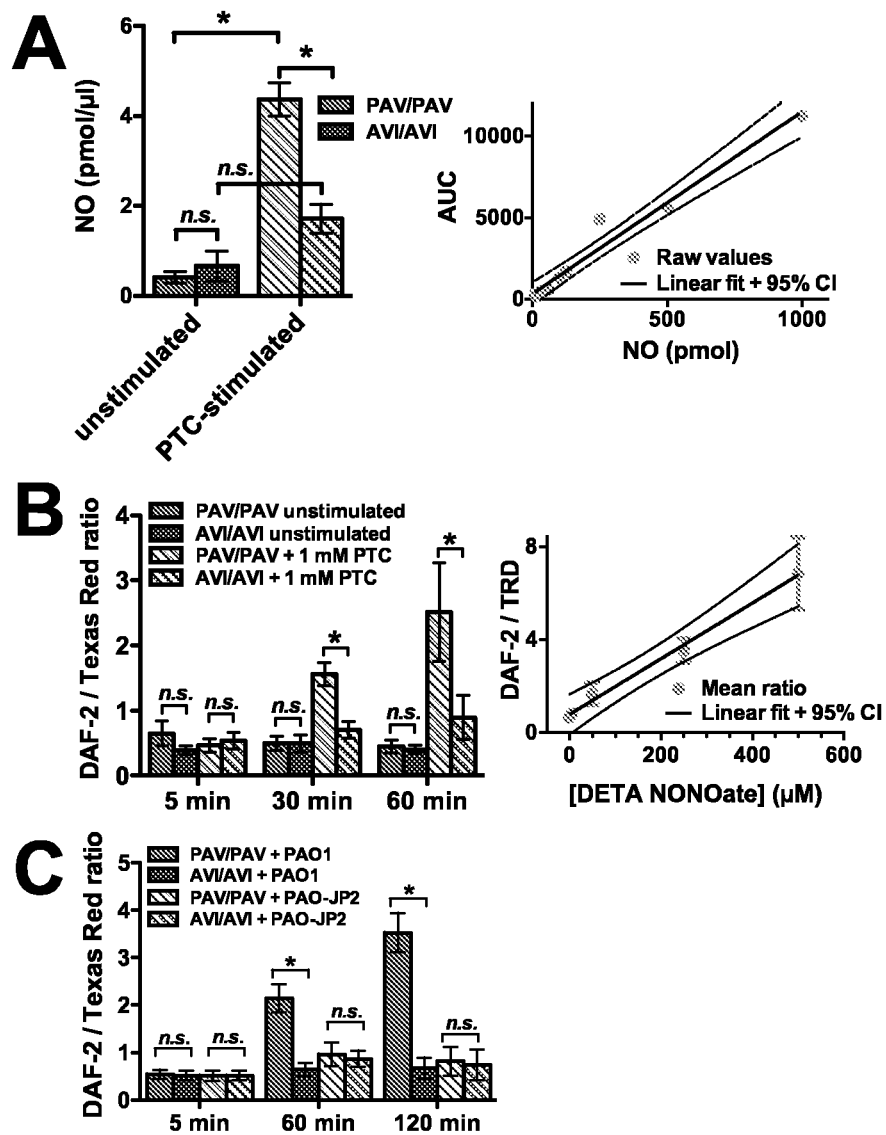
FIG. 20 shows that human sinonasal ALI cultures exhibit T2R38-dependent apical NO diffusion. (A) NO metabolites were quantified from ASL (1 stimulated and 1 unstimulated culture used from 4 PAV/PAV and 3 AVI/AVI patients each; left graph). Right graph shows calibration using known $NaNO_3$ standards. (B) Fluorescence ratios of DAF-2 and Texas Red Dextran (TRD) were used to measure NO secretion (left graph). There was no change in ratios for unstimulated PAV/PAV or AVI/AVI cultures (sold bars; 0.65±0.19 [PAV/PAV] and 0.39±0.07 [AVI/AVI] at 5 min, 0.50±0.11 [PAV/PAV] and 0.50±0.10 [AVI/AVI] at 30 min, and 0.45±0.10 [PAV/PAV] and 0.41±0.06 [AVI/AVI] at 60 min. In contrast, PAV/PAV and AVI/AVI cultures had marked differences after PTC stimulation (0.46±0.10 [PAV/PAV] and 0.54±0.1 [AVI/AVI] at 5 minutes, 1.55±0.17 [PAV/PAV] and 0.71±0.1 [AVI/AVI] at 30 min, and 2.52±0.76 [PAV/PAV] and 0.90±0.3 [AVI/AVI] at 60 min). Right graph shows addition of 0, 5, 50, 250, and 500 μM DETA NONOate, resulting in a linear increase in DAF-2/TRD ratio. (C) Exposure to Wt, but not HSL-deficient *Pseudomonas* induced T2R38-dependent NO secretion. DAF2/Texas red ratios after exposure to PAO1 were 0.5±0.1 (PAV/PAV) and 0.5±0.1 (AVI/AVI) at 5 min, 2.1±0.3 (PAV/PAV) and 0.6±0.1 (AVI/AVI) at 60 min, and 3.5±0.4 (PAV/PAV) and 0.7±0.2 (AVI/AVI) at 120 min Ratios after exposure to PAO-JP2 were 0.5±0.1 (PAV/PAV) and 0.5±0.1 (AVI/AVI) at 5 min, 1.0±0.2 (PAV/PAV) and 0.9±0.1 (AVI/AVI) at 60 min, and 0.8±0.3 (PAV/PAV) and 0.7±0.3 (AVI/AVI) at 120 min. *P<0.05, **P<0.01 (ANOVA; Tukey-Kramer post-test).

The antibacterial properties of NO help maintain the sterility of the sinonasal airways. Thus, in addition to identifying the intracellular pathways downstream of NO generation, we tested if T2R38-induced NO production resulted in detectable diffusion of NO across the apical membrane into the ASL of sinonasal cultures. NO diffusion into the ASL was quantified by measuring NO-derived byproducts in 20 μL of airway surface liquid from cultures stimulated with 1 mM PTC (or PBS alone) for 20 min using reductive chemistries coupled with chemiluminescence detection of nitric oxide (FIG. 20A). ASL levels of NO metabolites (nitrate, nitrite, N-nitroso and iron-nitrosyl adducts as well as low molecular weight and protein S-nitrosothiol adducts) were not different in unstimulated PAV/PAV and AVI/AVI cultures (0.41±0.13 pmol/μL for PAV/PAV and 0.66±0.33 for AVI/AVI; n.s. vs PAV/PAV). However, the increase observed in PTC-stimulated PAV/PAV cultures was >2-fold larger than that observed in AVI/AVI cultures (FIG. 20A). In PTC stimulated cultures, NO metabolites in the ASL over 20 minutes were 4.37 pmol/μL (PAV/PAV; P<0.001 vs unstimulated PAV/PAV) and 1.72 pmol/μL (AVI/AVI; P<0.01 vs stimulated PAV/PAV; n.s. vs unstimulated AVI/AVI).

We also utilized a fluorescence-based assay to measure NO diffusion into the ASL. The apical surface of cultures was overlaid with a small volume (10 μl) of phosphate-buffered saline with or without 1 mM PTC containing 2 spectrally distinct cell-impermeant dyes, the NO-sensitive 4,5-diaminofluorescence diacetate (DAF-2) and the NO-insensitive Texas Red dextran (10,000 kDa MW); a ratiometric measurement was used to eliminate any artifacts due to expansion or contraction of ASL volume. The ratio of DAF-2/Texas Red fluorescence was recorded by fluorescence microscopy after 5, 30 and 60 min incubations at 37° C. The greater increase in DAF-2/Texas Red ratio in PTC-stimulated but not unstimulated PAV/PAV cultures compared with AVI/AVI cultures (FIG. 20B) further demonstrates that NO diffused into the ASL in a T2R38-dependent manner. We utilized this assay to determine if exposure to *Pseudomonas* and their secretions was sufficient to cause epithelial cells to produce NO with subsequent diffusion into the ASL. Log-phase cultures of PAO1 and PAO-JP2 were resuspended in PBS and placed on the ALI surface in the presence of DAF-2 and Texas Red. Exposure to PAO1 over 60-120 min, but not PAO-JP2, resulted in NO diffusion into the ASL in PAV/PAV but not AVI/AVI cultures (FIG. 20C), indicating that this is a physiological response to bacterial secretion of HSLs into the airway surface liquid. Together, these data indicate that PAV/PAV individuals may have enhanced sinonasal NO production compared with PAV/AVI and AVI/AVI individuals during respiratory challenge with *Pseudomonas* or other gram-negative bacteria.

T2R38-Dependent NO Production Directly Contributes to Epithelial Innate Defense.

We developed an assay to test if T2R38-activated NO production could directly result in or enhance epithelial bactericidal activity. ALI cultures were inoculated with planktonic (0.1 OD) *Pseudomonas* (PAO-1) in conditioned saline (60 min; as described above). After 2 hours of exposure to the ALI culture, bacteria were stained with a live/dead (green/red) stain to determine the percentage of viable (green) cells. As a control, bacteria in saline that were not exposed to an ALI culture exhibited nearly 100% green fluorescence whereas bacteria exposed to the antibiotic colistin exhibited nearly 100% red fluorescence. PAV/PAV cultures exposed to strain PAO-1 exhibited marked bacterial killing (FIG. 21A), while PAV/AVI and AVI/AVI cultures exhibited severely reduced bactericidal activity (FIG. 21A). This bacterial killing required NO, as it was inhibited by basolateral L-NAME pre-treatment or addition of cPTIO. Significantly reduced killing was also observed when the HSL-deficient strain PAO-JP2 was used on PAV/PAV or AVI/AVI cultures, but addition of C4HSL (10 μM) and C12 HSL (10 μM) to PAO-JP2-conditioned saline restored the potent antibacterial activity of PAV/PAV but not AVI/AVI cultures. These results are summarized in FIG. 21B. Taken in total, our data show that individuals with the PAV/PAV TAS2R38 genotype have an increased capacity to detect, clear, and kill sinonasal gram-negative bacteria compared with PAV/AVI and AVI/AVI individuals, which should manifest in less gram-negative infections in PAV/PAV individuals.

Reduced T2R38 Functionality Correlates with Gram-Negative Airway Infection.

To determine whether the above in vitro results have clinical significance, TAS2R38 was genotyped in patients who had undergone sinonasal surgery for various indications including chronic rhinosinusitis and pituitary pathology, for whom we had both tissue samples as well as microbiological laboratory reports from sinonasal swabs obtained at the time of surgery. We selected samples for TAS2R38 genotyping for which the microbiology report was either "No Growth/normal respiratory flora/coagulase negative staph", or isolated gram-negative bacteria. In this context, coagulase negative staph is considered either a commensurate nasal microbe or a contaminant from the nasal vestibule. We found a significant difference in the distribution of TAS2R38 functional and non-functional allele frequency between patients who exhibited no bacterial growth or normal respiratory flora (N.G. group) compared with patients who had positive gram-negative cultures (G.N. group) including *Pseudomonas aeruginosa* (P.A. group, a subpopulation of the G.N. group) (Table 2). The group of patients with sinonasal gram-negative bacteria had no subjects who were homozygous for the functional (PAV/PAV) form of TAS2R38 (P<0.0058 by chi-squared ($\chi^2$) analysis). The results were also significant when N.G. patients were compared with only P.A. patients (P<0.029). No significant differences were observed between the 2 groups when polymorphisms for 3 other bitter receptor genes were examined, namely TAS2R19, TAS2R30 (formerly known as TAS2R47), and TAS2R46 (Table 2). Some genotypes could not be unequivocally determined using allele-specific primers and probes probably due to the presence of copy number variants, and thus not all genotypes were reported for each patient. These genetic data support the clinical relevance of the in vitro physiological data described above, which show that T2R38 plays a role in respiratory epithelial defense against gram-negative bacteria, including the common respiratory pathogen *Pseudomonas*.

Our findings indicate that the GPCR T2R38, originally identified as a bitter taste receptor, is expressed in human sinonasal epithelial cells where it triggers a rapid inter-kingdom signaling response bridging microbial secretions and the human upper airway epithelium, making it an integral component of upper respiratory early response defenses. When stimulated by homoserine lactones (HSLs), T2R38 elicits calcium-dependent nitric oxide (NO) production that increases ciliary beat frequency and mucus clearance. Additionally, this NO diffuses into the airway and contributes to innate antimicrobial effects. We further demonstrate that upper airway epithelial cells from individuals with one or two nonfunctional T2R38 alleles have significantly blunted nitric oxide and ciliary responses following exposure to gram-negative quorum sensing molecules and that these individuals are more likely to be infected with gram-negative bacteria such as *Pseudomonas aeruginosa* than those with two functional receptor alleles.

TABLE 2

|  | TAS2R38[A] | | | TAS2R19[B] | | | TAS2R30[C] | | | TAS2R46[D] | | |
| --- | --- | --- | --- | --- | --- | --- | --- | --- | --- | --- | --- | --- |
|  | AVI/AVI | AVI/PAV | PAV/PAV | A/A | A/G | G/G | A/A | A/C | C/C | C/C | C/T | T/T |
| No Growth (N.G.) | 13 | 11 | 11 | 4 | 13 | 3 | 3 | 17 | 5 | 13 | 11 | 2 |
| gram-negative (G.N.) | 7 | 14 | 0 | 5 | 5 | 5 | 5 | 7 | 5 | 10 | 6 | 0 |
| *P. aeruginosa* (P.A.) | 5 | 9 | 0 | 4 | 5 | 2 | 2 | 7 | 4 | 7 | 5 | 0 |
| Total (N.G. + G.N.) | (20) | (25) | (11) | (9) | (18) | (8) | (8) | (24) | (10) | (23) | (17) | (2) |
| $\chi^2_{(2)}$ (N.G. vs G.N.) | 10.3 ($P < 0.0058$) | | | 3.5 ($P < 0.17$) | | | 3.3 ($P < 0.20$) | | | 1.6 ($P < 0.46$) | | |
| $\chi^2_{(2)}$ (N.G. vs P.A.) | 7.1 ($P < 0.029$) | | | 1.2 ($P < 0.54$) | | | 0.76 ($P < 0.68$) | | | 1.0 ($P < 0.60$) | | |

[A]Typed for polymorphisms A49P, V262A, and I296V (rs713598, rs1726866 and rs10246939; as described above)
[B]The putative quinine receptor, typed for rs10772420; receptors containing the A allele have a higher level of function than receptors containing the G allele (93).
[C]Formerly known as TAS2R47, typed for rs2708381
[D]Typed for rs2599404

Long-term exposure to *Pseudomonas* HSLs has been shown to have toxic effects in some airway cell lines. A reduced ability to rapidly detect and clear these molecules in PAV/AVI and AVI/AVI individuals may have profound disease implications. While HSL concentrations of >100 μM are only found in mature biofilms, the levels found in planktonic growth (pre-biofilm) cultures are still quite high and within the range of detection we observe in this study. C12HSL levels have been reported to be between 200 nM (early log phase) and 5 μM (early stationary phase) in planktonic laboratory cultures, while the level of C4HSL has been calculated at 10 μM in early stationary phase planktonic cultures. The T2R38-dependent detection of individual HSLs in the low μM range (FIG. 19) as well as the detection of secreted HSLs in CPBS after only 30 min suggests that the T2R38 system serves as mechanism to prevent infection and biofilm formation through early detection of HSLs and subsequent eradication of bacteria. This is supported by the clinical data presented demonstrating under representation of individuals homozygous for the functional T2R38 in patients harboring gram-negative sinonasal bacteria and warrants prospective studies to demonstrate the contribution of this pathway and these genetics in upper airway infection.

We observed that people with one functional and one nonfunctional allele of the T2R38 receptor (PAV/AVI) were more similar in their response to people with two nonfunctional copies (AVI/AVI), a pattern which varies from that observed for taste perception, where heterozygotes have a wide range of response but, on average, are more like the group with two functional receptor copies (PAV/PAV) and can readily detect PTC at low concentrations. It is possible that expressing just one non-functional allele leads to increases of intracellular $Ca^{2+}$ that are insufficient to activate NOS following T2R38 activation. It is also possible that there is differential allele expression with the AVI allele being overexpressed or silencing of the PAV allele.

In conclusion, our data show that T2R38 genotype represents a defining characteristic in respiratory innate defense that contributes to the complex genetic and environmental interactions predisposing to upper respiratory infections.

Example 6

Genetics of the Taste Receptor T2R38 Correlates with Chronic Rhinosinusitis Necessitating Surgical Intervention This study investigating the bitter taste receptor T2R38 demonstrates homozygote taster patients are less likely to need surgical intervention for chronic rhinosinusitis, compared to heterozygous or nontasters, and that homozygous tasters have improved surgical outcomes.

Materials and Methods

In an IRB approved study, banked sinonasal tissue samples from patients who had undergone primary (endoscopic sinus surgery) ESS at the University of Pennsylvania or the Philadelphia Veterans Affairs Medical Center were genotyped for T2R38. Inclusion criteria included any patient 18 years or older undergoing primary ESS at The Hospital of the University of Pennsylvania or Philadelphia Veterans Hospital. We excluded any patients with known autoimmune dysfunction, primary ciliary dyskinesia, cystic fibrosis, history of radiation exposure to the paranasal sinuses, or any history of sinonasal trauma.

Genomic DNA was isolated and each sample genotyped for TAS2R38. In addition, a retrospective chart review, with reviewers blinded to genotypes, was populated evaluating postsurgical outcomes measuring for postoperative infections requiring courses of antibiotics at both a 3 and 6-month follow up intervals. Statistical analysis with chi-squared analysis was performed using Stata 10 (Statacorp, College Station, Tex.).

Results

Within the banked samples that had been genotyped for T2R38 were 29 meeting the inclusion criteria for patients undergoing primary ESS. Of the 29, the distribution was 1 PAV/PAV, 15 PAV/AVI and 13 AVI/AVI. Chi-squared analysis demonstrates a statistically significant distribution variation from the published standard distribution of genotypes (P value <0.047). (Table 3).

TABLE 3

Distribution of actual and expected genotypes in 29 patients.

| Genotype | PAV/PAV | PAV/AVI | AVI/AVI |
| --- | --- | --- | --- |
| Distribution (%) | 1 (3.4) | 15 (51) | 13 (45) |
| Expected distribution (%) | 5.8 (20) | 14.5 (50) | 8.7 (30) |

P-value <0.047

Of the 29 initial patients 19 were seen 6 months following surgery. The one PAV/PAV genotype patient had not required any additional courses of antibiotics while three of nine of the PAV/AVI genotype (33%) and four of nine (44%) of the AVI/AVI genotype patients required at least one additional course of antibiotics (Table 4). The small sample size of taster variant (1 PAV/PAV) does not have the power for statistical significance.

TABLE 4

6-month follow up on genotypes evaluating for no clinical infections or clinical infection requiring 1 or more courses of antibiotics.

| Genotype | 0 Antibiotic courses | 1 or greater antibiotic courses |
|---|---|---|
| PAV/PAV | 1 | 0 |
| PAV/AVI | 6 | 3 |
| AVI/AVI | 5 | 4 |

Note the 1 taster (PAV/PAV) did not require further antibiotics at either the 3 or 6-month follow up.

T2R38 was initially identified through positional cloning studies exploiting human taste perception variability to the compound phenylhiocarbamide (PTC). Once cloned, the underlying genetic variability, i.e., polymorphisms, were identified to predominately reside at amino acid residues 49, 262, and 296, respectively, of the receptor. The functional allele of the receptor contains a proline, alanine and valine (PAV), while the nonfunctional allele of the receptor contains an alanine, valine, and isoleucine (AVI) at these respective positions.

We have shown expression of T2R38 in human sinonasal epithelium and demonstrated a novel defensive sentinel function for this receptor in combating gram-negative upper airway infection. Furthermore, we have also demonstrated that the T2R38 taster genotype (PAV/PAV) confers protection against gram-negative sinonasal infection, while the heterozygotes (PAV/AVI) and the non-taster genotype (AVI/AVI) are susceptible to gram-negative sinonasal infection.

We also show that patients with the PAV/PAV T2R38 genotype have a highly sensitive and effective sinonasal innate defense mechanism compared to PAV/AVI or AVI/AVI individuals that would be reflected in the paucity of surgical intervention in the management of chronic rhinosinusitis and decreased need for antimicrobial chemotherapy in the post operative patient.

We evaluated patients in which we performed the initial management and surgery since in many revision cases we were not involved in the medical decisions prior to the initial surgical intervention. In this group of patients we identified 1 (5.6%) taster variant (PAV/PAV) proceeding to surgery out of 29 patients (p>0.047). Published genotype distribution for tasters in the general population is approximately 20%.

We also evaluated this cohort for postsurgical clinical outcomes. There are a number of different criteria to discern when judging clinical results include validated outcomes scores, nasal endoscopy scores, cultures, and postoperative infections. In an attempt to stay consistent we only evaluated patients to identify if they required any additional course of antibiotics in the immediate 6-month postsurgical period (all our patients are routinely placed on two weeks of antibiotics postoperatively). Antibiotics were prescribed based on history and in most cases a physical examination including nasal endoscopy. Whenever possible culture-directed antibiotics were implemented.

Our findings have significant implications in the understanding of the pathophysiology and management of CRS. We have identified a genetic polymorphism that can confer an inherent weakness in sinonasal mucosa innate defense contributing to CRS necessitating surgical intervention. Patients at risk for medically recalcitrant CRS can be identified by a genetic test or even a surrogate real time and immediate taste test that in turn could lead to improved patient selection for ESS.

This study demonstrates that the genetics of T2R38 play a role in the progression of CRS necessitating surgical intervention.

Example 7

Treating Respiratory Tract Infections by 6-n-Propylthiouracil (PROP)

6-n-propylthiouracil (PROP) can be used as a therapeutic molecule to treat chronic rhinosinusitis and other respiratory tract infections. PROP is a bitter compound and a T2R38 agonist. Surprisingly and unexpectedly, it was found that PROP activates nitric oxide (NO) production in PAV/PAV (taster) sinonasal epithelial cells.

As with other T2R38 agonists, apical application of the T2R38-specific bitter compound 6-n-propylthio uracil (PTU or PROP) stimulated an increase in intracellular DAF-FM fluorescence (signaling increased nitric oxide and reactive nitrogen species production) in sinonasal epithelial cells as observed with PTC and NaSCN. See FIG. 24. NO production during stimulation with the non-specific NO donor S-nitroso-N-acetylpenicillamine (SNAP) is shown as a control. See FIG. 24.

Given the clinical experience with PROP (when given systemically), it can be a preferred therapeutic T2R38 stimulating compound. PROP and its pharmaceutical composition can be administered for use in a topical sinus lavage and/or spray.

Example 8

Treating Respiratory Tract Infections in AVI/AVI and PAV/AVI Patients by Quinine Quinine can be used as a therapeutic molecule to treat chronic rhinosinusitis and other respiratory tract infections. Quinine is a bitter agonist compound that activates T2R4, 7, 10, 14, 39, 40, 43, 44, and 46. See Meyerhof W, et al. *Chem Senses*, 2010, vol. 35(2), pages 157-70. Surprisingly and unexpectedly, it was found that quinine stimulates nitric oxide (NO) production in PAV/AVI heterozygote sinonasal epithelial cells.

As shown in FIG. 25, apical application of quinine (but not vehicle alone) stimulated a robust NO production (evidenced by increase in DAF-FM fluorescence) that was inhibited by the nitric oxide synthase (NOS) inhibitor L-NAME (20 µM).

Because quinine is not a T2R38 activator, quinine can be a useful therapeutic molecule because it can stimulate NO production in T2R38 non-tasters and heterozygotes (AVI/AVI and PAV/AVI) by activating other bitter receptors and bypassing the requirement for T2R38. The use of quinine can address the problem of T2R38-specific agonists from having substantial effects in AVI/AVI and PAV/AVI patients.

Example 9

Treating Respiratory Tract Infections in AVI/AVI and PAV/AVI Patients by *Antidesma bunius*

*Antidesma bunius* is a species of fruit tree in the Phyllanthaceae family. Extracts from *Antidesma bunius* berries and other parts can be used to treat chronic rhinosinusitis and other respiratory tract infections. *Antidesma bunius* berries have been previously reported to taste bitter to people who can't taste PTC (non-functional T2R38, e.g. AVI/AVI) and tastes sweet to people who can taste PTC (functional T2R38, e.g. PAV/PAV). See Henkin et al. Nature, 1977, vol. 265, pages 536-537.

Berry extracts or compounds contained within the berries can stimulate the AVI/AVI form of T2R38, making it a unique therapeutic to stimulate sinonasal AVI/AVI patients when given as a topical therapy. To date, no other known bitter agonist has the effect of enhanced bitter taste in AVI/AVI patients compared with PAV/PAV patients. The contents of this plant may activate one or more bitter receptors in AVI/AVI patients that could be useful as an NO producing therapeutic in AVI/AVI or PAV/AVI patients.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for treating an upper respiratory infection in the upper respiratory tract of a subject, the method comprising:
administering a bitter taste receptor agonist to the upper respiratory tract of the subject, wherein the bitter taste receptor agonist activates a bitter taste signal pathway that stimulates NO production in sinonasal epithelial cells of the upper respiratory tract of the subject, and wherein the bitter taste receptor agonist is selected from the group consisting of quinine and salts thereof, denatonium, absinthin, salicin, phenylthiocarbamide (PTC), a homoserine lactone, sodium thiocyanate (NaSCN) and 6-n-propylthio uracil (PROP); thereby stimulating an innate antimicrobial response that treats the upper respiratory tract infection in the subject.

2. The method of claim 1, wherein said bitter taste receptor agonist is selected from the group consisting of denatonium benzoate, absinthin and quinine and salts thereof.

3. The method of claim 1, wherein said upper respiratory infection is an acute or a chronic rhinosinusitis.

4. The method of claim 1, wherein the delivery mode of said agonist is selected from the group consisting of inhalants, nasal sprays, nasal drops, nasal ointments, nasal washes, nasal packings, bronchial sprays, and combination thereof.

5. The method of claim 1, wherein the delivery form of said agonist is selected from the group consisting of powders, crystalline substances, gels pastes, ointments, salves, creams, solutions, suspensions, partial liquids, liquid suspensions, sprays, nebulae, mists, atomized vapors, tinctures.

6. The method of claim 1, wherein said agonist is applied by lavage.

7. The method of claim 1, wherein said agonist comprises an ionic strength in the range of 150-200 mEq/L.

8. The method of claim 1, wherein said agonist is administered to the upper respiratory tract by a device selected from the group consisting of a bulb, an inhaler, a canister, a sprayer, a nebulizer, a metered-dose sprayer, and a mask.

9. The method of claim 1, wherein said agonist further comprises one or more antibiotics selected from the group consisting of Amikacin, Azithromycin, Aztreonan, Cefazolin, Cefepine, Cefonicid, Cefaperazone, Cefotaxime, Cefotetan, Cefoxitin, Ceftazidime, Ceftizoxime, Ceftriaxone, Cefuroxime, Cephapirin, Ciprofloxacin, Clindamycin, Doxycycline, Erythromycin Lactobionate, Gentamicin, Kanamycin, Linezolid, Mezlocillin, Mupirocin, Nafcillin, Netilmicin, Neomycin, Oxacillin, Paromomycin, Piperacillin, Streptomycin, Ticarcillin, Tobramycin, and Vancomycin.

10. A method for treating an upper respiratory infection associated disease or disorder and for stimulating an innate antimicrobial response by stimulating NO production in the upper respiratory tract of a subject, the method comprising: administering to the upper respiratory tract of said subject a therapeutically effective amount of a taste receptor, type 2, member 38 (T2R38) agonist that stimulates NO production in sinonasal epithelial cells of the upper respiratory tract of the subject so as to generate an innate antimicrobial response, and wherein the T2R38 agonist is selected from the group consisting of sodium thiocyanate (NaSCN), phenylthiocarbamide (PTC), butyryl-homoserine lactone (C4HSL), n-dodecanoyl-l-homoserine lactone (C12HSL), acetylthiourea (ATU) and 6-n-propylthio uracil (PROP).

11. A method for treating an upper respiratory infection associated disease or disorder and for stimulating an innate antimicrobial response by stimulating nitric oxide (NO) production in the upper respiratory track of a subject having homozygous AVI/AVI allele, homozygous PAV/PAV allele or heterozygous PAV/AVI allele, the method comprising: administering to the upper respiratory tract of said subject a therapeutically effective amount of a quinine or a composition comprising *Antidesma bunius* or its extract wherein administering said quinine or said composition stimulates NO production in sinonasal epithelial cells of the upper respiratory tract of said subject so as to generate an innate antimicrobial response.

12. The method of claim 1, wherein the subject has been determined to be susceptible to the upper respiratory tract infection, and wherein the susceptibility to the upper respiratory tract infection has been determined by the steps of:
    administering to one or more control compounds to the subject to taste;
    administering at different concentration levels at least one bitter tasting compound to the subject to taste;
    rating the intensifies of taste of the control and bitter tasting compounds, and comparing the rated intensifies with pre-calibrated intensifies to determine susceptibility to the upper respiratory tract infection.

13. The method of claim 11, wherein the subject has been determined to be susceptible to the upper respiratory tract infection, and wherein the susceptibility to the upper respiratory tract infection has been determined by the steps of:
    administering one or more control compounds to the subject to taste;
    administering quinine at different concentration levels to the subject to taste;
    rating the intensities of taste of the control and quinine, and comparing the rated intensities with pre-calibrated intensities to determine susceptibility to the upper respiratory tract infection.

14. The method of claim 1, wherein the homoserine lactone is selected from the group consisting of butyryl-homoserine lactone (C4HSL), n-hexanoyl-l-homoserine lactone (C6HSL) and n-dodecanoyl-l-homoserine lactone (C12HSL).

\* \* \* \* \*

SEQUENCE LISTING

```
<160> NUMBER OF SEQ ID NOS: 8

<210> SEQ ID NO 1
<211> LENGTH: 333
<212> TYPE: PRT
<213> ORGANISM: Homo sapiens

<400> SEQUENCE: 1

Met Leu Thr Leu Thr Arg Ile Arg Thr Val Ser Tyr Glu Val Arg Ser
1               5                   10                  15

Thr Phe Leu Phe Ile Ser Val Leu Glu Phe Ala Val Gly Phe Leu Thr
            20                  25                  30

Asn Ala Phe Val Phe Leu Val Asn Phe Trp Asp Val Val Lys Arg Gln
        35                  40                  45

Ala Leu Ser Asn Ser Asp Cys Val Leu Leu Cys Leu Ser Ile Ser Arg
    50                  55                  60

Leu Phe Leu His Gly Leu Leu Phe Leu Ser Ala Ile Gln Leu Thr His
65                  70                  75                  80

Phe Gln Lys Leu Ser Glu Pro Leu Asn His Ser Tyr Gln Ala Ile Ile
                85                  90                  95

Met Leu Trp Met Ile Ala Asn Gln Ala Asn Leu Trp Leu Ala Ala Cys
            100                 105                 110

Leu Ser Leu Leu Tyr Cys Ser Lys Leu Ile Arg Phe Ser His Thr Phe
        115                 120                 125

Leu Ile Cys Leu Ala Ser Trp Val Ser Arg Lys Ile Ser Gln Met Leu
    130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Thr Val Leu Phe Met
                165                 170                 175

Asn Asn Asn Thr Arg Leu Asn Trp Gln Ile Lys Asp Leu Asn Leu Phe
            180                 185                 190

Tyr Ser Phe Leu Phe Cys Tyr Leu Trp Ser Val Pro Pro Phe Leu Leu
        195                 200                 205

Phe Leu Val Ser Ser Gly Met Leu Thr Val Ser Leu Gly Arg His Met
    210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                245                 250                 255

Val Ile Ser Ser Cys Val Ala Phe Ile Ser Val Pro Leu Leu Ile Leu
            260                 265                 270

Trp Arg Asp Lys Ile Gly Val Met Val Cys Val Gly Ile Met Ala Ala
        275                 280                 285

Cys Pro Ser Gly His Ala Ala Ile Leu Ile Ser Gly Asn Ala Lys Leu
    290                 295                 300
```

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                325                 330

<210> SEQ ID NO 2
<211> LENGTH: 1143
<212> TYPE: DNA
<213> ORGANISM: Homo sapiens

<400> SEQUENCE: 2

```
cctttctgca ctgggtggca accaggtctt tagattagcc aactagagaa gagaagtaga      60
atagccaatt agagaagtga catcatgttg actctaactc gcatccgcac tgtgtcctat     120
gaagtcagga gtacatttct gttcatttca gtcctggagt ttgcagtggg gtttctgacc     180
aatgccttcg ttttcttggt gaattttggg gatgtagtga agaggcaggc actgagcaac     240
agtgattgtg tgctgctgtg tctcagcatc agccggcttt tcctgcatgg actgctgttc     300
ctgagtgcta tccagcttac ccacttccag aagttgagtg aaccactgaa ccacagctac     360
caagccatca tcatgctatg gatgattgca aaccaagcca acctctggct tgctgcctgc     420
ctcagcctgc tttactgctc aagctcatc cgtttctctc acccttcct gatctgcttg      480
gcaagctggg tctccaggaa gatctcccag atgctcctgg gtattattct ttgctcctgc     540
atctgcactg tcctctgtgt tggtgctttt tttagcagac tcacttcac agtcacaact       600
gtgctattca tgaataacaa tacaaggctc aactggcaga ttaaagatct caatttattt     660
tattcctttc tcttctgcta tctgtggtct gtgcctcctt tcctattgtt tctggtttct     720
tctgggatgc tgactgtctc cctgggaagg cacatgagga caatgaaggt ctataccaga     780
aactctcgtg accccagcct ggaggccac attaaagccc tcaagtctct tgtctccttt      840
ttctgcttct tgtgatatc atcctgtgtt gccttcatct ctgtgcccct actgattctg      900
tggcgcgaca aaatagggt gatggtttgt gttgggataa tggcagcttg tccctctggg      960
catgcagcca tcctgatctc aggcaatgcc aagttgagga gagctgtgat gaccattctg    1020
ctctgggctc agagcagcct gaaggtaaga gccgaccaca aggcagattc ccggacactg    1080
tgctgagaat ggacatgaaa tgagctcttc attaatacgc ctgtgagtct tcataaatat    1140
gcc                                                                  1143
```

<210> SEQ ID NO 3
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 3

```
ccagaugcuc cuggguauua uucuu                                           25
```

<210> SEQ ID NO 4
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 4

```
aagaauaaua cccaggagca ucugg                                           25
```

```
<210> SEQ ID NO 5
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 5
ggcacaugag gacaaugaag gucua                                      25

<210> SEQ ID NO 6
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 6
uagaccuuca uuguccucau gugcc                                      25

<210> SEQ ID NO 7
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 7
ccuacugauu cuguggcgcg acaaa                                      25

<210> SEQ ID NO 8
<211> LENGTH: 25
<212> TYPE: RNA
<213> ORGANISM: Artificial Sequence
<220> FEATURE:
<223> OTHER INFORMATION: siRNA directed against human T2R38

<400> SEQUENCE: 8
uuugucgcgc cacagaauca guagg                                      25
```